US009062044B2

(12) United States Patent
Branstetter et al.

(10) Patent No.: US 9,062,044 B2
(45) Date of Patent: Jun. 23, 2015

(54) DISUBSTITUTED OCTAHYDROPYRROLO[3,4-C]PYRROLES AS OREXIN RECEPTOR MODULATORS

(75) Inventors: Bryan James Branstetter, Carlsbad, CA (US); Michael A. Letavic, San Diego, CA (US); Kiev S. Ly, San Diego, CA (US); Dale A. Rudolph, San Diego, CA (US); Brad M. Savall, San Diego, CA (US); Chandravadan R. Shah, San Diego, CA (US); Brock T. Shireman, Poway, CA (US)

(73) Assignee: Janssen Pharmaceutica NV (BE)

( * ) Notice: Subject to any disclaimer, the term of this patent is extended or adjusted under 35 U.S.C. 154(b) by 506 days.

(21) Appl. No.: 13/503,298

(22) PCT Filed: Oct. 21, 2010

(86) PCT No.: PCT/US2010/053611
§ 371 (c)(1),
(2), (4) Date: Jan. 17, 2013

(87) PCT Pub. No.: WO2011/050202
PCT Pub. Date: Apr. 28, 2011

(65) Prior Publication Data
US 2013/0137672 A1    May 30, 2013

Related U.S. Application Data

(60) Provisional application No. 61/254,517, filed on Oct. 23, 2009.

(51) Int. Cl.
*A61K 31/397* (2006.01)
*C07D 471/04* (2006.01)
*C07D 487/04* (2006.01)

(52) U.S. Cl.
CPC ............ *C07D 471/04* (2013.01); *C07D 487/04* (2013.01)

(58) Field of Classification Search
None
See application file for complete search history.

(56) References Cited

U.S. PATENT DOCUMENTS

| 2002/0019388 A1 | 2/2002 | Schrimpf et al. |
| 2004/0242641 A1 | 12/2004 | Buckley et al. |
| 2005/0065178 A1 | 3/2005 | Basha et al. |
| 2005/0101602 A1 | 5/2005 | Basha et al. |
| 2006/0258672 A1 | 11/2006 | Barbosa et al. |
| 2008/0132490 A1 | 6/2008 | Bergman et al. |
| 2009/0163485 A1 | 6/2009 | Knust et al. |
| 2010/0160344 A1 | 6/2010 | Alvaro et al. |
| 2010/0160345 A1 | 6/2010 | Alvaro et al. |

FOREIGN PATENT DOCUMENTS

| WO | WO 01/061347 | 11/2001 |
| WO | WO 03/002561 | 1/2003 |
| WO | WO 03/051672 | 4/2003 |
| WO | WO 2004/004733 A1 | 1/2004 |
| WO | WO 2004/033418 | 4/2004 |
| WO | WO 2004/041791 | 5/2004 |
| WO | WO 2006/056848 A1 | 6/2006 |
| WO | WO 2006/123121 | 11/2006 |
| WO | WO 2006/124748 A2 | 11/2006 |
| WO | WO 2006/124897 | 11/2006 |
| WO | WO 2007/126934 | 11/2007 |
| WO | WO 2007/126935 | 11/2007 |
| WO | WO 2008/008517 | 1/2008 |
| WO | WO 2008/008518 | 1/2008 |
| WO | WO 2008/008551 | 1/2008 |
| WO | WO 2008/034731 A1 | 3/2008 |
| WO | WO 2006/067121 | 6/2008 |
| WO | WO 2008/069997 | 6/2008 |
| WO | WO 2008/143856 | 11/2008 |
| WO | WO 2009/016286 A2 | 2/2009 |
| WO | WO 2009/022311 | 2/2009 |
| WO | WO 2009 037394 A2 | 3/2009 |
| WO | WO 2009/058238 | 5/2009 |
| WO | WO 2009/061197 | 7/2009 |
| WO | WO 2009/124956 | 10/2009 |
| WO | WO 2010/017260 | 2/2010 |
| WO | WO 2010/048010 | 4/2010 |
| WO | WO 2010/048012 | 4/2010 |
| WO | WO 2010/048013 | 4/2010 |
| WO | WO 2010/048014 | 4/2010 |
| WO | WO 2010/048017 | 4/2010 |
| WO | WO 2010/051236 | 5/2010 |
| WO | WO 2010/051237 | 5/2010 |
| WO | WO 2010/051238 | 5/2010 |
| WO | WO 2010/060470 | 6/2010 |
| WO | WO 2010/060471 | 6/2010 |
| WO | WO 2010/060472 | 6/2010 |
| WO | WO 2010/063662 | 6/2010 |
| WO | WO 2010/063663 | 6/2010 |
| WO | WO 2010/072722 | 6/2010 |

OTHER PUBLICATIONS

EP Communication, based on Ep App. No. 10773477, dated Apr. 19, 2013.
International Search Report dated Dec. 10, 2010, Int'l. App. No. PCT/US2010/053611, filing date Oct. 21, 2010.
Aston-Jones, G. et al., "Role of lateral hypothalamic orexin neurons in reward processing and addiction" *Neuropharmacology* 2009, 56 Supp.1 1:pp. 112-121.
Bagshawe, K., "Antibody-Directed Enzyme Prodrug Therapy: A Review" Drug Development Research 34:220-230, 1995.
Berg, S. et al., "Pharmaceutical Salts" Journ. of Pharm. Sciences, 1977, 66:1-19, & Handbook of Pharmaceutical Salts, Properties, Selection & Use, Stahl and Wermuth, Eds., Wiley-VCH and VHCA, Zurich.

(Continued)

*Primary Examiner* — Craig Ricci
(74) *Attorney, Agent, or Firm* — Mary A. Appollina

(57) ABSTRACT

Certain disubstituted 3,8-diaza-bicyclo[4.2.0]octane and 3,6-diazabicyclo[3.2.0]heptane are described, which are useful as orexin inhibitors. Such compounds may be useful in pharmaceutical compositions and methods for the treatment of diseased states, disorders, and conditions mediated by orexin activity, such as insomnia.

18 Claims, No Drawings

(56) References Cited

OTHER PUBLICATIONS

Bertolini, G., et al., "A New Rational Hypothesis for the Pharmacophore of the Active Metabolite of Leflunomide, a Potent Immunosuppressive Drug", J. Med. Chem 1997, 40, 2011-2016.

Bodor, N., "Novel Approaches to the Design of Safer Drugs: Soft Drugs and Site-Specific Chemical Delivery Systems". Advanced Drug Res., 1984 13, 224-331.

Boss, et al. "Biomedical App.lication of Orexin/Hypocretin Receptor Ligands in Neuroscience", J. Med. Chem., 2009, 52(4), pp. 891-903.

Brisbare-Roch et al. "Promotion of sleep by targeting the orexin system in rats, dogs and humans", Nature Medicine, 2007, 13, pp. 150-155.

Bundgaard, H. (Ed.) "Design of Prodrugs" Elsevier, 1985.

Chemelli et al. "Narcolepsy in orexin knockout mice: Molecular genetics of sleep regulation", Cell 1999, 98, pp. 437-451.

Chen et al."Pressor effects of orexins injected intracisternally and to rostral ventrolateral medulla of anesthetized rats", Am. J. Physiol., 2000, 278, pp. R692-R697.

Coleman et al."Design and synthesis of conformationally constrained N,N-disubstituted 1,4-diazepanes as potent orexin receptor antagonists" Bioorganic & Medicinal Chemistry Letters, 2010, 20 pp. 2311-2315.

Coleman et al."Discovery of 3,9-diazabicyclo[4.2.1]nonanes as potent orexin receptor antagonists with sleep-promoting activity in the rat" Bioorganic & Medicinal Chemistry Letters, 2010, 20 pp. 4201-4205.

Considine, G.D., ed., Van Nostrand's Encyclopedia of Chemistry, 5th ed. 2005 p. 261.

Cox et al., Conformational analysis of N,N-disubstituted-1,4-diazepane orexin receptor antagonists and implications for receptor binding, Bioorganic & Medicinal Chemistry Letters, 2009. 19 pp. 2997-3001.

Cox et al., "Discovery of the dual orexin receptor antagonist [(7R)-4-(5-chloro-1,3-benzoxazol-2-yl)-7-methyl-1,4-diazepan-1-yl][(5-methyl-2-(2H-1,2,3-triazol-2-yl)phenyl]methanone (MK-4305) for the treatment of insomnia" Journal of Medicinal Chemistry 2010, 53(14):pp. 5320-5332.

Covington et al., Handbook of Chemistry and Physics, 84th ed., 2003-2004 pp. 8-37 to 8-44.

Dayas, C. V. et al., "Stimuli linked to ethanol availability activate hypothalamic CART and orexin neurons in a reinstatement model of relapse" Biological Psychiatry 2008, 63(2):152-157.

Dugovic, C. et al., "Blockade of Orexin-1 Receptors Attenuates Orexin-2 Receptor Antagonism-Induced Sleep Promotion in the Rat" Journal of Pharmacology & Experimental Therapeutics 2009, 330(1) pp. 142-151.

Fleisher, D. et al., "Improved Oral Drug Delivery: Solubility Limitations Overcome by the Use of Prodrugs", Advanced Drug Delivery Reviews, 1996, 19:115-130.

Frost, J., et al., "Synthesis and Structure-Activity Relationships of 3,8-Diazabicyclclo [4.2.0] Octane Ligands, Potent Nicotinic Acetylcholine Receptor Agonists" J. Med. Chem. 2006, 49, 7643-7853.

Georgescu, D. et al., "Involvement of the lateral hypothalamic peptide orexin in morphine dependence and withdrawal" Journal of Neuroscience 2003, 23(8), pp. 3106-3111.

Hara et al. "Genetic ablation of orexin neurons in mice results in narcolepsy, hypophagia, and obesity", Neuron, 2001, 30 (2), pp. 345-354.

Hamlin, A. S. et al., "The neural correlates and role of D1 dopamine receptors in renewal of extinguished alcohol-seeking" Neuroscience 2007, 146(2) pp. 525-536.

Kane, J.K. et al., "Nicotine Up-Regulates Expression of Orexin and Its Receptors in Rat Brain" Endocrinology 2000 141(10). pp. 3623-3629.

Kane, J.K., "Hypothalamic orexin-A binding sites are downregulated by chronic nicotine treatment in the rat" Neuroscience Letters 2001, 298(1):pp. 1-4.

Kang et al., "Amyloid-β Dynamics Are Regulated by Orexin and the Sleep-Wake Cycle", Science Express, 2009, pp. 1-10.

Kirchgessner and Liu "Orexin synthesis and response in the gut", Neuron, 1999, 24 (4), pp. 941-951.

Langmead et al. "Characterisation of the binding of (3H)-SB-674042, a novel nonpeptide antagonist, to the human orexin-1 receptor", British Journal of Pharmacology 2004, 141 (2), pp. 340-346.

Larsen, Design and Application of Prodrugs, Drug Design and Development 1991 (Krogsgaard-Larsen, et al., eds., Harwood Academic Publishers.

Lawrence, et al., "The orexin system regulates alcohol-seeking in rats" British Journal of Pharmacology 2006, 148(6) pp. 752-759.

Lin et al. "The sleep disorder canine narcolepsy is caused by a mutation in the hypocretin (orexin) receptor 2 gene", Cell 1999, 98, pp. 365-376.

Malherbe, P. et al., Biochemical and behavioural characterization of EMPA, a novel high-affinity, selective antagonist for the $OX_2$ Receptor, British Journal of Pharmacology 2009 156:1326-1341.

Malherbe et al. "Biochemical and electrophysiological characterization of almorexant, a dual orexin 1 receptor (OX1)/orexin 2 receptor ($OX_2$) antagonist: comparison with selective OX1 and OX2 antagonists", Molecular Pharmacology 2009, 76(3) pp. 618-631.

Mignot & Thorsby "Narcolepsy and the HLA System", New England J. Med. 2001, 344 (9), pp. 692.

Mignot et al. "Complex HLA-DR and -DQ interactions confer risk of narcolepsy-cataplexy in three ethnic groups", Am. J. Hum. Genet. 2001, 68 (3), pp. 686-699.

Nakamura et al. "Orexin-induced hyperlocomotion and stereotypy are mediated by the dopaminergic system", Brain Res. 2000, 873(1), pp. 181-187.

Paulekuhn, G. et al., "Trends in Active Pharmaceutical Ingredient Salt Selection based on Analysis of the Orange Book database", J. Med. Chem, 2007 50:6665-6672.

Peyron et al. "Neurons containing hypocretin (Orexin) project to multiple neuronal systems" J. Neurosci., 1998, 18(23), pp. 9996-10015.

Peyron et al. "A mutation in a case of early onset narcolepsy and a generalized absence of hypocretin peptides in human narcoleptic brains", Nature Med. 2000, 6 (9), pp. 991-997.

Piper et al. "The novel brain neuropeptide, orexin-A, modulates the sleep-wake cycle of rats", European Journal of Neuroscience, 2000, 12(2), pp. 726-730.

Richards, J.K., et al., "Inhibition of orexin-1/hypocretin-1 receptors inhibits yohimbine-induced reinstatement of ethanol and sucrose seeking in Long-Evans rats" Psychopharmacology 2008, 199(1):pp. 109-117.

Robinson, R. et al., "Discovery of the Hernifumarate and (α-L-Alanyloxy)methyl Ether as Prodrugs of an Antirheumatic Oxindone: Prodrugs for the Enolic OH Group" J. Med. Chem. 1996 39 10-18.

Sakurai, T., "The neural circuit of orexin (hypocretin): maintaining sleep and wakefulness", 2007, Nature Reviews Neuroscience, 8(3):pp. 171-181.

Sakurai, T. et al., "Orexins and orexin receptors: a family of hypothalamic neuropeptides and G protein-coupled receptors that regulate feeding behavior" Cell 1996, 92(4): pp. 573-585.

Sakurai, T. "Orexins and orexin receptors: implication in feeding behavior" Regulatory Peptides 1999, 85(1):pp. 25-30.

Samson et al."Cardiovascular regulatory actions of the hypocretins in brain", Brain Res., 1999, 831: pp. 248-253.

Schneider, E. R., "Orexigenic peptides and alcohol intake: differential effects of orexin, galanin, and ghrelin" Alcoholism: Clinical & Experimental Research 2007. 31(11):pp. 1858-1865.

Shan, D. et al., "Prodrug Strategies Based on the Intramolecular Cyclization Reactions" J. Pharm. Sci. 1997 86(7) 765-767.

Shirasaka et al."Sympathetic and cardiovascular actions of orexins in conscious rats", Am. J. Physiol., 1999, 277, pp. R1780-R1785.

Takahashi et al."Stimulation of gastric acid secretion by centrally administered orexin-A in conscious rats", Biochem. Biophys. Res. Commun., 1999, 254 (3), pp. 623-627.

Van Den Pol, "Hypothalamic hypocretin (orexin): Robust innervation of the spinal cord" J. Neurosci., 1999, 19(8), pp. 3171-3182.

Winrow, C. J., "Orexin receptor antagonism prevents transcriptional and behavioral plasticity resulting from stimulant exposure" Neuropharmacology 2010, 58(1):pp. 185-194.

Yamanaka et al."Orexins activate histaminergic neurons via the orexin 2 receptor", Biochem. Biophys. Res. Comm. 2002, 290 (4), pp. 1237-1245.

DISUBSTITUTED OCTAHYDROPYRROLO[3,4-C]PYRROLES AS OREXIN RECEPTOR MODULATORS

CROSS-REFERENCE TO RELATED APPLICATIONS

This application is a national phase of International Application No. PCT/US2010/053611 filed Oct. 21, 2010 and claims benefit of priority under 35 U.S.C. §119(e) of U.S. Provisional Application No. 61/254,517 filed on Oct. 23, 2009.

FIELD OF THE INVENTION

The present invention relates to certain disubstituted 3,8-diaza-bicyclo[4.2.0]octane and 3,6-diazabicyclo[3.2.0]heptane compounds, pharmaceutical compositions containing them, methods of making them, and methods of using them for the modulation of the orexin receptor and for the treatment of disease states, disorders, and conditions mediated by orexin receptor activity.

BACKGROUND OF THE INVENTION

Orexin (or hypocretin) signaling is mediated by two receptors and two peptide agonists. The two orexin peptides (orexin A and orexin B) herein after referred to as orexins, bind to two high affinity receptors, termed orexin-1 and orexin-2 receptors. The orexin-1 receptor is selective in favor of orexin A, while the orexin-2 receptor binds both orexins with similar affinities. The orexins, are cleavage products of the same gene, prepro orexin. In the central nervous system neurons expressing prepro-orexin, the precursor from which orexin is produced, are found in the periformical nucleus, the dorsal hypothalamus and the lateral hypothalamus (C. Peyron et al., *J. Neurosci.*, 1998, 18(23), 9996-10015). Orexinergic cells in these nuclei project to many areas of the brain, extending rostrally to the olfactory bulbs and caudally to the spinal cord (van den Pol, A. N. et al., *J. Neuroscience.*, 1999, 19(8), 3171-3182).

The broad CNS distribution of orexin projections and neurons expressing orexin receptors is suggestive of orexin involvement in a number of physiological functions including; feeding, drinking, arousal, stress, reward, metabolism and reproduction (T. Sakurai, *Nature Reviews Neuroscience*, 2007, 8(3), 171-181).

The targeted necrosis of cells expressing prepro-orexin suggests the most physiologically important roles of the orexins are likely to be effects on arousal, feeding and metabolism (J. Hara et al., *Neuron*, 2001, 30, 345-354). A prominent orexin neuronal projection via the vagus nerve probably mediates central orexin effects on cardiac parameters (W. K. Samson et al., *Brain Res.*, 1999, 831, 248-253; T. Shirasaka et al., *Am. J. Physiol.*, 1999, 277, R1780-R1785; C.-T. Chen et al., *Am. J. Physiol.*, 2000, 278, R692-R697), gastric acid secretion and gastric motility (A. L. Kirchgessner and M.-T. Liu, *Neuron*, 1999, 24, 941-951; N. Takahashi et al., *Biochem. Biophys. Res. Commun.*, 1999, 254, 623-627).

Several lines of evidence indicate that the orexin system is an important modulator of arousal. Rodents administered orexins intracerebroventricularly spend more time awake (Piper et al., *J. Neurosci.* 2000, 12, 726-730). Orexin-mediated effects on arousal have been linked to orexin neuronal projections to histaminergic neurons in the tuberomammillary nucleus (TMN) (Yamanaka et al., *Biochem. Biophys. Res. Comm.* 2002, 290, 1237-1245). TMN neurons express the orexin-2 receptor primarily, and the orexin-1 receptor to a lesser extent. Rodents whose prepro orexin gene has been knocked out, or whose orexigenic neurons have been lesioned, display altered sleep/wake cycles similar to narcolepsy (Chemelli et al., *Cell* 1999, 98, 437-451; Hara et al., 2001, supra). Dog models of narcolepsy have been shown to have mutant or non-functional orexin-2 receptors (Lin et al., *Cell* 1999, 98, 365-376). Human narcolepsy appears to be linked to deficient orexin signaling, likely related to immune ablation of orexinergic neurons in the lateral hypothalamus (Mignot et al., *Am. J. Hum. Genet.* 2001, 68: 686-699; Minot & Thorsby, *New England J. Med.* 2001, 344, 692), or, in rare cases, to mutations in the orexin-2 gene (Peyron et al., *Nature Med.* 2000, 6, 991-997). The disclosure that rats, dogs and humans treated with the dual orexin-1/2 receptor antagonist, ACT-078573 (Brisbare-Roch et al., *Nature Medicine*, 2007, 13, 150-155) exhibited decreased alertness together with characteristic clinical and EEG (electroencephalographic) signs of sleep provides evidence to support a role for the orexin system in the regulation of arousal, sleep and wake states. EEG data indicates that orexin-2 may be more important than orexin-1 in the modulation of sleep/wake (P. Malherbe et al., *Molecular Pharmacology* (2009) 76(3):618-31; C. Dugovic et al., *J. Pharmacol. Exp. Ther.*, 2009, 330(1), 142-151). Disorders of the sleep-wake cycle are therefore likely targets for orexin-2 receptor antagonist therapy. Examples of such disorders include sleep-wake transition disorders, insomnia, restless legs syndrome, jet-lag, disturbed sleep, and sleep disorders secondary to neurological disorders (e.g., manias, depressions, manic depression, schizophrenia, and pain syndromes (e.g., fibromyalgia, neuropathic pain).

The orexin system also interacts with brain dopamine systems. Intracerebroventricular injections of orexins in mice increase locomotor activity, grooming and stereotypy; these behavioral effects are reversed by administration of $D_2$ dopamine receptor antagonists (Nakamura et al., *Brain Research*, 873(1), 181-7). Therefore, orexin-2 modulators may be useful to treat various neurological disorders; e.g., agonists or up-regulators to treat catatonia, antagonists or down-regulators to treat Parkinson's disease, Tourette's syndrome, anxiety, delerium and dementias.

Recent evidence indicates a role for orexin in the pathogenesis of Alzheimers disease (Kang et al, *Science Express*, 2009, 1-10). Brain interstitial fluid levels of amyloid-beta were demonstrated to fluctuate diurnally in both humans and rodents with sleep deprivation in rodents leading to significant increases in brain interstitial fluid levels of amyloid-beta. Infusion of a dual orexin antagonist in rodents suppressed interstitial levels of amyloid-beta and abolished the natural diurnal variation of amyloid-beta. The reduction of interstitial fluid amyloid-beta levels is correlated with reduced amyloid plaque formation, a hallmark of Alzheimer's disease, and consequently the regulation of sleep time could potentially inhibit amyloid-beta aggregation and slow the progression of Alzheimer's disease.

Orexin neurons project to many regions of the brain associated with reward function (T. Sakurai, supra) and research, focusing on animal models of drug intake, reward, and reinstatement, has expanded the link between the orexin system and addiction. A comprehensive set of data suggest that drugs of abuse activate the orexin system, which in turn enhances drug reward or drug seeking (G. Aston-Jones et al., *Neuropharmacology*, 2009, 56 (Suppl 1) 112-121. Thus interactions between nicotine (J. K. Kane et al., *Endocrinology*, 2000, 141(10), 3623-3629; J. K. Kane et al., *Neurosci. Lett.*, 2001, 298(1), 1-4), morphine (D. Georgescu, et al., *J. Neurosci.*, 2003, 23(8), 3106-3111) and amphetamine (C. J. Winrow et al., *Neuropharmacology,* 2010, 58(1), 185-94) and the orexin system have been demonstrated. Additional studies from a number of laboratories have demonstrated an important relationship between the Orexin system and ethanol consumption. As examples, ethanol consumption in an alcohol-preferring strain of rat was shown to up regulate Orexin mRNA in the lateral hypothalamus and that an Orexin-1 receptor antagonist reduced operant responding for ethanol (Lawrence, et. al., *Br. J. Pharmacol.,* 2006, 148, 752-759). Treatment with an orexin-1 antagonist has also been shown to decrease operant responding for ethanol (Richards, et. al., *Psychopharmacology,* 2008, 199 (1), 109-117). Other studies have demonstrated increased Fos activation of orexin neurons following contextual reinstatement to ethanol seeking (Dayas, et. al., *Biol. Psychiatry,* 2008, 63 (2), 152-157 and Hamlin, et. al., *Neuroscience,* 2007, 146, 525-536). Studies have also shown increased ethanol consumption following Orexin infusion into the paraventricular nucleus of the hypothalamus or in the lateral hypothalamus (Schneider, et. al., *Alcohol. Clin. Exp. Res.,* 2007, 31(11), 1858-1865). These studies provide evidence that modulation of the Orexin system effects alcohol preference and therefore Orexin receptor antagonists are likely to be useful for the treatment of alcoholism.

Orexins and their receptors have been found in both the myenteric and submucosal plexus of the enteric nervous system, where orexins have been shown to increase motility in vitro (Kirchgessner & Liu, *Neuron* 1999, 24, 941-951) and to stimulate gastric acid secretion in vitro (Takahashi et al., *Biochem. Biophys. Res. Comm.* 1999, 254, 623-627). Orexin mediated effects on the gut may be driven by a projection via the vagus nerve (van den Pol, 1999, supra), as vagotomy or atropine prevent the effect of an intracerebroventricular injection of orexin on gastric acid secretion (Takahashi et al., 1999, supra). Orexin receptor antagonists or other down-regulators of orexin receptor-mediated systems are therefore potential treatments for ulcers, irritable bowel syndrome, diarrhea and gastroesophageal reflux.

Body weight may also be affected by orexin-mediated regulation of appetite and metabolism (T. Sakurai et al., *Cell,* 1998, 92(4), 573-585; T. Sakurai, *Reg. Pept.,* 1999, 85(1), 25-30). Some effects of orexin on metabolism and appetite may be mediated in the gut, where, as mentioned, orexins alter gastric motility and gastric acid secretion. Orexin receptor antagonists therefore are likely to be useful in treatment of overweight or obesity and conditions related to overweight or obesity, such as insulin resistance, type II diabetes, hyperlipidemia, gallstones, angina, hypertension, breathlessness, tachycardia, infertility, sleep apnea, back and joint pain, varicose veins and osteoarthritis. Conversely, orexin receptor agonists are likely to be useful in treatment of underweight and related conditions such as hypotension, bradycardia, ammenorrhea and related infertility, and eating disorders such as anorexia and bulimia.

Intracerebroventricularly administered orexins have been shown to increase mean arterial pressure and heart rate in freely moving (awake) animals (Samson et al., *Brain Res.* 1999, 831, 248-253; Shirasaka et al., *Am. J. Physiol.* 1999, 277, R1780-R1785) and in urethane-anesthetized animals (Chen et al., *Am. J. Physiol.* 2000, 278, R692-R697), with similar results. Orexin receptor agonists may therefore be candidates for treatment of hypotension, bradycardia and heart failure related thereto, while orexin receptor antagonists may be useful for treatment of hypertension, tachycardia and other arrhythmias, angina pectoris and acute heart failure.

From the foregoing discussion, it can be seen that the identification of orexin receptor modulators, in one embodiment modulators of the orexin-2 receptor, will be of great advantage in the development of therapeutic agents for the treatment of a wide variety of disorders that are mediated through these receptor systems.

Citation of a reference herein shall not be construed as an admission that such reference is prior art to the present invention. All publications referred to herein are incorporated by reference in their entireties.

Various small-molecule orexin receptor modulators have been reported e.g., N-aroyl cyclic amine derivatives (International Publication No. WO2003002561, Jan. 9, 3003), ethylene diamine derivatives (International Publication No. WO2003051872, Jun. 26, 2003), sulfonylamino-acetic acid derivatives (International Publication No. WO2004033418, Apr. 22, 2004), N-aryl acetyl cyclic amine derivatives (International Publication No. WO2004041791, May 21, 2004), diazepan derivatives (International Publication No. WO2007126935, Nov. 8, 2007), amidoethylthioether derivatives (International Publication No. WO2007126934, Nov. 8, 2007), 2-substituted proline bis-amide derivatives (International Publication No. WO2008008551, Jan. 17, 2008), bridged diazepan derivatives (International Publication No. WO2008008517, Jan. 17, 2008), substituted diazepan derivatives (International Publication No. WO2008008518, Jan. 17, 2008; US20080132490, WO2009058238), oxo bridged diazepan derivatives (International Publication No. WO2008143856, Nov. 27, 2008), 1,2-diamido ethylene derivatives (International Publication No. WO2009022311, Feb. 19, 2009), heteroaryl derivatives (International Publication No. WO20090163485, Jun. 25, 2009), methyl substituted piperidinyl derivatives (International Publication No. WO2009124956, Oct. 15, 2009), N,N-disubstituted-1,4-diazepane derivatives (Cox et al, *Bioorganic & Medicinal Chemistry Letters,* 2009, 19(11), 2997-3001), Orexin/Hypocretin receptor ligands (Boss, et al., *Journal of Medicinal Chemistry,* 2009, 52(4), 891-903) 3,9-diazabicyclo[4.2.1]nonanes (Coleman et al, *Bioorganic & Medicinal Chemistry Letters,* 2010, 20(14), 4201-4205), the dual orexin receptor antagonist, [(7R)-4-(5-Chloro-1,3-benzoxazol-2-yl)-7-methyl-1,4-diazepan-1-yl][5-methyl-2-(2H-1,2,3-triazol-2-yl)phenyl]methanone, (Cox, et. al., *Journal of Medicinal Chemistry,* 2010 53(14) 5320-5332), pyridazine carboxamide derivatives (International Publication No. WO2010051238), 2,5-disubstituted benzamide derivatives (International Publication No WO2010051237, May 6, 2010), isonicotinamides (International Publication No WO2010051236), heterocyclylbenzoylpiperazines derivatives (International Publication No WO201048012), substituted diazepane derivatives (International Publication No WO2010048017), substituted pyrrolidine derivatives (International Publication No WO2010048014), triazolylbenzoylpiperidine derivatives (International Publication No WO2010048010), triazolylbenzoylmorpholine derivatives (WO2010048013), conformationally restrained N,N disubstituted 1,4-diazapane derivatives (Coleman et al, *Bioorganic & Medicinal Chemistry Letters,* 2010, 20(7), 2311-2315), tripyridyl carboxamide derivatives (International Publication No WO2010017260), imidazopyridylmethyl substituted piperidine derivatives (International Publication No WO2010072722), imidazopyrazine substituted piperidine derivatives (US2010160344, Jun. 24, 2010; US20100160345, Jun. 24, 2010; International Publication No WO2010060472, Jun. 3, 2010), N-{[(1R,4S,6R)-3-(2-pyridinylcarbonyl)-3-azabicyclo[4.1.0]hept-4-yl]methyl}-2-heteroarylamine derivatives (International Publication No WO2010063663), N-{[(1S,4S,6S)-3-(2-pyridinylcarbonyl)-3-azabicyclo[4.1.0]hept-4-yl]methyl}-2-heteroarylamine derivatives (International Publication No WO2010063662), imidazopyrimidine derivatives (International Publication No WO2010060471), and imidazopyrazine derivatives (International Publication No WO2010060470). There remains a need, however, for potent orexin receptor modulators with desirable pharmaceutical properties.

Substituted diaza-bicyclic compounds have been reported as active central nervous system agents (International Publication No. WO2001081347, Nov. 1, 2001; US2002/0019388, Feb. 14, 2002), α7 acetylcholine receptor modulators (US2005/101602, May 12, 2005; US2005/0065178, Mar. 24, 2005 and Frost et al, *Journal of Medicinal Chemistry*, 2006, 49(26), 7843-7853), proline transporter inhibitors for the treatment of cognitive impairment (WO2008067121, Jun. 5, 2008) and for improving cognition (WO 2006 124897, Nov. 23, 2006 and US20060258672, Nov. 16, 2006), as androgen receptor ligands for the treatment of androgen receptor associated conditions including cancer (WO2009081197, Jul. 2, 2009), and as histone deacetylase inhibitors for the treatment of cancers, neurodegenerative diseases and autoimmune diseases (WO20060123121, Nov. 23, 2006).

SUMMARY OF THE INVENTION

Certain disubstituted 3,8-diaza-bicyclo[4.2.0]octane and 3,6-diazabicyclo[3.2.0]heptane derivatives have been found to have orexin-modulating activity. Thus, the invention is directed to the general and preferred embodiments defined, respectively, by the independent and dependent claims appended hereto, which are incorporated by reference herein.

In one general aspect, the invention is directed to a chemical entity of Formula (I):

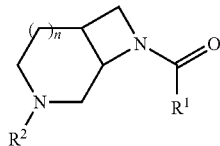

wherein
n is 0-1;
$R^1$ is a member selected from the group consisting of:
  a) phenyl substituted or unsubstituted with $R^a$, and substituted in the ortho position with $R^b$;
    $R^a$ is a member independently selected from the group consisting of: halo, —$C_{1-4}$alkyl, and —$C_{1-4}$alkoxy;
    $R^b$ is a member selected from the group consisting of:
      i) halo or —$C_{1-4}$alkoxy,
      ii) thiophen-2-yl, 2H-1,2,3-triazole, 1H-1,2,3-triazol-1-yl, 1H-pyrazol-1-yl, 1H-pyrazol-5-yl, pyrimidin-2-yl, or 3-methyl-1,2,4-oxadiazol-5-yl; and
      iii) phenyl;
  b) pyridine substituted or unsubstituted adjacent to the point of attachment by $R^1$ with a one or two members independently selected from the group consisting of: $C_{1-4}$alkyl and 1H-1,2,3-triazol-1-yl; and
  c) methylthiazole substituted with 2-fluorophenyl;
$R^2$ is a member selected from the group consisting of:
  a) 6-membered heteroaryl ring containing two nitrogen members substituted or unsubstituted with one or more members selected from the group consisting of: —$C_{1-4}$alkyl, —$C_{1-4}$alkoxy, —$CF_3$, halo, —N($C_{1-4}$alkyl)$_2$, —$NH_2$, and phenyl;
  b) pyridine substituted or unsubstituted with one or more members independently selected from the group consisting of: —$CF_3$ and —$C_{1-4}$alkyl;
  c) quinoxalin-2-yl or quinoline substituted or unsubstituted with —$C_{1-4}$alkyl;
  d) benzooxazol-2-yl substituted or unsubstituted with halo; and
  e) 4-methyl-6,7-dihydro-5H-cyclopenta[d]pyrimidine.

In another general aspect, the invention is directed to a chemical entity of Formula (II):

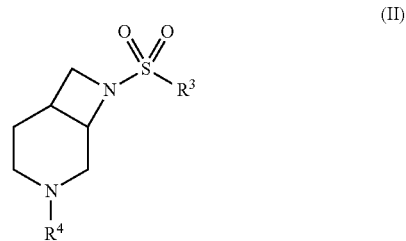

wherein
$R^3$ is phenyl substituted or unsubstituted with $C_{1-4}$alkyl and substituted in the ortho position with $C_{1-4}$alkyl; and
$R^4$ is selected from the group consisting of: quinoxaline and 4-phenyl-pyrimidin-2-yl.

Further embodiments are provided by pharmaceutically acceptable salts of compounds of Formula (I) or Formula (II), pharmaceutically acceptable prodrugs of compounds of Formula (I) or Formula (II), and pharmaceutically active metabolites of compounds of Formula (I) or Formula (II).

In certain embodiments, the compound of Formula (I) or Formula (II) is a compound selected from those species described or exemplified in the detailed description below.

In a further aspect, the invention relates to pharmaceutical compositions for treating a disease, disorder, or medical condition mediated by orexin receptor activity, comprising an effective amount of at least one chemical entity selected from compounds of Formula (I) or Formula (II), pharmaceutically acceptable salts of compounds of Formula (I) or Formula (II), pharmaceutically acceptable prodrugs of compounds of Formula (I) or Formula (II), and pharmaceutically active metabolites of Formula (I) or Formula (II).

Pharmaceutical compositions according to the invention may further comprise one or more pharmaceutically acceptable excipients.

In another aspect, the chemical embodiments of the present invention are useful as orexin receptor modulators. Thus, the invention is directed to a method for modulating orexin receptor activity, including when such receptor is in a subject, comprising exposing orexin receptor to an effective amount of at least one chemical entity selected from compounds of Formula (I) or Formula (II), pharmaceutically acceptable salts of compounds of Formula (I) or Formula (II), pharmaceutically acceptable prodrugs of compounds of Formula (I) or Formula (II), and pharmaceutically active metabolites of compounds of Formula (I) or Formula (II).

In another aspect, the invention is directed to a method of treating a subject suffering from or diagnosed with a disease, disorder, or medical condition mediated by orexin receptor activity, comprising administering to the subject in need of such treatment an effective amount of at least one chemical entity selected from compounds of Formula (I) or Formula (II), pharmaceutically acceptable salts of compounds of Formula (I) or Formula (II), pharmaceutically acceptable prodrugs of compounds of Formula (I) or Formula (II), and pharmaceutically active metabolites of compounds of Formula (I) or Formula (II). Additional embodiments of methods of treatment are set forth in the detailed description.

In another aspect, method of studying isotopically labeled compounds in metabolic studies (preferably with $^{14}$C), reaction kinetic studies (with, for example $^{2}$H or $^{3}$H), detection or imaging techniques [such as positron emission tomography (PET) or single-photon emission computed tomography (SPECT)] including drug or substrate tissue distribution assays, or in radioactive treatment of patients. For example, an $^{18}$F or $^{11}$C labeled compound may be particularly preferred for PET or an $I^{123}$ for SPECT studies.

An object of the present invention is to overcome or ameliorate at least one of the disadvantages of the conventional methodologies and/or prior art, or to provide a useful alternative thereto. Additional embodiments, features, and advantages of the invention will be apparent from the following detailed description and through practice of the invention.

DETAILED DESCRIPTION

The invention may be more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me, which also may be structurally depicted by the symbol, "/"), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "alkoxy" includes a straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on. "Aminoalkyl", "thioalkyl", and "sulfonylalkyl" are analogous to alkoxy, replacing the terminal oxygen atom of alkoxy with, respectively, NH (or NR), S, and SO$_2$.

The term "cyano" refers to the group —CN.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

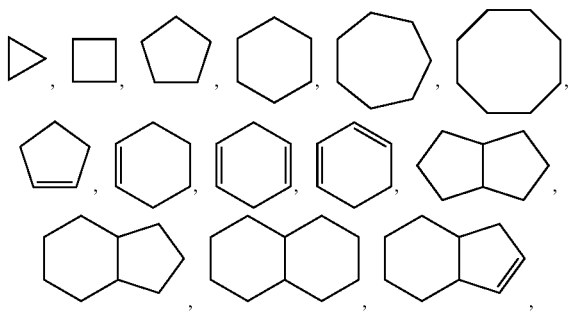

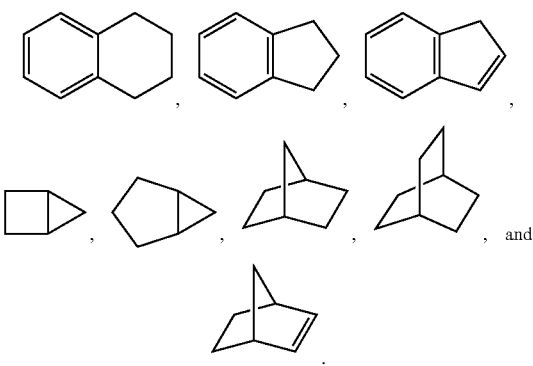

A "heterocycloalkyl" refers to a monocyclic ring structure that is saturated or partially saturated and has from 4 to 7 ring atoms per ring structure selected from carbon atoms and up to two heteroatoms selected from nitrogen, oxygen, and sulfur. The ring structure may optionally contain up to two oxo groups on sulfur ring members. Illustrative entities, in the form of properly bonded moieties, include:

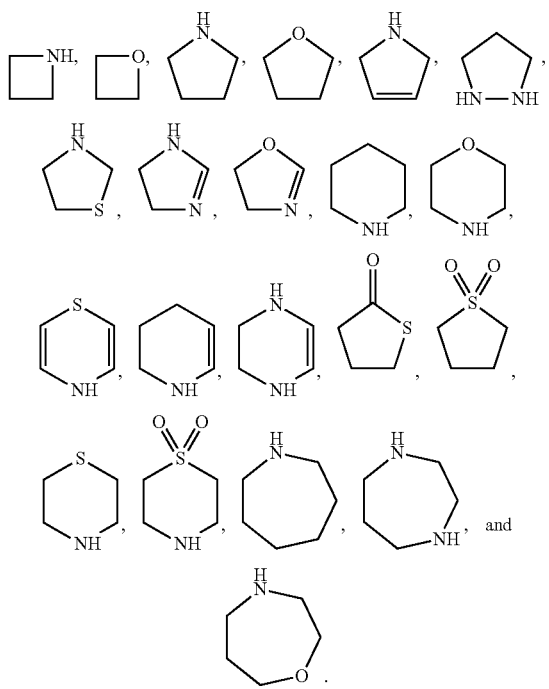

The term "aryl" refers to a monocyclic, or fused or spiro polycyclic, aromatic carbocycle (ring structure having ring atoms that are all carbon) having from 3 to 12 ring atoms per ring. (Carbon atoms in aryl groups are sp$^2$ hybridized.) Illustrative examples of aryl groups include the following moieties:

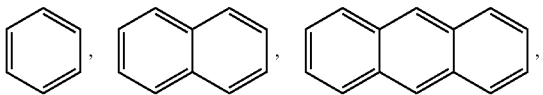

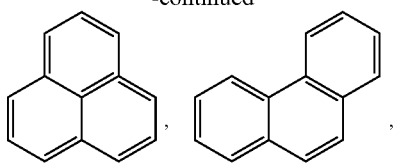

and the like.

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

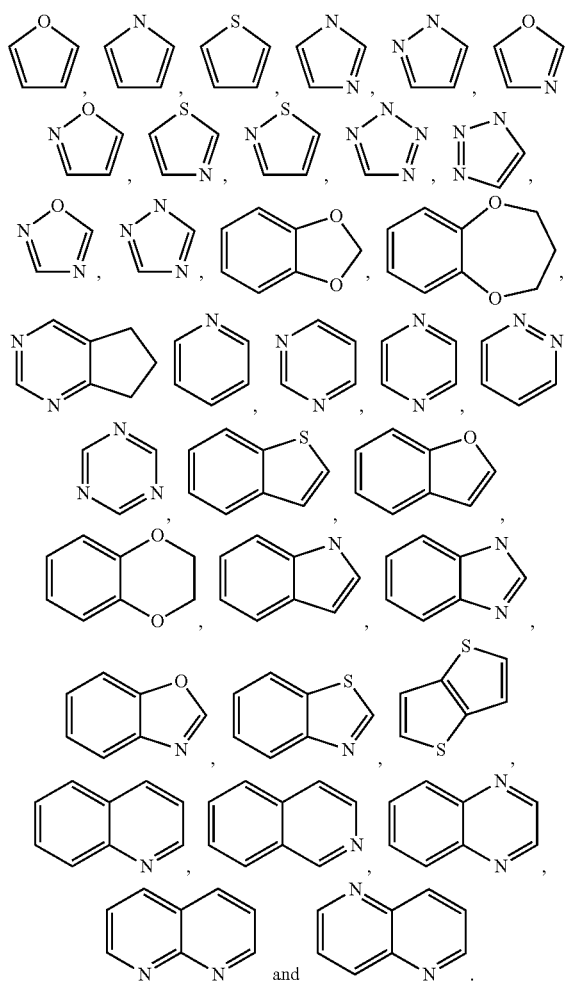

Those skilled in the art will recognize that the species of heteroaryl, cycloalkyl, aryl and heterocycloalkyl groups listed or illustrated above are not exhaustive, and that additional species within the scope of these defined terms may also be selected.

The term "halogen" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

The terms "para", "meta", and "ortho" have the meanings as understood in the art. Thus, for example, a fully substituted phenyl group has substituents at both "ortho" (o) positions adjacent to the point of attachment of the phenyl ring, both "meta" (m) positions, and the one "para" (p) position across from the point of attachment as illustrated below.

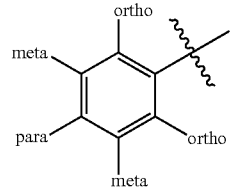

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

The terms "buffered" solution or "buffer" solution are used herein interchangeably according to their standard meaning. Buffered solutions are used to control the pH of a medium, and their choice, use, and function is known to those of ordinary skill in the art. See, for example, G. D. Considine, ed., *Van Nostrand's Encyclopedia of Chemistry*, p. 261, 5$^{th}$ ed. (2005), describing, inter alia, buffer solutions and how the concentrations of the buffer constituents relate to the pH of the buffer. See also *Handbook of Chemistry and Physics*, 84$^{th}$ ed., pp. 8-37 to 8-44. For example, a buffered solution is obtained by adding $MgSO_4$ and $NaHCO_3$ to a solution in a 10:1 w/w ratio to maintain the pH of the solution at about 7.5.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

The symbols ▬ and ◥ are used as meaning the same spatial arrangement in chemical structures shown herein. Analogously, the symbols ⫲⫲⫲⫲⫲ and ⫶⫶⫶⫶⫶ are used as meaning the same spatial arrangement in chemical structures shown herein.

Additionally, any formula given herein is intended to refer also to hydrates, solvates, and polymorphs of such compounds, and mixtures thereof, even if such forms are not listed explicitly. Certain compounds of Formula (I) or Formula (II) or pharmaceutically acceptable salts of compounds of Formula (I) or Formula (II) may be obtained as solvates. Solvates include those formed from the interaction or complexation of compounds of the invention with one or more solvents, either in solution or as a solid or crystalline form. In some embodiments, the solvent is water and then the solvates are hydrates. In addition, certain crystalline forms of compounds of Formula (I) or Formula (II) or pharmaceutically acceptable salts of compounds of Formula (I) or Formula (II) may be obtained as co-crystals. In certain embodiments of the invention, compounds of Formula (I) or Formula (II) were obtained in a crystalline form. In other embodiments, crystalline forms of compounds of Formula (I) or Formula (II) were cubic in nature. In other embodiments, pharmaceutically acceptable salts of compounds of Formula (I) or Formula (II) were obtained in a crystalline form. In still other embodiments, compounds of Formula (I) or Formula (II) were obtained in one of several polymorphic forms, as a mixture of crystalline forms, as a polymorphic form, or as an amorphous form. In other embodiments, compounds of Formula (I) or Formula (II) convert in solution between one or more crystalline forms and/or polymorphic forms.

Reference to a chemical entity herein stands for a reference to any one of: (a) the actually recited form of such chemical entity, and (b) any of the forms of such chemical entity in the medium in which the compound is being considered when named. For example, reference herein to a compound such as R—COOH, encompasses reference to any one of, for example, R—COOH$_{(s)}$, R—COOH$_{(sol)}$, and R—COO$^-_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^-_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH$_{(aq)}$ and/or R—COO$^-_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI:27369 by the Chemical Entities of Biological Inerest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula H$_2$NCH$_2$COOH, and it exists in some media (in this case in neutral media) in the form of the zwitterion $^+$H$_3$NCH$_2$COO$^-$. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorus, fluorine, and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, $^{125}$I, respectively. Such isotopically labeled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or an I$^{123}$ for SPECT studies. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S^1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$" is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as $R^1$, $R^2$, $R^3$, $R^4$, A, $R^a$, $R^b$, $R^c$, $R^d$, $R^e$, $R^f$, $R^g$, $R^h$, $R^i$, $R^j$, and $R^k$, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^1$, $R^2$, $R^3$, $R^4$, A, $R^a$, $R^b$, $R^c$, $R^d$, $R^e$, $R^f$, $R^g$, $R^h$, $R^i$, $R^j$, and $R^k$, and any other generic substituent symbol used herein.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with a total number N of carbon members in the chain that satisfies n≤N≤m, with m>n. Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

In certain embodiments of compounds of Formula (I), n is 0.

In certain embodiments of compounds of Formula (I), n is 1.

In certain embodiments of compounds of Formula (I), $R^1$ is phenyl substituted with $R^a$, where $R^a$ is a member selected from the group consisting of: —H, —F, —$C_{1-4}$alkoxy, and —$CH_3$, and $R^b$ is a member selected from the group consisting of: —Br, —$OCH_3$, thiophen-2-yl, 2H-1,2,3-triazole, 1H-1,2,3-triazol-1-yl, 1H-pyrazol-1-yl, 1H-pyrazol-5-yl, pyrimidin-2-yl, 3-methyl-1,2,4-oxadiazol-5-yl, and phenyl.

In certain embodiments of compounds of Formula (I), $R^a$ is a member selected from the group consisting of: —H, —F, —$OCH_3$, and —$CH_3$ In certain embodiments of compounds of Formula (I), $R^1$ is (2-fluoro-phenyl)-2-methyl-thiazol-4-yl.

In certain embodiments of compounds of Formula (I), $R^1$ is biphenyl-2-yl, 2-thiophen-2-yl-phenyl, 2-bromophenyl, 2,6-dimethoxy-phenyl, 2-(3-methyl-1,2,4-oxadiazol-5-yl)phenyl, 2-[1,2,3]triazol-2-yl-phenyl, 3-fluoro-2-[1,2,3]triazol-2-yl-phenyl, 2-fluoro-6-[1,2,3]triazol-2-yl-phenyl, 3-fluoro-2-(1H-1,2,3-triazol-1-yl)phenyl, 3-methoxy-2-(1H-1,2,3-triazol-1-yl)phenyl, 3-methyl-2-(1H-1,2,3-triazol-1-yl)phenyl, 2-fluoro-6-(2H-1,2,3-triazol-2-yl)phenyl, 3-fluoro-2-(2H-1,2,3-triazol-2-yl)phenyl, 3-methoxy-2-(2H-1,2,3-triazol-2-yl)phenyl, 4-methoxy-2-(2H-1,2,3-triazol-2-yl)phenyl, 5-methoxy-2-(2H-1,2,3-triazol-2-yl)phenyl, 5-fluoro-2-(2H-1,2,3-triazol-2-yl)phenyl, 3-fluoro-2-(1H-pyrazol-1-yl)phenyl, 3-fluoro-2-(1H-pyrazol-5-yl)phenyl, 3-methyl-2-(1H-pyrazol-1-yl)phenyl, 3-fluoro-2-pyrimidin-2-ylphenyl, 4-fluoro-2-(pyrimidin-2-yl)phenyl, or 5-fluoro-2-pyrimidin-2-yl-phenyl.

In certain embodiments of compounds of Formula (I), $R^1$ is 6-methyl-2-(1H-1,2,3-triazol-1-yl)pyridin-3-yl.

In certain embodiments of compounds of Formula (I), $R^2$ is pyrazine or pyrimidine, substituted or unsubstituted with one or more members selected from the group consisting of: —$C_{1-4}$alkyl, —$OCH_3$, —$CF_3$, —Cl, —F, —$N(CH_3)_2$, —$NH_2$, and phenyl.

In certain embodiments of compounds of Formula (I), $R^2$ is 2-methylpyrimidin-4-amine, 2-phenylpyrimidin-4-yl, 4-(trifluoromethyl)pyrimidin-2-yl, 4,5,6-trimethylpyrimidin-2-yl, 4,5-dimethylpyrimidin-2-yl, 4,6-dimethoxypyrimidin-2-yl, 4,6-dimethyl-pyrimidin-2-yl, 4-amino-6-methylpyrimidin-2-yl, 4-methoxy-pyrimidin-2-yl, 4-methyl-6-trifluoromethyl-pyrimidin-2-yl, 4-methylpyrimidin-2-yl, 4-phenyl-pyrimidin-2-yl, 5-chloro-4,6-dimethylpyrimidin-2-yl, 5-chloro-4-methylpyrimidin-2-yl, 5-fluoro-4,6-dimethylpyrimidin-2-yl, 5-fluoro-4-methylpyrimidin-2-yl, 6-(trifluoromethyl)pyrimidin-4-yl, 6-methyl-2-(1-methylethyl)pyrimidin-4-yl, N,N,2-trimethylpyrimidin-4-amine, N,N,6-trimethylpyrimidin-2-amine, N,N-dimethylpyrimidin-4-amine, pyrimidin-2-yl-4-amine, or 3,6-dimethylpyrazin-2-yl.

In certain embodiments of compounds of Formula (I), $R^2$ is pyridine substituted or unsubstituted with one or more members selected from the group consisting of: —$CH_3$ and —$CF_3$.

In certain embodiments of compounds of Formula (I), $R^2$ is 4-(trifluoromethyl)pyridin-2-yl, 4,6-dimethylpyridin-2-yl, 4-methylpyridin-2-yl, or 6-(trifluoromethyl)pyridin-2-yl.

In certain embodiments of compounds of Formula (I), $R^2$ is 2-methylquinoline, quinoline, or quinoxalin-2-yl.

In certain embodiments of compounds of Formula (I), $R^2$ is 6-chloro-1,3-benzoxazole or benzooxazol-2-yl.

In certain embodiments of compounds of Formula (I), $R^2$ is 2-methylpyrimidin-4-amine, 2-phenylpyrimidin-4-yl, 4-(trifluoromethyl)pyrimidin-2-yl, 4,5,6-trimethylpyrimidin-2-yl, 4,5-dimethylpyrimidin-2-yl, 4,6-dimethoxypyrimidin-2-yl, 4,6-dimethyl-pyrimidin-2-yl, 4-amino-6-methylpyrimidin-2-yl, 4-methoxy-pyrimidin-2-yl, 4-methyl-6-trifluoromethyl-pyrimidin-2-yl, 4-methylpyrimidin-2-yl, 4-phenyl-pyrimidin-2-yl, 5-chloro-4,6-dimethylpyrimidin-2-yl, 5-chloro-4-methylpyrimidin-2-yl, 5-fluoro-4,6-dimethylpyrimidin-2-yl, 5-fluoro-4-methylpyrimidin-2-yl, 6-(trifluoromethyl)pyrimidin-4-yl, 6-methyl-2-(1-methylethyl)pyrimidin-4-yl, N,N,2-trimethylpyrimidin-4-amine, N,N,6-trimethylpyrimidin-2-amine, N,N-dimethylpyrimidin-4-amine, pyrimidin-2-yl-4-amine, 4-methyl-6,7-dihydro-5H-cyclopenta[d]pyrimidine, 4-(trifluoromethyl)pyridin-2-yl, 4,6-dimethylpyridin-2-yl, 4-methylpyridin-2-yl, 6-(trifluoromethyl)pyridin-2-yl, 2-methylquinoline, quinoline, quinoxalin-2-yl, 6-chloro-1,3-benzoxazole or benzooxazol-2-yl.

In certain embodiments of compounds of Formula (I), $R^1$ is 2-(3-methyl-1,2,4-oxadiazol-5-yl)phenyl, 2-[1,2,3]triazol-2-yl-phenyl, 2-fluoro-6-[1,2,3]triazol-2-yl-phenyl, 2-fluoro-6-(2H-1,2,3-triazol-2-yl)phenyl, or 5-methoxy-2-(2H-1,2,3-triazol-2-yl)phenyl and $R^2$ is 4,5,6-trimethylpyrimidin-2-yl, 4,5-dimethylpyrimidin-2-yl, or 4,6-dimethyl-pyrimidin-2-yl.

In certain embodiments of compounds of Formula (II), $R^3$ is phenyl substituted —$CH_3$ and substituted in the ortho position with —$CH_3$.

In certain embodiments of compounds of Formula (II), $R^4$ is 2-phenylpyrimidin-4-yl or quinoxalin-2-yl.

Compounds of Formula (I) and Formula (II) and pharmaceutically acceptable salts thereof are used, alone or in combination with one or more additional active ingredients, to formulate pharmaceutical compositions. A pharmaceutical composition therefore comprises an effective amount of at least one a compound of Formula (I) and Formula (II) or a pharmaceutically acceptable salt thereof.

The invention includes also pharmaceutically acceptable salts of the compounds of Formula (I) and Formula (II), preferably of those described above and of the specific compounds exemplified herein, and methods of treatment using such salts.

A "pharmaceutically acceptable salt" is intended to mean a salt of a free acid or base of a compound represented by Formula (I) and Formula (II), that is non-toxic, biologically tolerable, or otherwise biologically suitable for administration to the subject. See, generally, G. S. Paulekuhn, et al., "Trends in Active Pharmaceutical Ingredient Salt Selection based on Analysis of the Orange Book Database", *J. Med. Chem.*, 2007, 50:6665-72, S. M. Berge, et al., "Pharmaceutical Salts", *J Pharm Sci.*, 1977, 66:1-19, and *Handbook of Pharmaceutical Salts, Properties, Selection, and Use*, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I) and Formula (II) may possess a sufficiently acidic group, a sufficiently basic group, or both types of functional groups, and accordingly react with a number of inorganic or organic bases, and inorganic and organic acids, to form a pharmaceutically acceptable salt.

bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methyl benzoates, dinitrobenzoates, hydroxybenzoates, methoxybenzoates, phthalates, sulfonates, xylenesulfonates, phenylacetates, phenylpropionates, phenyl butyrates, citrates, lactates, γ-hydroxybutyrates, glycolates, tartrates, methane-sulfonates, propanesulfonates, naphthalene-1-sulfonates, naphthalene-2-sulfonates, and mandelates.

When the compound of Formula (I) or Formula (II) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) or Formula (II) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-D-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Formula (I) and Formula (II), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I) or Formula (II)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "*Design of Prodrugs*", ed. H. Bundgaard, Elsevier, 1985.

Exemplary prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I) or Formula (II). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) or Formula (II), as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al, *J Med. Chem.* 1996, 39 (1), 10-18. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds of Formula (I) or Formula (II), which may also be used in the methods of the invention. A "pharmaceutically active metabolite" means a pharmacologically active product of metabolism in the body of a compound of Formula (I) or Formula (II) or salt thereof. Prodrugs and active metabolites of a compound may be determined using routine techniques known or available in the art. See, e.g., Bertolini, et al., *J Med. Chem.* 1997, 40, 2011-2016; Shan, et al., *J Pharm Sci.* 1997, 86 (7), 765-767; Bagshawe, *Drug Dev Res.* 1995, 34, 220-230; Bodor, *Adv Drug Res.* 1984, 13, 224-331; Bundgaard, Design of Prodrugs (Elsevier Press, 1985); and Larsen, *Design and Application of Prodrugs, Drug Design and Development* (Krogsgaard-Larsen, et al., eds., Harwood Academic Publishers, 1991).

The compounds of Formula (I) or Formula (II) and their pharmaceutically acceptable salts, pharmaceutically acceptable prodrugs, and pharmaceutically active metabolites of the present invention are useful as modulators of the orexin receptor in the methods of the invention. As such modulators, the compounds may act as antagonists, agonists, or inverse agonists. The term "modulators" include both inhibitors and activators, where "inhibitors" refer to compounds that decrease, prevent, inactivate, desensitize or down-regulate orexin receptor expression or activity, and "activators" are compounds that increase, activate, facilitate, sensitize, or up-regulate orexin receptor expression or activity.

The term "treat" or "treating" as used herein is intended to refer to administration of an active agent or composition of the invention to a subject for the purpose of effecting a therapeutic or prophylactic benefit through modulation of orexin receptor activity. Treating includes reversing, ameliorating, alleviating, inhibiting the progress of, lessening the severity of, or preventing a disease, disorder, or condition, or one or more symptoms of such disease, disorder or condition mediated through modulation of orexin receptor activity. The term "subject" refers to a mammalian patient in need of such treatment, such as a human.

Accordingly, the invention relates to methods of using the compounds described herein to treat subjects diagnosed with or suffering from a disease, disorder, or condition mediated by orexin receptor activity, such as: disorders of the sleep-wake cycle, metabolic disorders, neurological disorders and other disorders (e.g., feeding, drinking, arousal, stress, addiction, metabolism and reproduction). Symptoms or disease states are intended to be included within the scope of "medical conditions, disorders, or diseases."

Sleep disorders include, but are not limited to, sleep-wake transition disorders, insomnia, restless legs syndrome, jet-lag, disturbed sleep, and sleep disorders secondary to neurological disorders (e.g., manias, depressions, manic depression, schizophrenia, and pain syndromes (e.g., fibromyalgia, neuropathic pain).

Metabolic disorders include, but are not limited to, overweight or obesity and conditions related to overweight or obesity, such as insulin resistance, type II diabetes, hyperlipidemia, gallstones, angina, hypertension, breathlessness, tachycardia, infertility, sleep apnea, back and joint pain, varicose veins and osteoarthritis.

Neurological disorders include, but are not limited to, Parkinson's disease, Alzheimer's disease, Tourette's Syndrome, catatonia, anxiety, delirium and dementias.

Other disorders include, but are not limited to, ulcers, irritable bowel syndrome, diarrhea and gastroesophageal reflux.

In treatment methods according to the invention, an effective amount of a pharmaceutical agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the active agents of the invention may be used in combination with additional active ingredients in the treatment of the above conditions. The additional active ingredients may be coadministered separately with an active agent of compounds of Table 1 or included with such an agent in a pharmaceutical composition according to the invention. In an exemplary embodiment, additional active ingredients are those that are known or discovered to be effective in the treatment of conditions, disorders, or diseases mediated by orexin activity, such as another orexin modulator or a compound active against another target associated with the particular condition, disorder, or disease. The combination may serve to increase efficacy (e.g., by including in the combination a compound potentiating the potency or effectiveness of an active agent according to the invention), decrease one or more side effects, or decrease the required dose of the active agent according to the invention.

The active agents of the invention are used, alone or in combination with one or more additional active ingredients, to formulate pharmaceutical compositions of the invention. A pharmaceutical composition of the invention comprises: (a) an effective amount of at least one active agent in accordance with the invention; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily. For example, a total daily dosage of about 5 mg to 5 g daily may be accomplished by dosing once, twice, three, or four times per day.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semi-solid, or liquid diluent. Soft gelatin capsules may be prepared by mixing the compound of the invention with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 µg/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery.

Compounds of the invention may alternatively be administered in methods of this invention by inhalation, via the nasal or oral routes, e.g., in a spray formulation also containing a suitable carrier.

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Abbreviations and acronyms used herein include the following:

| Term | Acronym |
| --- | --- |
| High-performance liquid chromatography | HPLC |
| Thin layer chromatography | TLC |
| Diisopropylethylamine | DIPEA |
| Tetrahydrofuran | THF |
| tert-Butylcarbamoyl | BOC |
| Carboxybenzyl | Cbz |
| Dichloromethane | DCM |
| Trifluoroacetic acid | TFA |
| Acetic Acid | HOAc |
| N,N-Dimethylformamide | DMF |
| Methanol | MeOH |
| Ethanol | EtOH |
| Acetonitrile | CAN |
| Ethyl Acetate | EtOAc, or EA |
| Triethylamine | TEA |
| Methanesulfonyl chloride | MsCl |
| 2-(1H-9-Azobenzotriazole-1-yl)-1,1,3,3-tetramethylaminium hexafluorophosphate | HATU |
| 1-Hydroxy-7-azabenzotriazole | HOAT |
| Methyl Tertiary Butyl Ether | MTBE |
| N-(3-Dimethylaminopropyl)-N-ethylcarbodiimide | EDCl |
| [1,1'-Bis(diphenylphosphino)ferrocene]palladium (II) Dichloride Dichloromethane Adduct | PdCl$_2$(dppf)-dcm adduct |

SCHEME A

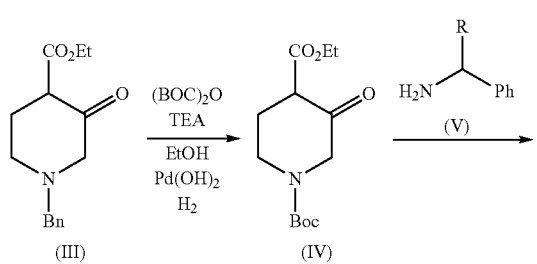

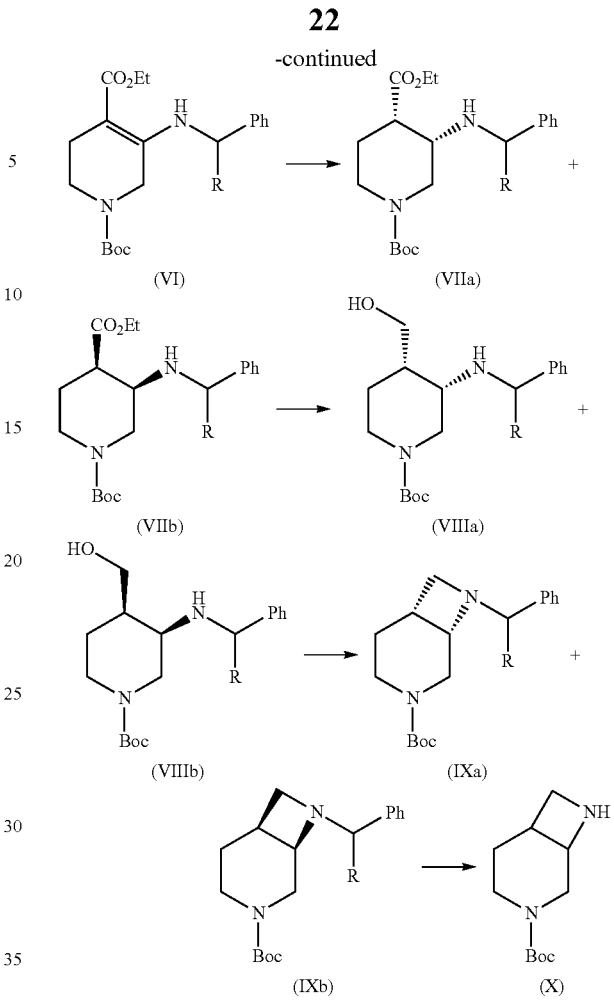

According to Scheme A, compound (IV) is obtained from treating compound (III), with hydrogen gas, di-tert-butyl dicarbonate (BOC$_2$O), in the presence of a Pd catalyst and a tertiary amine base in a suitable solvent such as ethanol. In a particularly preferred embodiment the Pd catalyst is Pd(OH)$_2$ on carbon (20% on dry basis-Pearlman's catalyst), the tertiary amine base is triethylamine, and the solvent is EtOH. The enamine compound of formula (VI) where R is H, is obtained by reacting a compound of formula (IV) with commercially available benzylamine (V), in a solvent such as toluene and the like, employing a Dean-Stark trap apparatus for the removal of water, at temperatures ranging from 115° C. to 125° C. Alternatively, the enamine compound of formula (VI), where R is —CH$_3$, is obtained by reacting a compound of formula (IV) with commercially available (S)-α-methylbenzylamine or (R)-α-methylbenzylamine as described in Frost et al., *J. Med Chem*, 2006, 49, Pgs 7843-53. Compounds of formula (VIIa) and (VIIb) are obtained by reduction of the double bond in a compound of formula (VI), with a reducing agent such as sodium triacetoxyborohydride, and the like, in a solvent such as toluene, with or without the presence of a drying agent such as molecular sieves and acetic acid, at temperatures ranging from 0° C. to ambient temperature. Compounds of formula (VIIIa) and (VIIIb) are obtained by reduction of the ester moiety in compounds of formula (VIIa) and (VIIb) with a reducing agent such as lithium aluminum hydride, and the like, in a solvent such as THF, at 0° C. Compounds of formula (IXa) and (IXb) are obtained by activation of the alcohol with a suitable activating agent such as MsCl, in a solvent such as DCM or THF at temperatures ranging from 0° C. to 23° C. in the presence of a suitable base such as triethylamine followed by heating the mixture to temperatures ranging from 35° C. to 60° C. in the presence of a suitable base such as cesium carbonate for 1 to 24 h. Compound (X) is obtained by treating compounds of formula (IXa) and (IXb) with hydrogen in the presence of a solvent, preferably an alcoholic solvent such as ethanol at hydrogen pressures from 1 atm to 50 psi at temperatures ranging from 23° C. to 50° C., preferably at 50° C. Alternatively, compound (X) is obtained by treating compounds of formula (IXa) and (IXb) with hydrogen generated using a continous flow hydrogenation apparatus (ThalesNano H-cube apparatus) in the presence of a solvent, preferably ethyl acetate, acetic acid or an alcoholic solvent such as ethanol optionally in the presence of an acid such as HCl or HOAc at hydrogen pressures from 10 to 100 bar at temperatures ranging from 23° C. to 100° C., preferably at 23-50° C. The (3R,4R)-isomer or the (3S,4S)-isomer of compounds of formula (IXa) and (IXb) are prepared as described in Frost et al., *J. Med Chem,* 2006, 49, Pgs 7843-53.

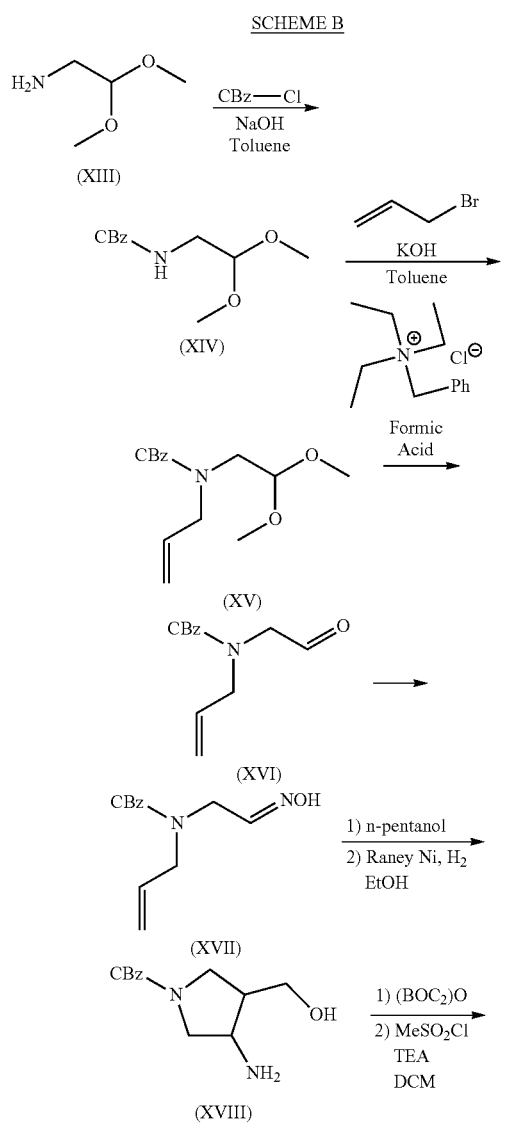

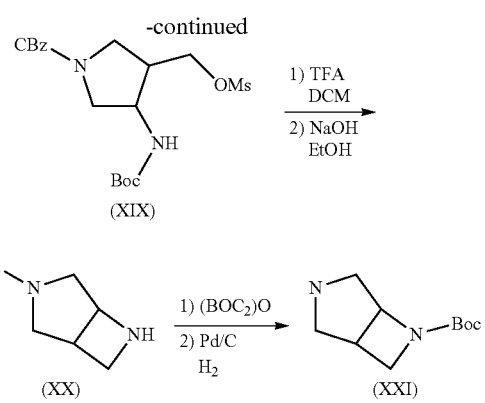

According to SCHEME B, compound (XIV) is obtained by reaction of compound (XIII) with benzyl chloroformate in a solvent such as toluene at temperatures ranging from 0° C. to 23° C., preferably 0° C. for a period of 1 to 8 hours, preferably about 4 h. Compound (XV) is obtained from compound (XIV) by reaction with allyl bromide in the presence of a base, preferably sodium or potassium hydroxide, in a solvent such as toluene, in the presence of a tetra alkyl ammonium chloride such as triethylbenzyl ammonium chloride at temperatures ranging from 23° C. to 100° C., preferably about 50° C. for a period of from 1 to 4 days, preferably about 2 days. Compound (XVI) is obtained from compound (XV) by reaction with an acid, preferably formic acid. Compound (XVII) is obtained from compound (XVI) by reaction with hydroxylamine hydrochloride in a solvent such as acetonitrile in the presence of a suitable base agent such as sodium acetate trihydrate for a period ranging from 12 to 24 hours. Compound (XVIII) is obtained from compound (XVII) by heating the compound (XVII) in a solvent such as pentanol at temperatures ranging from 100° C. to 150° C., preferably at about 135° C., for 12 to 24 hours, preferably about 20 hours followed by reaction with hydrogen gas in the presence of a catalyst such as Raney Ni, in a solvent such as ethanol and pressures around 60 psi for 2 to 6 hours, preferably about 4 hours. Compound (XVIII) is then converted to compound (XIX) by treatment with di-tert-butyl dicarbonate (BOC₂O) in a mixed solvent such as pentanol/ethanol/water in the presence of a base such as sodium bicarbonate for a period of 12 to 24 hours, preferably about 15 hours. Following this procedure, the resulting boc protected material is treated with methanesulfonyl chloride in a solvent such as DCM in the presence of a base such as triethylamine (TEA) at temperatures ranging from 0° C. to 35° C., preferably around 0° C. to 23° C. for a period of 1 to 24 hours to provide compound (XIX). Compound (XIX) is converted to compound (XX) by reaction with an acid, preferably TFA in the presence of a solvent, preferably DCM for a period ranging from 4 to 24 hours, preferably about 20 hours followed by reaction with a base, preferably sodium hydroxide, in a solvent such as ethanol/water at temperatures ranging from 23° C. to 80° C., preferably about 60° C., for 1 to 4 hours. Compound (XXI) is obtained from compound (XX) by the addition of di-tert-butyl dicarbonate (BOC₂O) to the above mixture followed by treating the resulting boc protected intermediate with hydrogen in the presence of a catalyst such as palladium on carbon in a solvent such as methanol or ethanol at pressures ranging from 15 to 60 psi for a period of about 2 hours.

SCHEME C

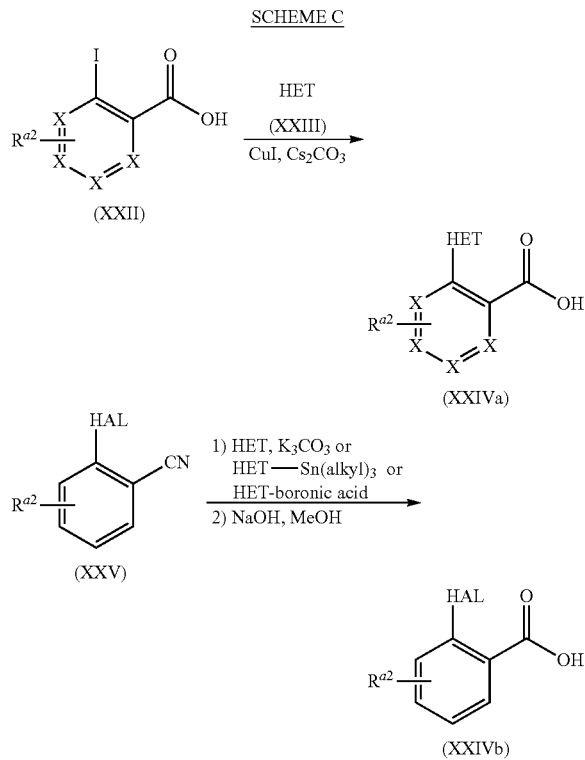

Intermediate compounds of formulae (XXIVa) and (XXIVb) are readily prepared as outlined in Scheme C from a commercially available or synthetically accessible compound of formula (XXII) or (XXV). Compounds of formula (XXIVa) are obtained by reacting a compound of formula (XXII), where $R^{a2}$ is —H, halo, —$C_{1-4}$alkyl, —$C_{1-4}$alkoxy, —$NO_2$, or two $R^{a2}$ members may come together to form a 6-membered aryl ring, where X is C or N (with the proviso that only one X member can be N), with commercially available HET compounds of formula (XXIII), where HET is 5-6 membered heteroaryl ring containing one to three nitrogen members, in the presence of copper(I)iodide, $Cs_2CO_3$ and N,N'-dimethylcyclohexane-1,2-diamine; in a solvent such as DMF or dioxane, at temperatures ranging from 60° C. to 100° C. (using conventional or microwave heating). One skilled in the art will recognize that 1,2,3-triazole can exist in two tautomeric forms defined as 2H-[1,2,3]triazole and 1H-[1,2,3]triazole thus accounting for the formation of two regioisomers.

Alternatively, compounds of formula (XXIVb) are prepared by the reaction of halobenzonitrile compounds of formula (XXV) with HET, where HET is a 5-membered heteroaryl ring selected from the group consisting of triazole or pyrazole, in a solvent such as DMF and the like, in the presence of an inorganic base such as $K_2CO_3$ and the like, at temperatures ranging from 100° C. to 130° C. Subsequent hydrolysis of the nitrile using a base such as aqueous NaOH and the like, in a solvent such as methanol provides compounds of formula (XXIVb).

Compounds of formula (XXIVb) are also prepared by the reaction of halobenzonitrile compounds of formula (XXV) with HET-Sn(alkyl)$_3$, where HET-Sn(alkyl)$_3$ is a commercially available or synthetically accessible trialkyltinheteroaryl compound, in a solvent such as DME, in the presence of a palladium catalyst such as Pd(PPh$_3$)$_4$, in the presence or absence of a catalytic amount of copper iodide, at temperatures ranging from 100° C. to 160° C., using conventional or microwave heating. Subsequent hydrolysis of the nitrile using a base such as aqueous NaOH and the like, in a solvent such as methanol provides compounds of formula (XXIVb).

Compounds of formula (XXIVb) are also prepared by the reaction of halobenzonitrile compounds of formula (XXV) with HET-boronic acid, where HET-boronic acid is a commercially available or synthetically accessible heteroarylboronic acid, in a solvent such as DME, in the presence of a base such as NaHCO$_3$, a palladium catalyst such as Pd(PPh$_3$)$_4$, at temperatures ranging from 80° C. to the reflux temperature of the solvent. Subsequent hydrolysis using a base such as aqueous NaOH and the like, in a solvent such as methanol provides compounds of formula (XXIVb).

SCHEME D

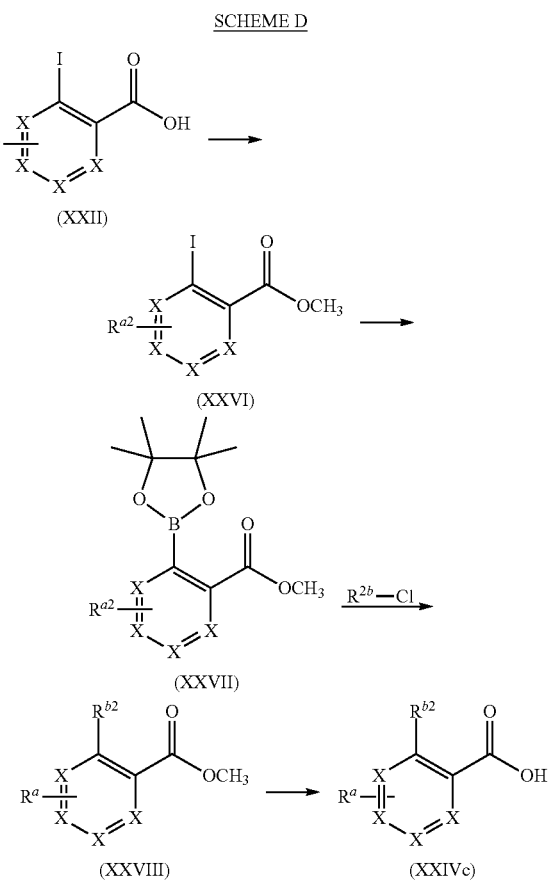

According to Scheme D, compounds of formula (XXIVc) are obtained from compounds of formula (XXII), by first converting a commercially available or synthetically accessible compound of formula (XXII), where $R^{a2}$ is —H, halo, —$C_{1-4}$alkyl, —$C_{1-4}$alkoxy, —$CF_3$, or —$NO_2$, and where X is C or N (with the proviso that only one X may be N) to one of formula (XXVI) under esterification conditions, for example by treating an alcohol solution of a compound of formula (XXII) with an acid. In a preferred method the compound of formula (XXII) is dissolved in a solvent such as MeOH and treated with $H_2SO_4$ to afford a compound of formula (XXVI). A compound of formula (XXVII) is obtained by reacting a suitable compound of formula (XXVI) with pinacol borane in the presence of a phosphine and a palladium catalyst, in the presence of an amine base, in a solvent such as THF, at temperatures ranging from room temperature to 70° C. In a preferred method the phosphine is tri(o-tolyl)phosphine, the palladium catalyst is Pd(OAc)$_2$ and the amine base is triethylamine.

A compound of formula (XXIVc) is obtained by reacting a compound of formula (XXVIII) with a compound R$^{b2}$—Cl, where R$^{b2}$—Cl is a suitable commercially available or synthetically accessible 6-membered chloro-substituted heteroaryl compound, in the presence of a palladium catalyst, a base such as Na$_2$CO$_3$, and the like, in a solvent such as 2-methyl-tetrahydrofuran (2-methyl-THF), and the like, at temperatures ranging from room temperature to 80° C. In a preferred method the palladium catalyst is PdCl$_2$(dppf)-dcm adduct, the base is Na$_2$CO$_3$ and the solvent is 2-methyl-THF. A compound of formula (XXIVc) is obtained from a compound of formula (XXVIII) via ester hydrolysis. In a preferred method of hydrolysis, a compound of formula (XXVIII) in methyl-THF is treated with aqueous NaOH to afford a compound of formula (XXIVc).

synthetically accessible compounds of formula (XXXIa) using a chlorinating agent such as oxalyl chloride and the like; in a solvent such as CH$_2$Cl$_2$, in the presence of a base such as N,N-dimethylaniline and the like; at temperatures ranging between room temperature and the reflux temperature of the solvent provides chloropyrimidines of formula (XXXIIa) or (XXXIIb). Additionally, chloropyrimidines of formula (XIV) are further elaborated. Chloropyrimidines of formula (XXXIIa) or (XXXIIb) are reacted with alkyl Grignard reagents (R$^g$MgBr); in the presence of a catalytic amount of Fe(acac)$_3$, in a solvent such as Et$_2$O at 0° C., provides alkyl chloropyrimidines of formula (XXXIIIa) or (XXXIIIb).

SCHEME E

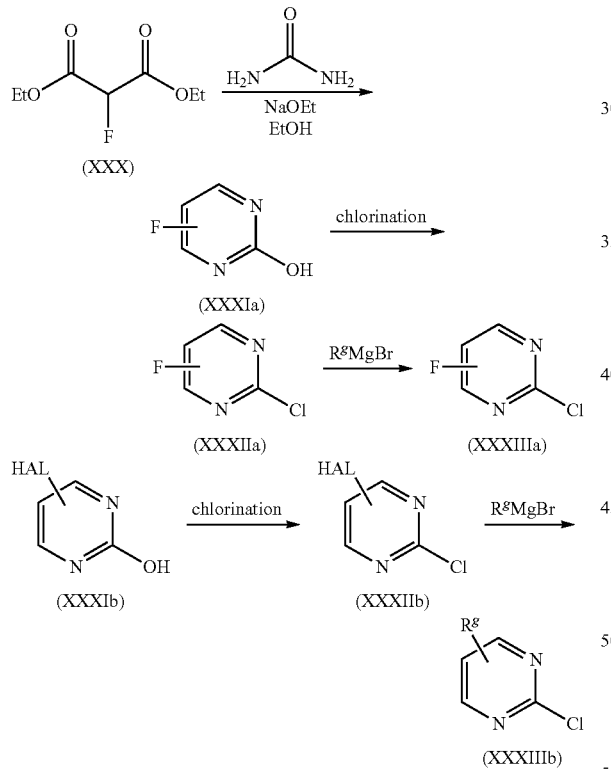

According to SCHEME E, substituted heteroaryl compounds R$^2$Cl of formula (XXXIIa) and (XXXIIIa) are prepared from commercially available or synthetically accessible compounds of formula (XXX). Pyrimidols of formula (XXXIa) and (XXXIb) are commercially available or are prepared by reacting substituted alkyl malonates of formula (XXX), where R$^e$ is halo, with urea in the presence of a base such as sodium ethoxide and the like; in a suitable solvent such as ethanol, at temperatures between room temperature and the reflux temperature of the solvent. Chlorination of commercially available pyrimidinols of formula (XXXIb) or

SCHEME F

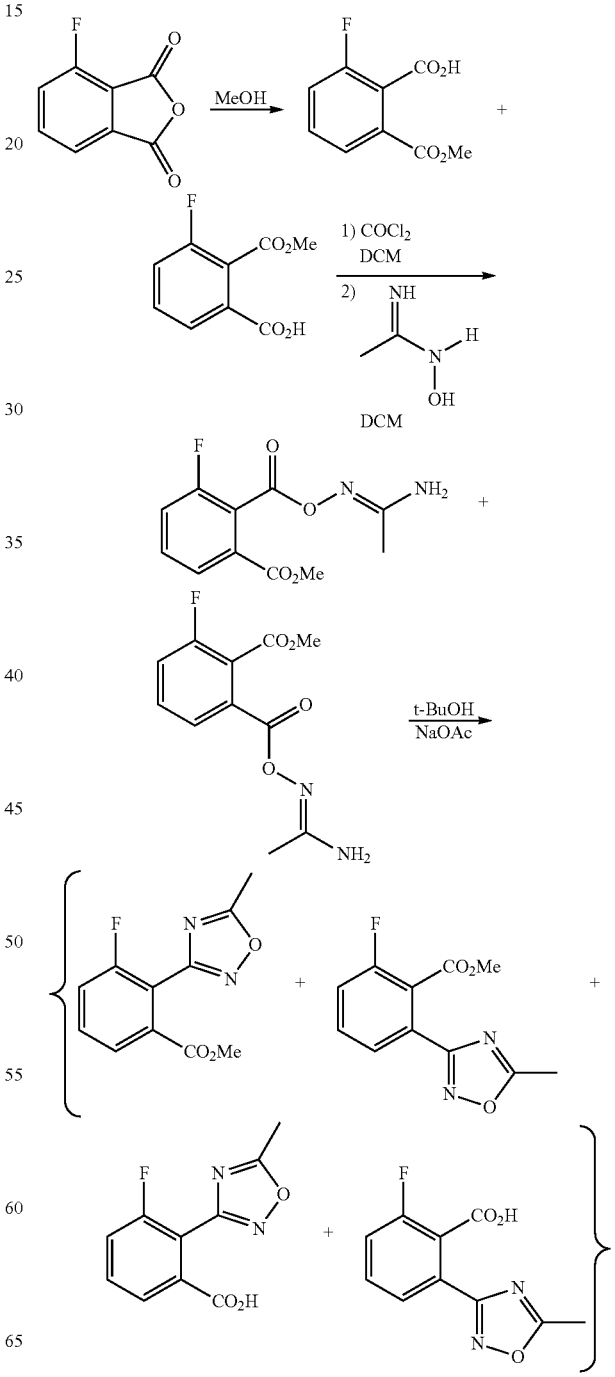

3-Fluoro-2-(3-methyl-1,2,4-oxadiazol-5-yl)benzoic acid and 2-fluoro-6-(3-methyl-1,2,4-oxadiazol-5-yl)benzoic acid are prepared according to SCHEME F. 3-Fluorophthalic anhydride was dissolved in a solvent such as MeOH, at temperatures ranging from room temperature to the reflux temperature of the solvent, to provide acid-esters (XXXVIa) and (XXXVIb). Conversion of the acid to the acid chloride is accomplished under standard chlorination conditions. In a preferred method the acid is heated with oxalyl chloride in a solvent such as DCM. Subsequent reaction of the acid chloride with N-hydroxyacetamide in a solvent such as $CH_2Cl_2$ provides a mixture of esters (XXXVIIa) and (XXXVIIb). Finally, esters (XXXVIIa) and (XXXVIIb) are converted to a mixtue of esters (XXXVIIIa) and (XXXVIIIb) and acids (XXXIXa) and (XXXIXb) by treatment with a base, preferably sodium acetate, in the presence of a solvent, preferably t-BuOH.

Alternately, acid (XXXIXa) is prepared by first converting 2-fluoro-6-iodobenzoic acid to the acid chloride by reaction with a chlorinating agent such as oxalyl chloride, in a solvent such as DCM, with a catalytic amount of DMF, at a temperature of 0° C. Subsequent reaction of the acid chloride with N-hydroxyacetamide in a solvent such as $CH_2Cl_2$ provides (Z)—N'-((2-fluoro-6-iodobenzoyl)oxy)acetimidamide. 5-(2-Fluoro-6-iodophenyl)-3-methyl-1,2,4-oxadiazole is prepared by reacting (Z)—N'-((2-fluoro-6-iodobenzoyl)oxy) acetimidamide with sodium acetate, in a solvent such as tert-butanol, at temperatures ranging from 100° C. to 110° C. 3-Fluoro-2-(3-methyl-1,2,4-oxadiazol-5-yl)benzoic acid (XXXIXa) is prepared by reacting 5-(2-fluoro-6-iodophenyl)-3-methyl-1,2,4-oxadiazole with a grignard reagent such as i-PrMgCl, in a suitable solvent such as THF and the like, at a temperature of −78° C. Subsequent addition of $CO_2$ gas, at a temperature of −78° C. provides 3-fluoro-2-(3-methyl-1,2,4-oxadiazol-5-yl)benzoic acid (XXXIXa).

SCHEME G

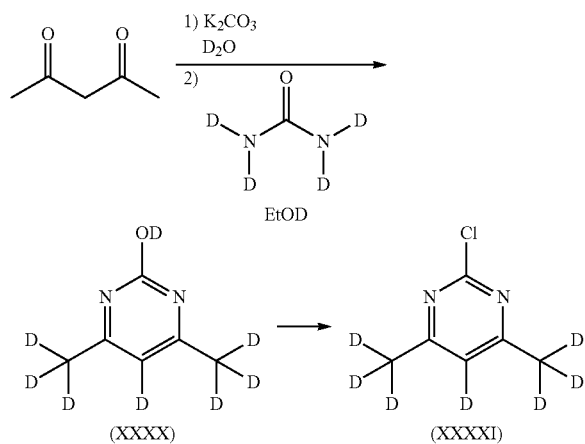

Deuterated pyrimidine compounds of formula (XXXXI) are prepared according to Scheme G. Acetylacetone is reacted with an inorganic base such as $K_2CO_3$ in deuterated water, at temperatures ranging from 100° C. to 120° C. to provide 1,1,1,3,3,3,5,5-octadeuteriopentane-2,4-dione. 1,1,1,3,3,3,5,5-Octadeuteriopentane-2,4-dione is subsequently reacted with deuterated urea, in a solvent such as deuterated ethanol, 35% wt. DCl in $D_2O$, at temperatures ranging from 90° C. to 100° C. to provide deuterated pyrimidinols of formula (XXXX). Chlorination under standard chlorinating conditions provides chlorodetuteratedpyrimidine compounds of formula (XXXXI).

SCHEME H

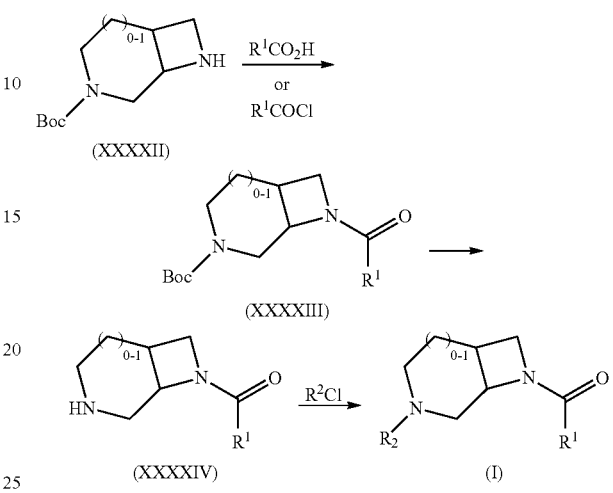

According to SCHEME H, a compound of formula (XXXXIII) is obtained from a compound of formula (XXXXII), by reaction of a compound of formula (XXXXII) with a compound of formula $R^1CO_2H$ under amide formation conditions. Compounds of formula $R^1CO_2H$, where $R^1$ is as defined in formula (I), are commercially available, as described, or synthetically accessible appropriately substituted aryl or heteroaryl carboxylic acids. In a preferred embodiment a compound of formula (XXXXII), either as a free base or as an acid salt, is reacted with a compound of formula $R^1CO_2H$ in the presence of a dehydrating agent such as HOBt/EDAC, CU, HATU, HOAT, BOP; a suitably selected base such as DIPEA, TEA, and the like; in an organic solvent or mixture thereof, such as toluene, acetonitrile, ethyl acetate, DMF, THF, methylene chloride, and the like; to afford a compound of formula (XXXXIII). In a particularly preferred embodiment the dehydrating agent is HATU, and the base is DIPEA.

In an alternative embodiment, a compound of formula $R^1CO_2H$ (as described above) may be first converted to a compound of formula $R^1COCl$ with a chlorinating agent such as oxalyl chloride or thionyl chloride in a solvent such as $CH_2Cl_2$ and the like optionally in the presence of DMF or compound of formula $R^1COCl$ is a commercially available substituted aryl sulfonyl chloride. In a preferred embodiment, a compound of formula $R^1CO_2H$ is treated with thionyl chloride in a solvent such as toluene to afford a compound of formula $R^1COCl$. A compound of formula (XXXXIII) is obtained by treating a compound of formula (XXXXII) with a compound of formula $R^1COCl$, a suitably selected tertiary organic base such as TEA, and the like, in a solvent such as dichloromethane, THF, and the like, at a temperature between room temperature and the reflux temperature of the solvent.

Removal of the tert-butylcarbamate (boc) in compounds of formula (XXXXIII) is accomplished by using methods known to one skilled in the art, such as, HCl, TFA, or p-toluenesulfonic acid, in a solvent such as $CH_3OH$, dioxane, or $CH_2Cl_2$. In a preferred embodiment, a compound of formula (XXXXIII) is treated with TFA in DCM or HCl to afford a compound of formula (XXXXIV).

A compound of formula (I) is obtained by treating a compound of formula (XXXXIV) with $R^2Cl$, where $R^2$ is as defined in formula (I). Commercially available or synthetically accessible suitably substituted heteroaryl compounds of formula $R^2Cl$ are reacted with compounds of formula (XXXXIV) in the presence of a suitably selected tertiary organic or inorganic base such as $Cs_2CO_3$, $Na_2CO_3$, TEA, DIPEA and the like; in a solvent such as DMF, dichloromethane, THF, acetonitrile and the like; using conventional heating or microwave heating at a temperatures between room temperature and 200° C. to provide compounds of formula (I). In a preferred embodiment the base is $Cs_2CO_3$ and the solvent is DMF.

SCHEME I

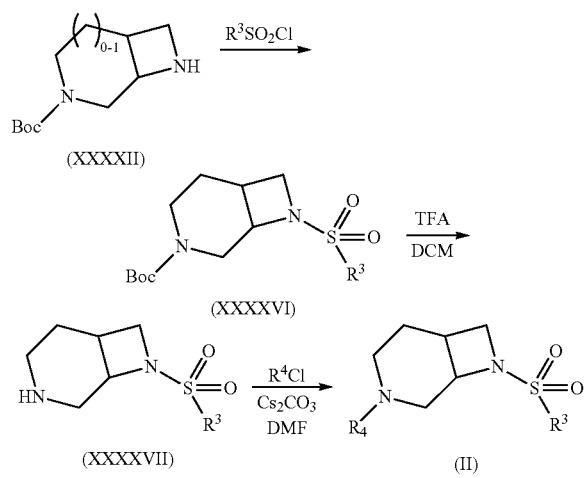

A compound of formula (II) is obtained by treating a commercially available aryl sulfonyl chloride compound of formula $R^3SO_2Cl$, wherein $R^3$ is as defined in formula (II), with compound (XXXXII), in the presence of a tertiary organic base such as TEA, and the like, in a solvent such as dichloromethane, THF, and the like, at a temperature between room temperature and the reflux temperature of the solvent. Removal of the tert-butylcarbamate (boc) in a compound of formula (XXXXVI) is accomplished by using methods known to one skilled in the art, such as, HCl, TFA, or p-toluenesulfonic acid, in a solvent such as $CH_3OH$, dioxane, or $CH_2Cl_2$. In a preferred embodiment, a compound of formula (XXXXVI) is treated with TFA in DCM or HCl to afford a compound of formula (XXXXVII). A compound of formula (II) is obtained by treating a compound of formula (XXXXVII) with a commercially available or synthetically accessible substituted heteroaryl of formula $R^4Cl$, where $R^4$ is as defined in formula (II), in the presence of a suitably selected tertiary organic or inorganic base such as $Cs_2CO_3$, $Na_2CO_3$, TEA, and the like; in a solvent such as DMF, dichloromethane, THF, and the like; at a temperature between room temperature and the reflux temperature of the solvent. In a preferred embodiment the base is $Cs_2CO_3$ and the solvent is DMF.

Compounds of formula (I) or formula (II) may be converted to their corresponding salts using methods known to those skilled in the art. For example, amines of formula (I) or formula (II) may be treated with trifluoroacetic acid (TFA), HCl, maleic acid, or citric acid in a solvent such as diethyl ether ($Et_2O$), $CH_2Cl_2$, tetrahydrofuran (THF), or methanol (MeOH) to provide the corresponding salt forms.

Compounds prepared according to the schemes described above may be obtained as single enantiomers, diastereomers, or regioisomers, by enantio-, diastero-, or regiospecific synthesis, or by resolution. Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Compounds prepared according to the schemes above may alternately be obtained as racemic (1:1) or non-racemic (not 1:1) mixtures or as mixtures of diastereomers or regioisomers. Where racemic and non-racemic mixtures of enantiomers are obtained, single enantiomers may be isolated using conventional separation methods known to one skilled in the art, such as chiral chromatography, recrystallization, diastereomeric salt formation, derivatization into diastereomeric adducts, biotransformation, or enzymatic transformation. Where regioisomeric or diastereomeric mixtures are obtained, single isomers may be separated using conventional methods such as chromatography or crystallization.

The following examples are provided to further illustrate the invention and various preferred embodiments.

EXAMPLES

Chemistry

In obtaining the compounds described in the examples below and the corresponding analytical data, the following experimental and analytical protocols were followed unless otherwise indicated.

Unless otherwise stated, reaction mixtures were magnetically stirred at room temperature (rt) under a nitrogen atmosphere. Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure. Reactions under microwave irradiation conditions were carried out in a Biotage Initiator or CEM Discover instrument.

Normal-phase flash column chromatography (FCC) was performed on silica gel ($SiO_2$) using prepackaged cartridges, eluting with the indicated solvents.

Preparative reverse-phase high performance liquid chromatography (HPLC) was performed on a Gilson HPLC with an Xterra Prep $RP_{18}$ (5 μm, 30×100 mm, or 50×150 mm) column, and a gradient of 10 to 99% acetonitrile/water (20 mM $NH_4OH$) over 12 to 18 min, and a flow rate of 30 mL/min.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. The format of the $^1$H NMR data below is: chemical shift in ppm downfield of the tetramethylsilane reference (multiplicity, coupling constant J in Hz, integration).

Chemical names were generated using ChemDraw Ultra 6.0.2 (CambridgeSoft Corp., Cambridge, Mass.) or ACD/Name Version 9 (Advanced Chemistry Development, Toronto, Ontario, Canada).

Intermediate 1:
3,8-Diaza-bicyclo[4.2.0]octane-3-carboxylic acid tert-butyl ester

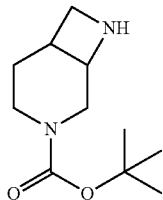

Step A. 3-Oxo-piperidine-1,4-dicarboxylic acid 1-tert-butyl ester 4-ethyl ester. A mixture of 1-benzyl-3-oxo-piperidine-4-carboxylic acid ethyl ester (11.31 g, 38 mmol), di-t-butyl dicarbonate (8.78 g, 40.2 mmol), Et$_3$N (5.4 mL, 38.7 mmol) and Pd(OH)$_2$ on carbon (20% on dry basis-Pearlman's catalyst) (1.3 g) were taken into EtOH (110 mL). The mixture was hydrogenated at 60 psi for 24 h in a Parr bottle. The catalyst was removed by filtration and the filtrate was concentrated to dryness to tan solid. Crude residue was shaken well with hexane (100 mL) and filtered. The filtrate was concentrated to yield the title compound (9.70 g, 94.25%). MS (ESI) mass calcd. for C$_{13}$H$_{21}$NO$_5$, 271.32; $^1$H NMR (400 MHz, CDCl$_3$) 4.24 (q, J=7.1, 2H), 4.03 (s br, 2H), 3.49 (t, J=5.6, 2H), 2.32 (m, 3H), 1.47 (s, 9H), 1.31 (t, J=7.1, 3H).

Step B. 5-Benzylamino-3,6-dihydro-2H-pyridine-1,4-dicarboxylic acid 1-tert-butyl ester 4-ethyl ester. 3-Oxo-piperidine-1,4-dicarboxylic acid 1-tert-butyl ester 4-ethyl ester (8.15 g, 30 mmol) from Step A and benzyl amine (3.43 g, 31.8 mmol) were dissolved into toluene (150 mL). The mixture was refluxed vigorously for 72 h and the generated water was collected into Dean-Stark apparatus. The residual solution was concentrated to yield the title compound (10.2 g, 92.5%). MS (ESI) mass calcd. for C$_{20}$H$_{28}$N$_2$O$_4$, 360.45, m/z found, 361.2 [M+H]$^+$. The crude product was carried to the next step without any purification.

Step C: 3-Benzylamino-piperidine-1,4-dicarboxylic acid 1-tert-butyl ester 4-ethyl ester. To a mixture of 5-benzylamino-3,6-dihydro-2H-pyridine-1,4-dicarboxylic acid 1-tert-butyl ester 4-ethyl ester (10.2 g, 28.9 mmol) in toluene (110 mL) was added NaBH(OAc)$_3$ (30 g, 141.5 mmol) and freshly activated 4A° powder molecular sieve (24 g) with vigorous stirring. The reaction mixture was cooled to 0° C., then acetic acid (32.5 mL, 566 mmol) was added drop-wise in such a way that reaction mixture temperature remained below 5° C. After the addition of acetic acid was complete, the mixture was allowed to warm to ambient temperature and stirred for 16 h. The reaction mixture was filtered and concentrated to remove most of the acetic acid. The crude residue was dissolved in ethyl acetate (125 mL) and saturated aqueous NaHCO$_3$ solution (100 mL) was slowly added to neutralize the residual acid under stirring. The layers were separated and the aqueous layer was extracted with ethyl acetate (2×100 mL). The combined organics were dried over Na$_2$SO$_4$, filtered, and concentrated under reduced pressure (11.25 g, crude). The residue was purified (FCC, SiO$_2$, ethyl acetate/hexanes, gradient 0-40%) to yield the title compound (4.59 g, 45%). MS (ESI) mass calcd. for C$_{20}$H$_{30}$N$_2$O$_2$, 362.46; m/z found, 363.3 [M+H]$^+$. $^1$H NMR (DMSO-d$_6$): 7.53-6.76 (m, 5H), 4.10-3.96 (m, 3H), 3.89-3.87 (m, 1H), 3.66 3.54 (m, 1H), 3.05-2.60 (m, 4H), 1.80-1.65 (m, 2H), 1.60-1.45 (m, 1H), 1.40 (s, 9H), 1.14 (t, J=7.1, 3H).

Step D: 3-Benzylamino-4-hydroxymethyl-piperidine-1-carboxylic acid tert-butyl ester. To a solution of LiAlH$_4$ (2M in THF, 14 mmol in 25 ml THF), cooled to 0° C., was slowly added a solution of 3-benzylamino-piperidine-1,4-dicarboxylic acid 1-tert-butyl ester 4-ethyl ester (4.53 g, 12.5 mmol) in THF (25 mL). The reaction mixture was stirred at 0° C. for 15 min and then at room temperature for 2 h. The reaction mixture was again cooled to 0° C. and quenched with Na$_2$SO$_4$, 10 H$_2$O and stirred for 16 h. The reaction mixture was filtered, washed with THF and concentrated to yield title compound (3.69 g, 92%). MS (ESI) mass calcd. for C$_{18}$H$_{28}$N$_2$O$_3$, 320.43; m/z found, 321.3 [M+H]$^+$. $^1$H NMR (CDCl$_3$): 7.42-7.19 (m, 5H), 5.64-4.97 (m, 1H), 4.57-4.0 (m, 1H), 3.99-3.82 (m, 2H), 3.79-3.56 (m, 3H), 3.04-2.58 (m, 3H), 1.95-1.79 (m, 2H), 1.74-1.55 (m, 2H), 1.47 (s, 9H).

Step E: 8-Benzyl-3,8-diaza-bicyclo[4.2.0]octane-3-carboxylic acid tert-butyl ester. To a cooled to 0° C. solution of 3-benzylamino-4-hydroxymethyl-piperidine-1-carboxylic acid tert-butyl ester (3.65 g, 11.4 mmol) and triethylamine (4.77 mL, 34.2 mmol) in THF (60 mL), was added drop-wise methane sulfonyl chloride (1.7 g, 14.8 mmol) at 0° C. The reaction mixture was warmed to room temperature and stirred for 1 h, then Cs$_2$CO$_3$ (5.0 g, 15.4 mmol) was added. The reaction mixture was heated to 60° C. for 18 h. The reaction mixture was cooled to ambient temperature and filtered. The filtrate was washed with H$_2$O (2×100 mL), the organic layer was separated and the aqueous layer was extracted with EtOAc (2×100 mL). The combined organics were dried (Na$_2$SO$_4$), filtered, and concentrated under reduced pressure to yield the crude title compound (3.38 g). The crude product was purified (FCC, SiO$_2$, 4% acetone, dichloromethane) to yield pure title compound (2.88 g, 84%). MS (ESI) mass calcd. for C$_{18}$H$_{26}$N$_2$O$_2$, 302.42; m/z found, 303.2 [M+H]$^+$. $^1$H NMR (CDCl$_3$): 7.35-7.15 (m, 5H), 4.02-2.80 (m, 9H), 2.48-2.36 (m, 1H), 1.95-1.65 (m, 2H), 1.56-1.32 (m, 10H).

Step F: 3,8-Diaza-bicyclo[4.2.0]octane-3-carboxylic acid tert-butyl ester. A mixture of 8-benzyl-3,8-diaza-bicyclo[4.2.0]octane-3-carboxylic acid tert-butyl ester (1.34 g, 4.44 mmol) and wet Pd(OH)$_2$/C (20 wt %, 938 mg) in EtOH (30 mL) was shaken under 60 psi atmosphere of H$_2$ for 2 days at 50° C. The reaction mixture was filtered and concentrated to give title compound (1.0 g, 94%). MS (ESI) mass calcd. for C$_{11}$H$_{20}$N$_2$O$_2$, 212.29; m/z found, 213.2 [M+H]$^+$. $^1$H NMR (CDCl$_3$): 4.32-4.0 (m, 1H), 3.93-3.17 (m, 5H), 3.10-2.70 (m, 3H), 1.98-1.67 (m, 2H), 1.56-1.36 (m, 9H).

Intermediate 2.
3,6-Diaza-bicyclo[3.2.0]heptane-6-carboxylic acid tert-butyl ester

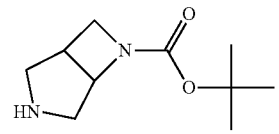

Step A. (2,2-Dimethoxy-ethyl)-carbamic acid benzyl ester. To a 500 mL round-bottomed flask equipped with temperature probe and nitrogen inlet were added aminoacetaldehyde dimethyl acetal (25 g, 238 mmol) in aq. NaOH (4.85 M, 69 mL) and toluene (125 mL). The mixture was cooled to 0° C. in an ice bath and benzylchloroformate (40.6 g, 238 mmol) was added at such a rate that the internal temperature was maintained below 20° C. The reaction mixture was stirred for 4 h at room temperature. The layers were separated, and the organic layer was washed with brine (2×20 mL), dried with sodium sulfate, filtered, and concentrated to a colorless oil (53.24 g, 93% yield). $^1$H-NMR (CDCl$_3$, 500 MHz): 7.30 (m, 5H), 5.11 (s, 2H), 4.37 (t, J=6.0 Hz, 1H), 3.39 (s, 6H), 3.33 (t, J=6.0 Hz, 2H). MS (electrospray): exact mass calculated for C$_{12}$H$_{17}$NO$_4$, 239.12; m/z found, 240 [M+H]$^+$.

Step B. Allyl-(2,2-dimethoxy-ethyl)-carbamic acid benzyl ester. To a 500 mL round-bottomed flask equipped with thermocouple probe, nitrogen inlet, reflux condenser, heating mantle, and mechanical stirring was added (2,2-dimethoxy-ethyl)-carbamic acid benzyl ester (50 g, 209 mmol) in toluene (180 mL). To the resulting solution was added powdered KOH (51.6 g, 920 mmol) and triethylbenzylammonium chloride (0.810 g, 3.55 mmol). A solution of allyl bromide (33.0 g, 275 mmol) in toluene (50 mL) was added dropwise over 10 minutes. The mixture was heated to 50° C. and stirred for 2 days. To the reaction mixture was added water (230 mL) over ten minutes. The layers were separated and the aqueous was extracted with toluene (2×200 mL). The combined organics were washed with brine (1×200 mL), dried with magnesium sulfate, filtered, and concentrated to afford the title compound (57.8 g, 98%). $^1$H-NMR (CDCl$_3$, 500 MHz): 7.31 (m, 5H), 5.76 (m, 1H), 5.15 (m, 4H), 4.51 (m, 1H), 3.98 (d, J=9.48, 2H), 3.36 (m, 8H).

Step C. Allyl-(2-oxo-ethyl)-carbamic acid benzyl ester. To a 250 mL round-bottomed flask equipped with nitrogen inlet and magnetic stirring, were added allyl-(2,2-dimethoxy-ethyl)-carbamic acid benzyl ester (57.2 g, 205 mmol) and formic acid (88%, 67 mL). The reaction mixture was stirred at room temperature overnight. After concentration under reduced pressure, the resulting residue was taken up in 100 mL EA, 50 mL hexane, and 90 mL water. After separation of the layers, the aqueous layer was additionally extracted three times with hexanes (50 mL)/ethyl acetate (100 mL). The combined organics were washed with brine until the wash had a pH=6. The organics were dried with magnesium sulfate, filtered, and concentrated under reduced pressure to an oil (45.2 g, 95% yield). $^1$H-NMR (CDCl$_3$, 400 MHz): 9.57 (d, 1H), 7.31 (m, 5H), 5.77 (m, 1H). 5.15 (m, 4H), 4.05 (m, 4H).

Step D. Allyl-(2-hydroxyimino-ethyl)-carbamic acid benzyl ester. To a 1 L round-bottomed flask, were added allyl-(2-oxo-ethyl)-carbamic acid benzyl ester (45.2 g, 193.8 mmol) and hydroxylamine hydrochloride (17.5 g, 251.9 mmol) in acetonitrile (260 mL). To the resulting mixture was added a solution of sodium acetate trihydrate (29.5 g, 217 mmol) in H$_2$O (130 mL). The reaction mixture was stirred at room temperature under nitrogen$_{(g)}$ overnight. The mixture was concentrated under reduced pressure and the resulting residue was extracted with ethyl acetate (2×130 mL). The combined organics were washed with brine, dried with magnesium sulfate, filtered, and concentrated under reduced pressure to afford the title compound (46.5 g, 97%). $^1$H-NMR (CDCl$_3$, 400 MHz): 7.32 (m, 5H), 6.72 (m, 1H), 5.77 (bs, 1H), 5.16 (m, 4H), 4.19 (m, 1H), 3.95 (m, 3H). MS (electrospray): exact mass calculated for C$_{13}$H$_{16}$N$_2$O$_3$, 248.12; m/z found, 249.1 [M+H]$^+$.

Step E. 3-Amino-4-hydroxymethyl-pyrrolidine-1-carboxylic acid benzyl ester. To a 1 L round-bottomed flask equipped with reflux condenser, heating mantle, nitrogen inlet, and magnetic stir bar, were added allyl-(2-hydroxyimino-ethyl)-carbamic acid benzyl ester (45.5 g, 183.3 mmol) and pentanol (560 mL). The reaction mixture was warmed to 135° C. and stirred for 20 h. The reaction mixture was transferred to a 2.25 L Parr bottle. To the mixture were added ethanol (95 mL) and Raney Ni (11.4 g). The slurry was shaken under an atmosphere of H$_{2(g)}$ (60 psi) for 4 h. The resulting reaction mixture was filtered and taken on directly to the next step.

Step F. 3-tert-Butoxycarbonylamino-4-hydroxymethyl-pyrrolidine-1-carboxylic acid benzyl ester. To a 3 L round-bottomed flask, was added the filtered reaction mixture of 3-amino-4-hydroxymethyl-pyrrolidine-1-carboxylic acid benzyl ester in pentanol/ethanol mixture. To the mixture sodium bicarbonate (30.8 g, 367 mmol), H$_2$O (655 mL), and Boc anhydride (38 g, 174.1 mmol) were added. The mixture was stirred under N$_{2(g)}$ for 15 h at room temperature. The biphasic mixture was then separated and the organics were washed with brine (655 mL). The organics were dried with magnesium sulfate, filtered, and concentrated under reduced pressure. The material was warmed to 98° C. in toluene/heptanes (280 mL each) and then filtered. The filtrate was slowly cooled to room temperature and stirred for 20 h. The resulting solids were filtered and washed with heptanes to provide the title compound (39.5 g, 64% over two steps). $^1$H-NMR (CD$_3$OD, 400 MHz): 7.31 (m, 5H), 5.11 (s, 2H), 4.20 (m, 1H), 3.50-3.70 (m, 4H), 3.34-3.42 (m, 1H), 3.18-3.29 (m, 1H), 2.49 (m, 1H), 1.44 (s, 9H).

Step G. 3-tert-Butoxycarbonylamino-4-methanesulfonyloxymethyl-pyrrolidine-1-carboxylic acid benzyl ester. To a 2 L round-bottomed flask equipped with temperature probe and nitrogen inlet, were added 3-tert-butoxycarbonylamino-4-hydroxymethyl-pyrrolidine-1-carboxylic acid benzyl ester (39.5 g, 112.7 mmol) in dichloromethane (550 mL) and triethylamine (22.8 g, 225.4 mmol). The solution was cooled to 0° C. in an ice bath. Methanesulfonyl chloride (16.8 g, 146.5 mmol) was added dropwise over 20 min. The reaction mixture was allowed to warm to room temperature over 2 h. After stirring for 20 h, the reaction mixture was quenched with H$_2$O (550 mL) and the resulting layers were separated. The aqueous was extracted with DCM and the combined organics were then washed with brine, dried over magnesium sulfate, filtered, and concentrated under reduced pressure to an oil (40.2 g, 83% yield). $^1$H-NMR (CDCl$_3$, 400 MHz): 7.32 (m, 5H), 5.13 (s, 2H), 4.69 (m, 1H), 4.38 (m, 2H), 4.19 (m, 1H), 3.67 (m, 2H), 3.24-3.46 (m, 2H), 3.00 (s, 3H), 2.73 (m, 1H), 1.49 (s, 9H).

Step H. 3-Benzyl, 6-tert-butyl-3,6-diazabicyclo[3.2.0]heptane-3,6-dicarboxylate. To a 1 L round-bottomed flask were added 3-tert-butoxycarbonylamino-4-hydroxymethyl-pyrrolidine-1-carboxylic acid benzyl ester (44 g, 104 mmol) in dichloromethane (150 mL) and trifluoroacetic acid (51 mL). The reaction mixture was stirred for 20 h. The reaction mixture was concentrated under reduced pressure. The residual material was taken up in ethanol (250 mL) and basified with 25% NaOH$_{(aq)}$ to pH ~12 (70 mL). Additional 25% NaOH$_{(aq)}$ (15 mL) was added and the resulting mixture was warmed to 60° C. for 1.5 h. After cooling to room temperature, the resulting mixture was then slowly added to di-tert-butyl dicarbonate (22.7 g, 104 mmol) in ethanol (30 mL) at room temperature over 40 minutes. The reaction mixture was concentrated under reduced pressure, and the resulting residual was partitioned between H$_2$O and ethyl acetate (250 mL each). The aqueous layer was extracted one more time with ethyl acetate and the combined organics were washed with brine, dried over magnesium sulfate, filtered, and concentrated under reduced pressure. The crude product was further purified by flash column chromatography (2×330 g silica, 15 to 45% EA/hexanes) to provide the title compound (20.9 g, 67%). $^1$H-NMR (CD$_3$OD, 400 MHz): 7.32 (m, 5H), 5.16 (s, 2H), 4.66 (m, 1H), 4.04 (m, 2H), 3.86 (d, J=12.1 Hz, 1H), 3.45 (m, 1H), 3.25 (m, 1H), 3.02-3.16 (m, 2H), 1.41 (s, 9H). MS (electrospray): exact mass calculated for C$_{18}$H$_{24}$N$_2$O$_4$, 332.17; m/z found, 233.1 [M+H]$^+$.

Step I. 3,6-Diaza-bicyclo[3.2.0]heptane-6-carboxylic acid tert-butyl ester. 3-Benzyl, 6-tert-butyl-3,6-diazabicyclo [3.2.0]heptane-3,6-dicarboxylate (2.61 mmol) in a Parr bottle was taken up in MeOH (0.1 M). Pd/C (5% wt-61.1% H2O from Johnson Mathey, 60 mg) was added. The mixture was placed on the Parr shaker and air was removed via vacuum. The system was purged a few time with nitrogen and then allowed to shake at 15 PSI for ~1.5 hr. TLC showed that all the starting material was consumed. The mixture was filtered through a pad of Celite®. The filtrate was concentrated to provide a viscous clear residue, II in 66.1%. Material was clean enough to carry forward without purification. MS (ESI) mass calcd. for $C_{10}H_{18}N_2O_2$, 198.26; m/z found, 199.2 [M+H]$^+$. $^1$H NMR (400 MHz, CDCl$_3$) 4.73-4.50 (m, 1H), 3.98 (t, J=8.3, 1H), 3.46-3.15 (m, 2H), 3.09-2.99 (m, 1H), 2.93-2.82 (m, 1H), 2.73-2.62 (m, 1H), 2.53-2.42 (m, 1H), 2.31 (s, 1H), 1.43 (s, 9H).

Intermediate 3: Biphenyl-2-yl-(3,8-diaza-bicyclo[4.2.0]oct-8-yl)-methanone

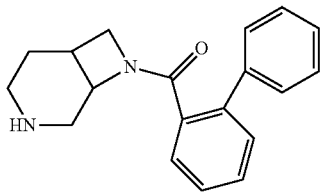 [SMILES: O=C(c1ccccc1-c1ccccc1)N1CC2CCNCC21]

Step A: 8-(Biphenyl-2-carbonyl)-3,8-diaza-bicyclo[4.2.0]octane-3-carboxylic acid tert-butyl ester. 3,8-Diaza-bicyclo[4.2.0]octane-3-carboxylic acid tert-butyl ester (Intermediate 1, 300 mg, 1.42 mmol), biphenyl-2-carbonyl chloride (429 mg, 1.98 mmol) and tri-ethyl amine (0.6 mL, 3.95 mmol) were dissolved into DCM (5 mL) and stirred at room temperature for 18 h. The reaction mixture was diluted with DCM (25 mL) and washed with 1N NaOH (10 mL) and water (2×20 mL). The organic layers were combined, dried, filtered and concentrated under reduced pressure to yield 8-(Biphenyl-2-carbonyl)-3,8-diaza-bicyclo[4.2.0]octane-3-carboxylic acid tert-butyl ester (380 mg, 68.6%). MS (ESI) mass calcd. for $C_{24}H_{28}N_2O_3$, 392.49; m/z found, 293.2 [M+H]$^+$ (mass without Boc group). $^1$H NMR (CDCl$_3$): 7.57-7.30 (m, 9H), 4.60-4.35 (m, 0.5H), 4.17-3.98 (m, 0.5H), 3.90-3.71 (m, 1H), 3.60-3.25 (m, 3H), 3.22-2.66 (m, 2H), 2.54-2.38 (m, 0.5H), 2.37-2.22 (m, 0.5H), 2.10-1.92 (m, 0.5H), 1.85-1.56 (m, 1.5H), 1.55-1.27 (m, 9H).

Step B: Biphenyl-2-yl-(3,8-diaza-bicyclo[4.2.0]oct-8-yl)-methanone. To a solution of 8-(biphenyl-2-carbonyl)-3,8-diaza-bicyclo[4.2.0]octane-3-carboxylic acid tert-butyl ester in dioxane (8.0 mL) was added trifluoro acetic acid (3 mL), the reaction mixture was stirred for 16 h at room temperature. The solvent and the excess of trifluoro acetic acid were removed under reduced pressure. The resulting trifluoro acetic acid salt of the title compound (388.0 mg was used crude without further purification. MS (ESI) mass calcd. for $C_{19}H_{20}N_2O$, 292.37; m/z found, 293.2 [M+H]$^+$.

Intermediate 4: (3,8-Diaza-bicyclo[4.2.0]oct-8-yl)-(2,6-dimethoxy-phenyl)-methanone

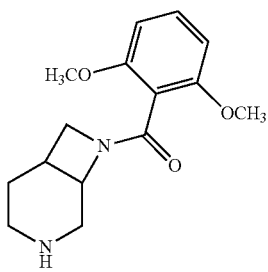 [SMILES: COc1cccc(OC)c1C(=O)N1CC2CCNCC21]

The title compound was prepared in a manner analogous to Intermediate 3, substituting 2,6-dimethoxybenzoyl chloride for biphenyl-2-carbonyl chloride in Step A. MS (ESI) mass calcd. for $C_{15}H_{20}N_2O_3$, 276.33; m/z found, 277.2 [M+H]$^+$.

Intermediate 5: 8-(2,4-Dimethyl-benzenesulfonyl)-3,8-diaza-bicyclo[4.2.0]octane

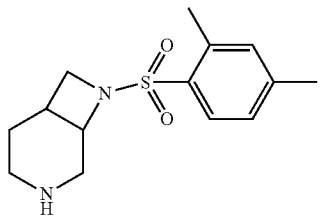 [SMILES: Cc1ccc(S(=O)(=O)N2CC3CCNCC32)c(C)c1]

Step A: 8-(2,4-dimethyl-benzenesulfonyl)-3,8-diaza-bicyclo[4.2.0]octane-3-carboxylic acid tert-butyl ester. 3,8-Diaza-bicyclo[4.2.0]octane-3-carboxylic acid tert-butyl ester (240 mg, 1.1 mmol), 2,4-dimethyl-benzenesulfonyl chloride (278 mg, 1.4 mmol) and di-isopropylethylamine (0.4 mL, 2.3 mmol) were dissolved into DCM (5.0 mL) and stirred at room temperature for 18 h. The reaction mixture was diluted with DCM (25 mL) and washed with 1N NaOH (10 mL) and water (2×20 mL). The organic layers were combined, dried, filtered and concentrated to yield the title compound (300 mg, 97%).

Step B: 8-(2,4-Dimethyl-benzenesulfonyl)-3,8-diaza-bicyclo[4.2.0]octane. To a solution of 8-(2,4-dimethyl-benzenesulfonyl)-3,8-diaza-bicyclo[4.2.0]octane-3-carboxylic acid tert-butyl ester in dioxane (8 mL) was added trifluoro acetic acid (3 mL), the reaction mixture was stirred for 16 h at room temperature. The solvent and the excess of trifluoro acetic acid were removed under reduced pressure. The resulting trifluoro acetic acid salt of the title compound was used crude without further purification (150.0 mg, 49%). MS (ESI) mass calcd. for $C_{14}H_{20}N_2O_4S$, 280.39; m/z found, 281.2 [M+H]$^+$.

Intermediate 6: (3,8-Diaza-bicyclo[4.2.0]oct-8-yl)-[4-(2-fluoro-phenyl)-2-methyl-thiazol-5-yl]-methanone

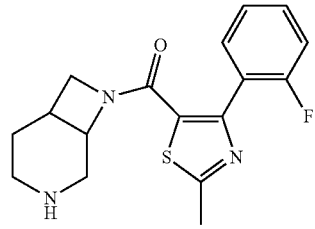 [SMILES: Cc1nc(-c2ccccc2F)c(C(=O)N2CC3CCNCC32)s1]

Step A: 8-[4-(2-fluoro-phenyl)-2-methyl-thiazole-5-carbonyl]-3,8-diaza-bicyclo[4.2.0]octane-3-carboxylic acid tert-butyl ester. 3,8-Diaza-bicyclo[4.2.0]octane-3-carboxylic acid tert-butyl ester (92 mg, 0.44 mmol), 4-(2-fluoro-phenyl)-2-methyl-thiazole-5-carboxylic acid (104 mg, 0.44 mmol), di-isopropylethylamine (0.25 mL, 1.30 mmol) and HATU (247 mg, 0.65 mmol) were dissolved into DMF (5 mL) and stirred at room temperature for 18 h. The reaction mixture was diluted with ethyl acetate (20 mL) and washed with 1N NaOH (10 mL) and water (2×100 mL). The organic layers were combined, dried, filtered and concentrated to yield the title compound (125 mg, 67%). MS (ESI) mass calcd. for $C_{12}H_{18}FN_3OS$, 431.41; m/z found, 432.3 [M+H]$^+$.

Step B: (3,8-Diaza-bicyclo[4.2.0]oct-8-yl)-[4-(2-fluoro-phenyl)-2-methyl-thiazol-5-yl]-methanone. To a solution of 8-[4-(2-fluoro-phenyl)-2-methyl-thiazole-5-carbonyl]-3,8-diaza-bicyclo[4.2.0]octane-3-carboxylic acid tert-butyl ester in dioxane (8 mL) was added trifluoro acetic acid (3 mL), the reaction mixture was stirred for 16 h at room temperature. The solvent and the excess of trifluoro acetic acid were removed under reduced pressure. The resulting trifluoro acetic acid salt of the title compound was used crude without further purification (54.0 mg, 56%). MS (ESI) mass calcd. for $C_{17}H_{18}FN_3OS$, 331.41; m/z found, 332.2 $[M+H]^+$.

Intermediate 7: (1R,6S) (3,8-Diaza-bicyclo[4.2.0]oct-8-yl)-(2-thiophen-2-yl-phenyl)-methanone

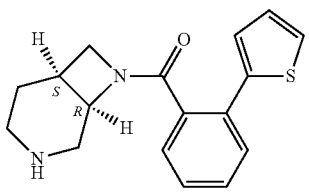

Step A: (1R,6S) 3,8-diaza-bicyclo[4.2.0]octane-3-carboxylic acid tert-butyl ester was prepared according to Frost, J. M., et. al., *J. Med. Chem.,* 2006, 49, 7843-7853).

Step B: Intermediate 7 was prepared in a manner analogous to Intermediate 3, substituting (1R,6S) 3,8-diaza-bicyclo[4.2.0]octane-3-carboxylic acid tert-butyl ester for 3,8-diaza-bicyclo[4.2.0]octane-3-carboxylic acid tert-butyl ester and 2-thiophen-2-yl-benzoyl chloride for biphenyl-2-carbonyl chloride in Step A. The final compound was concentrated and the residue was purified on HPLC to provide the title compound (150 mg, 66.7%). MS (ESI) mass calcd. for $C_{17}H_{18}N_2OS$, 298.4; m/z found, 299.2. $[M+H]^+$.

Intermediate 8:
2-(3,6-Diaza-bicyclo[3.2.0]hept-3-yl)-quinoxaline

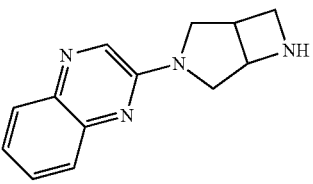 [SMILES: c1ccc2nc(N3CC4CNC4C3)cnc2c1]

Step A: Intermediate 2 (0.51 mmol), 2-chloro-quinoxaline (0.51 mmol) and $K_2CO_3$ (1.53 mmol) were taken up in DMF (0.2 M). The mixture heated to 80° C. and allowed to heat at 80° C. overnight. The mixture was cooled to room temperature, diluted with water, and extracted with diethyl ether (3×100 mL). The organics were combined, dried over $MgSO_4$, filtered, and concentrated. The resulting crude product was purified by flash column chromatography (FCC) (50-100% EtOAc/hex) to provide 3-quinoxalin-2-yl-3,6-diaza-bicyclo[3.2.0]heptane-6-carboxylic acid tert-butyl ester (84%). MS (ESI) mass calcd. for $C_{18}H_{22}N_4O_2$, 326.39; m/z found, 327.2 $[M+H]^+$. $^1$H NMR (400 MHz, $CDCl_3$): 8.48 (s, 1H), 7.93-7.87 (m, 1H), 7.76-7.69 (m, 1H), 7.62-7.55 (m, 1H), 7.45-7.36 (m, 1H), 4.90 (br s, 1H), 4.41 (br s, 1H), 4.27-4.09 (m, 2H), 3.68-3.61 (m, 1H), 3.49-3.41 (m, 1H), 3.34-3.20 (m, 2H), 1.45 (br s, 9H).

Step B: 3-Quinoxalin-2-yl-3,6-diaza-bicyclo[3.2.0]heptane-6-carboxylic acid tert-butyl ester (0.52 mmol) was treated with 4M HCl in dioxane (2 mL) in dichloromethane (2 mL) to give the title compound. MS (ESI) mass calcd. for $C_{13}H_{14}N_4$, 226.28; m/z found 227.2 $[M+H]^+$.

Intermediate 9: 3-(4,6-Dimethyl-pyrimidin-2-yl)-3,6-diaza-bicyclo[3.2.0]heptane

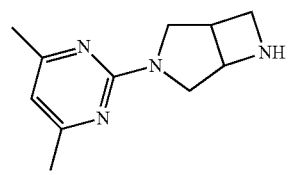

The title compound was prepared in a manner analogous to Intermediate 8, using 2-chloro-4,6-dimethylpyrimidine. MS (ESI) mass calcd. for $C_{11}H_{16}N_4$, 204.27; m/z found 205.2 $[M+H]^+$.

Intermediate 10: 3-(4-Methyl-pyrimidin-2-yl)-3,6-diaza-bicyclo[3.2.0]heptane

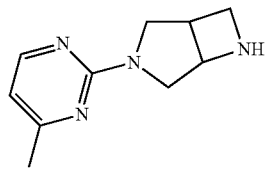

The title compound was prepared in a manner analogous to Intermediate 8, using 2-chloro-4-methyl pyrimidine. MS (ESI) mass calcd. for $C_{10}H_{14}N_4$, 190.25; m/z found 191.2 $[M+H]^+$.

Intermediate 11: 3-(4-Phenyl-pyrimidin-2-yl)-3,6-diaza-bicyclo[3.2.0]heptane

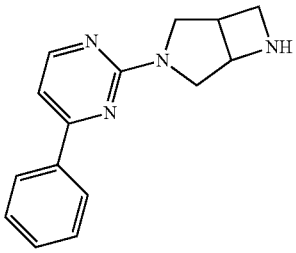 [SMILES: c1ccc(-c2ccnc(N3CC4CNC4C3)n2)cc1]

The title compound was prepared in a manner analogous to Intermediate 8, using 2-chloro-4-phenyl pyrimidine. MS (ESI) mass calcd. for $C_{15}H_{16}N_4$, 252.31; m/z found 253.2 $[M+H]^+$.

Intermediate 12: (1S,6R)-3,8-Diazabicyclo[4.2.0]octan-8-yl(2-(3-methyl-1,2,4-oxadiazol-5-yl)phenyl)methanone

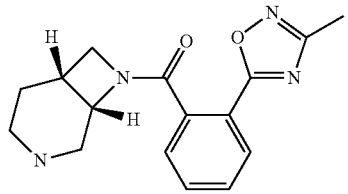 [SMILES: Cc1noc(-c2ccccc2C(=O)N2C[C@H]3CCNC[C@H]32)n1]

Step A: (1S,6R) 3,8-Diaza-bicyclo[4.2.0]octane-3-carboxylic acid tert-butyl ester was prepared according to Frost, J. M., et. al., *J. Med. Chem.*, 2006, 49, 7843-7853), Intermediate 1.

Step B: (1S,6R)-tert-Butyl 8-(2-(3-methyl-1,2,4-oxadiazol-5-yl)benzoyl)-3,8-diazabicyclo[4.2.0]octane-3-carboxylate. To a solution of 3,8-diaza-bicyclo[4.2.0]octane-3-carboxylic acid tert-butyl ester (550 mg, 2.59 mmol) in $CH_2Cl_2$ (9 mL) was added 2-(3-methyl-1,2,4-oxadiazol-5-yl)benzoic acid (545 mg, 2.59 mmol) followed by EDCl (745 mg, 3.89 mmol), HOBt (525 mg, 3.89 mmol) and TEA (0.72 mL, 5.18 mmol). The mixture was stirred for 14 h at room temperature and then washed (2×) with saturated aqueous $NH_4Cl$ solution. The organic layer was dried over $Na_2SO_4$, filtered and concentrated in vacuo. Chromatography (Hex to 100% EtOAc/Hex) afforded the desired product as a colorless foam (665 mg, 61%). MS (ESI): mass calculated for $C_{21}H_{26}N_4O_4$, 398.20, m/z found 399.0 $[M+1]^+$. $^1H$ NMR (500 MHz, $CDCl_3$): 8.14-8.05 (m, 1H), 7.67-7.52 (m, 2H), 7.45-7.36 (m, 1H), 4.39-4.21 (m, 2H), 4.04-3.96 (m, 1H), 3.90-3.83 (m, 0H), 3.77-3.43 (m, 3H), 2.96-2.76 (m, 2H), 2.47 (s, 3H), 2.03-1.72 (m, 2H), 1.54-1.36 (m, 9H).

Step C: (1S,6R)-3,8-Diazabicyclo[4.2.0]octan-8-yl(2-(3-methyl-1,2,4-oxadiazol-5-yl)phenyl)methanone. The product of Step B (645 mg, 1.63 mmol), DCM (8 mL), TFA (3 mL) were stirred at room temperature for 2 h and then concentrated in vacuo. The residue was dissolved in DCM and treated with Dowex 550A resin. After stirring for 2 h the resin was removed by filtration and the filtrate was concentrated in vacuo to a colorless oil which was taken on to the next step without further purification. MS (ESI) mass calculated for $C_{16}H_{18}N_4O_2$, 298.14; m/z found, 299.1.

Intermediate 13: 2,5-Dichloro-4-methylpyrimidine

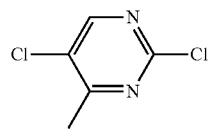

To a solution of 2,4,5-trichloropyrimidine (2.52 g, 13.74 mmol) in THF/NMP (86 mL/6 mL) was added $Fe(acac)_3$ (485 mg, 1.37) and the mixture was cooled to 0° C. 3.0 M MeMgBr in $Et_2O$ (6.87 mL, 20.61 mmol) was added dropwise. After 30 min at 0° C., the reaction was complete and quenched with saturated aqueous $NH_4Cl$ solution. $Et_2O$ was added and the layers were separated and the aqueous layer was further extracted with several portions of $Et_2O$. The combined organic extracts were dried over $Na_2SO_4$, filtered and concentrated in vacuo. Chromatography (Hex to 10% EtOAc/Hex) gave the desired product as a white solid (1.45 g, 65%). $^1H$ NMR (500 MHz, $CDCl_3$): 8.47 (s, 1H), 2.61 (s, 3H).

Intermediate 14: 2,5-Dichloro-4,6-dimethylpyrimidine

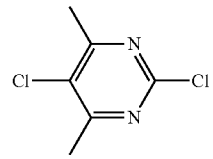

To 5-chloro-4,6-dimethylpyrimidin-2-ol (992 mg, 6.26 mmol) was added $POCl_3$ (2.22 mL, 23.77 mmol) followed by $Et_2NPh$ (0.75 mL, 4.69 mmol) dropwise. The mixture was heated at 125° C. for 2 h. At approximately 2 h the reaction became homogeneous and was checked by HPLC and it showed all starting material had been consumed. The mixture was allowed to cool to room temperature and was then added dropwise to ice. After the ice had melted there was a white solid in a pink liquid. The aqueous layer was extracted with DCM and the combined organic layers were dried over $Na_2SO_4$, filtered and concentrated in vacuo. Chromatography (Hex to 10% EtOAc/Hex) afforded the desired product as a white solid (915 mg, 83%). $^1H$ NMR (500 MHz, $CDCl_3$): 2.57 (s, 6H).

Intermediate 15: 3-Fluoro-2-(3-methyl-1,2,4-oxadiazol-5-yl)benzoic acid

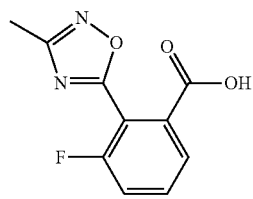 [SMILES: Cc1noc(-c2c(F)cccc2C(=O)O)n1]

Method A:

Step A: 2-Fluoro-6-(methoxycarbonyl)benzoic acid. 3-Fluorophthalic anhydride (377 mg, 2.27 mmol) was dissolved in MeOH (6 mL) and heated to reflux for 15 h. The mixture was concentrated in vacuo and the two products (400 mg, 89%), 2-fluoro-6-(methoxycarbonyl)benzoic acid and 3-fluoro-2-(methoxycarbonyl)benzoic acid, were taken on to the next step without purification.

Step B: (Z)-Methyl 2-((((1-aminoethylidene)amino)oxy)carbonyl)-3-fluorobenzoate. To a heterogeneous mixture of the two acids from step A (400 mg, 2 mmol) at 0° C. in DCM (5 mL) was added oxalyl chloride (0.244 mL, 2.32 mmol) followed by DMF (0.05 mL). Gas evolution commenced immediately and after 5 min the ice bath was removed. When gas evolution had ceased and the mixture was homogeneous an aliquot was removed and quenched with MeOH. Formation of the methyl ester was confirmed by HPLC and the mixture was concentrated in vacuo. The viscous liquid was dissolved in fresh DCM (5 mL) and treated with solid N-hydroxyacetamidine (165 mg, 2.22 mmol) in several portions followed by TEA (0.351 mL, 2.52 mmol). After stirring for 14 h at ambient temperature the mixture was concentrated in vacuo. Chromatography (Hex to 100% EtOAc/Hex) afforded two products (477 mg, 94%), (Z)-methyl 2-((((1-aminoethylidene)amino)oxy)carbonyl)-3-fluorobenzoate and (Z)-methyl 2-((((1-aminoethylidene)amino)oxy)carbonyl)-6-fluorobenzoate, which were taken on to the next step as a mixture. MS (ESI) mass calculated for $C_{11}H_{11}FN_2O_4$, 254.07; m/z found, 255.0.

Step C: 3-Fluoro-2-(3-methyl-1,2,4-oxadiazol-5-yl)benzoic acid. To the mixture of products from Step B (477 mg, 1.88 mmol) in t-BuOH (9 mL) was added NaOAc (156 mg, 1.88 mmol). The mixture was heated at 90° C. for 50 h and then concentrated in vacuo. This resulted in four products. The residue was dissolved in 1 M $K_2CO_3$ and extracted with DCM to isolate methyl 2-fluoro-6-(3-methyl-1,2,4-oxadiazol-5-yl)benzoate and methyl 3-fluoro-2-(3-methyl-1,2,4-oxadiazol-5-yl)benzoate along with unreacted (Z)-methyl 2-((((1-aminoethylidene)amino)oxy)carbonyl)-3-fluorobenzoate. The aqueous layer was then acidified with concentrate HCl and extracted with DCM. The combined organic layers from this extraction were dried over $Na_2SO_4$, filtered and concentrated in vacuo. The acid isomers were purified on a Prep Agilent system with a XBridge $O_{18}$ OBD 50×100 mm column eluting with 5 to 99% 0.05% $NH_4OH$ in $H_2O$/ACN over 17 min to afford the desired product (63 mg, 15%) as a white solid after acidification with 1 M HCl in $Et_2O$. MS (ESI) mass calculated for $C_{10}H_7FN_2O_3$, 222.04; m/z found, 223.0.

Method B:

Step A: (Z)—N'-((2-Fluoro-6-iodobenzoyl)oxy)acetimidamide. To a heterogeneous mixture of 2-fluoro-6-iodobenzoic acid (1.51 g, 5.66 mmol) at 0° C. in DCM (28 mL) was added oxalyl chloride (0.635 mL, 7.36 mmol) followed by DMF (0.15 mL). Gas evolution commenced immediately and after 5 min the ice bath was removed. When gas evolution had ceased and the mixture was homogeneous an aliquot was removed and quenched with MeOH. Formation of the methyl ester was confirmed by HPLC and the mixture was concentrated in vacuo. The viscous liquid was dissolved in fresh DCM (28 mL) and treated with solid N-hydroxyacetamidine (503 mg, 6.79 mmol) in several portions followed by TEA (1.2 mL, 8.49 mmol) at 0° C. After stirring for 14 h at ambient temperature the mixture was washed with saturated aqueous $NaHCO_3$ solution. The combined organic extracts were dried over $Na_2SO_4$, filtered and concentrated in vacuo. Chromatography (Hex to 100% EtOAc/Hex) afforded the desired product as a colorless oil (1.57 g, 86%). MS (ESI) mass calculated for $C_9H_8FIN_2O_2$, 321.96; m/z found, 323.0. $^1$H NMR (500 MHz, $CDCl_3$): 7.70-7.65 (m, 1H), 7.15-7.11 (m, 2H), 4.87 (br s, 2H), 2.06 (s, 3H).

Step B: 5-(2-Fluoro-6-iodophenyl)-3-methyl-1,2,4-oxadiazole. To a heterogeneous mixture of the product of Step A in t-BuOH (24 mL) was added NaOAc (603 mg, 7.27 mmol) in $H_2O$ (0.9 mL). The mixture was then heated to 110° C. for 12 d. The reaction was concentrated in vacuo and then dissolved in toluene. The toluene was then filtered to remove NaOAc and then concentrated in vacuo. Chromatography (Hex to 40% EtOAc/Hex) afforded the desired product as a colorless oil (1.21 g, 82%). MS (ESI) mass calculated for $C_9H_6FIN_2O$, 303.95; m/z found, 304.9. $^1$H NMR (500 MHz, $CDCl_3$): 7.82-7.77 (m, 1H), 7.29-7.20 (m, 2H), 2.55 (s, 3H).

Step C: 3-Fluoro-2-(3-methyl-1,2,4-oxadiazol-5-yl)benzoic acid. To THF (15 mL) was added 2 M i-PrMgCl in THF (2.2 mL, 4.47 mmol). This mixture was cooled to −78° C. and the product of Step B (1.09 g, 3.58 mmol) was added dropwise in THF (20 mL). The mixture was stirred for 30 min at −78° C. and then $CO_2$ from a lecture bottle was bubbled into the solution for 3 h while allowing the temperature to slowly rise. When the temperature reached −20° C. the dry ice bath was replaced with an ice bath, bubbling of $CO_2$ was ceased and the mixture was allowed to come to room temperature overnight. The mixture was quenched by the addition of $H_2O$ and a small amount of $Et_2O$. The organic layer was washed 2× with 2 N NaOH and the combined aqueous layers were then washed 3× with $Et_2O$. The aqueous layer was then acidified with concentrated HCl and extracted with DCM. The combined organic layers were dried over $Na_2SO_4$, filtered and concentrated in vacuo to afford the desired product as a white solid (661 mg, 83%). MS (ESI) mass calculated for $C_{10}H_7FN_2O_3$, 222.04; m/z found, 223.0. $^1$H NMR (500 MHz, $CDCl_3$): 7.96 (d, J=7.8, 1H), 7.72-7.64 (m, 1H), 7.50-7.44 (m, 1H), 2.56-2.48 (m, 3H).

Intermediate 16:
2-Fluoro-6-(3-methyl-1,2,4-oxadiazol-5-yl)benzoic acid

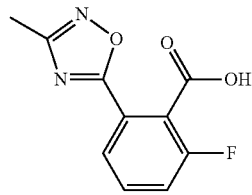 [SMILES: Cc1noc(-c2cccc(F)c2C(=O)O)n1]

Intermediate 16 was isolated from the synthesis of Intermediate 15, Method A. MS (ESI) mass calculated for $C_{10}H_7FN_2O_3$, 222.04; m/z found, 223.0.

Intermediate 17: 2-Chloro-4,5,6-trimethylpyrimidine

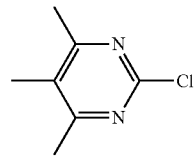

To 4,5,6-trimethylpyrimidin-2-ol (3.69 g, 26.7 mmol) was added $POCl_3$ (21.7 mL, 26.7 mmol) followed by $Et_2NPh$ (2.17 mL, 13.6 mmol) dropwise. The mixture was heated at reflux for 48 h and then added to ice dropwise. The aqueous layer was extracted with EtOAc (2×). Extraction was difficult due to a large amount of precipitate. The aqueous layer pH was adjusted to pH 4-5 with 28% $NH_4OH$ and was filtered through Celite®. The aqueous layer was then extracted with DCM and the combined organic extracts dried over $Na_2SO_4$, filtered and concentrated in vacuo to a yellow solid. Chromatography (FCC) (0 to 30% EtOAc/Hex) afforded 2-chloro-4,5,6-trimethylpyrimidine (4.26 g, 100%).

Intermediate 18:
2-Chloro-5-fluoro-4,6-dimethylpyrimidine

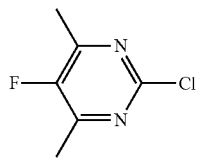

Step A: 5-Fluoropyrimidine-2,4,6-triol. To a heterogeneous mixture of urea (641 mg, 10.67 mmol) and diethylfluoromalonate (1.96 g, 10.67 mmol) in EtOH (11 mL) was added 2.68 M NaOEt in EtOH (7.96 mL, 21.34 mmol). The mixture was heated at reflux for 60 h and then allowed to cool to room temperature. The mixture was filtered and the cake was then dissolved in warm water and the resulting solution was acidified with concentrated HCl to pH 2. The mixture was allowed to cool to room temperature and then cooled in an ice bath before filtering. The cake was washed with water and dried to afford 5-fluoropyrimidine-2,4,6-triol as a slightly off white solid (1.45 g, 93%).

Step B: 2,4,6-Trichloro-5-fluoropyrimidine. To $POCl_3$ (4.49 mL, 48.15 mmol) was added 5-fluoropyrimidine-2,4,6-triol (1.41 g, 9.63 mmol) in several portions. There was a 2° C. increase in temperature. The N,N-dimethylaniline (1.23 mL, 9.73 mmol) was then added dropwise and the mixture heated at 110° C. for 24 h. The reaction mixture was allowed to cool only briefly and then was quenched by dropwise addition onto ice. When the ice was melted the aqueous layer was extracted several times with $Et_2O$. The combined organic extracts were dried over $Na_2SO_4$, filtered and concentrated in vacuo to a yellow solid after storing in the refrigerator overnight. This material was not purified further, but taken on to the next step without further purification.

Step C: 2-Chloro-5-fluoro-4,6-dimethylpyrimidine was prepared in a manner analogous to Intermediate 13, substituting 2,4,6-trichloro-5-fluoropyrimidine for 2,4,5-trichloropyrimidine. $^1$H NMR (500 MHz, $CDCl_3$): 2.50 (d, J=2.7 Hz, 6H).

Intermediate 19:
3-Fluoro-2-(1H-pyrazol-1-yl)benzoic acid

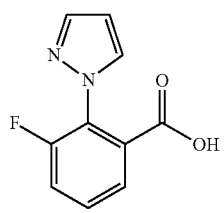

To a mixture of 3-fluoro-2-iodobenzoic acid (1.4 g, 5.26 mmol), 1H-pyrazole (0.72 g, 10.5 mmol), trans-N,N'-dimethyl-cyclohexane-1,2-diamine (0.17 mL, 1.05 mmol), CuI (50.1 mg, 0.26 mmol), dioxane (50 mL) and water (0.028 mL) was added $Cs_2CO_3$ (3.43 g, 10.5 mmol). The reaction mixture was heated to 100° C. for 1 h. The reaction mixture was cooled to ambient temperature then diluted with water. The aqueous layer was acidified to pH 2 and extracted with EtOAc (30 mL) three times. The organic layers were combined, dried over $Na_2SO_4$, filtered and concentrated. The residue was purified by FCC ($SiO_2$, gradient DCM to 10% MeOH/1% HOAC/DCM) to the yield the title compound as a colorless oil (790 mg, 72%). $^1$H NMR (400 MHz, $CDCl_3$): 7.85-7.73 (m, 1H), 7.54-7.44 (m, 1H), 7.44-7.34 (m, 1H), 6.55 (s, 1H).

Intermediate 20:
3-Methyl-2-(2H-1,2,3-triazol-2-yl)benzonitrile

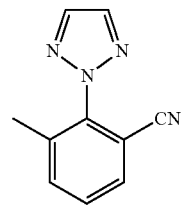

To a mixture of 2-fluoro-3-methylbenzonitrile (4.0 g, 29.6 mmol) and 2H-1,2,3-triazole (2.04 g, 29.6 mmol) in DMF (80 mL) was added potassium carbonate (8.26 g, 59.2 mmol). The resulting mixture was heated to 120° C. for 2 h. The mixture was cooled, diluted with water and extracted with EtOAc. The organic layers were combined, dried over $Na_2SO_4$, filtered and concentrated. The residue was purified by FCC ($SiO_2$, ethyl acetate/hexanes, gradient 0-50%) to yield the title compound (1.5 g, 26%). MS (ESI) mass calcd. for $C_{10}H_8N_4$, 184.2; m/z found, 185.1 [M+H]$^+$. $^1$H NMR (500 MHz, $CDCl_3$): 7.95 (s, 2H), 7.66 (d, J=7.7, 0.7 Hz, 1H), 7.59 (d, J=7.8, 0.6 Hz, 1H), 7.50 (dd, J=9.8, 5.7 Hz, 1H), 2.20 (s, 3H).

Intermediate 21:
3-Methyl-2-(1H-1,2,3-triazol-1-yl)benzonitrile

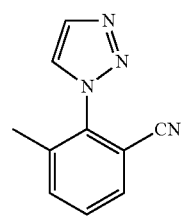

The title compound was also a product of the synthesis of Intermediate 20 (3.1 g, 56%). MS (ESI) mass calcd. for $C_{10}H_8N_4$, 184.2; m/z found, 185.1 [M+H]$^+$. $^1$H NMR (500 MHz, $CDCl_3$): 7.94 (d, J=2.1 Hz, 1H), 7.87 (d, J=1.1 Hz, 1H), 7.71-7.67 (m, 1H), 7.67-7.62 (m, 1H), 7.56 (dd, J=9.7, 5.8 Hz, 1H), 2.17 (s, 3H).

Intermediate 22:
3-Methyl-2-(2H-1,2,3-triazol-2-yl)benzoic acid

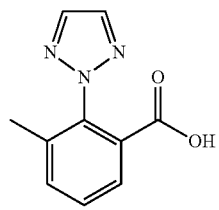

To a solution of 3-methyl-2-(2H-1,2,3-triazol-2-yl)benzonitrile (1.4 g, 7.82 mmol) in MeOH (15 mL) was added a 4 N aqueous solution of NaOH (10 mL). The resulting mixture was heated to 90° C. After 15 h the reaction mixture was cooled to ambient temperature then diluted with water (50 mL). The aqueous layer was acidified to pH 2 and extracted with EtOAc (50 mL) three times. The organic layers were combined, dried over $Na_2SO_4$, filtered and concentrated. The residue was purified by FCC ($SiO_2$, gradient DCM to 10% MeOH/1% HOAc/DCM) to yield the title compound (1.3 g, 78%). $^1$H NMR (500 MHz, $CDCl_3$): 7.90 (d, J=7.7, Hz, 1H), 7.83 (s, 2H), 7.57-7.53 (m, 1H), 7.49 (dd, J=9.7, 5.8 Hz, 1H), 2.10 (s, 3H).

Intermediate 23:
3-Methyl-2-(1H-1,2,3-triazol-1-yl)benzoic acid

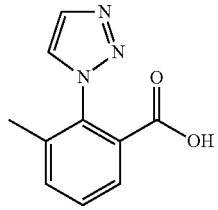

The title compound was prepared in a manner analogous to Intermediate 22, substituting 3-methyl-2-(1H-1,2,3-triazol-1-yl)benzonitrile for 3-methyl-2-(2H-1,2,3-triazol-2-yl)benzonitrile. $^1$H NMR (500 MHz, $CDCl_3$): 8.17 (s, 1H), 7.94 (s, 1H), 7.69 (d, J=6.8 Hz, 1H), 7.65 (d, J=7.7 Hz, 1H), 7.63-7.56 (m, 1H), 2.06 (s, 3H).

Intermediate 24: (1S,6R)-tert-Butyl
3,8-diazabicyclo[4.2.0]octane-3-carboxylate

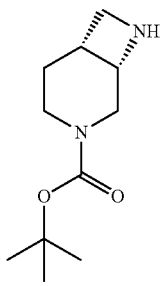

To a solution of (1R,6S)-tert-butyl 8-((S)-1-phenylethyl)-3,8-diazabicyclo[4.2.0]octane-3-carboxylate (1.5 g, 75%) in EtOH (50 mL) was added AcOH (1.5 mL). The resulting mixture was cycled through an ThalesNano H-Cube containing a 20% $Pd(OH)_2$/C catalyst cartridge at 50° C. and 100 bar of hydrogen pressure. After 16 hours the resulting mixture was removed from the ThalesNano H-Cube and poured over a saturated sodium carbonate solution (100 mL). The aqueous layer was extracted with DCM (50 mL) four times. The organic layers were combined, dried over $Na_2SO_4$, filtered and concentrated under reduced pressure to yield the title compound (755 mg, 75%) which was used in the next step without purification. MS (ESI) mass calcd. for $C_{11}H_{20}N_2O_2$, 212.2; m/z found, 213.1 [M+H]$^+$. $^1$H NMR (500 MHz, $CDCl_3$): 4.18-4.00 (m, 1H), 3.85-3.57 (m, 3H), 3.44-3.34 (m, 1H), 3.28 (dt, J=13.1, 6.5 Hz, 1H), 3.24-3.13 (m, 1H), 2.82-2.72 (m, 1H), 1.93-1.83 (m, 1H), 1.82-1.70 (m, 1H), 1.48 (s, 9H).

Intermediate 25: (1S,6R)-3,8-Diazabicyclo[4.2.0]
octan-8-yl(6-methyl-2-(1H-1,2,3-triazol-1-yl)pyridin-3-yl)methanone

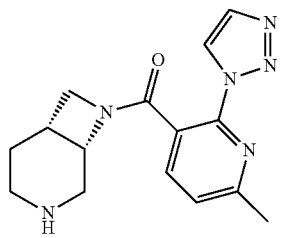 [SMILES: Cc1ccc(C(=O)N2C[C@H]3CCNC[C@H]32)c(-n2ccnn2)n1]

Step A: To a mixture of Intermediate 24 (570 mg, 2.69 mmol), 6-methyl-2-(1H-1,2,3-triazol-1-yl)nicotinic acid (603 mg, 2.95 mmol), benzotriazol-1-yloxytris(dimethylamino)phosphonium hexafluorophosphate (1200 mg, 2.69 mmol) in DCM (15 mL) was added TEA (1.1 mL, 8.06 mmol). The resulting mixture was stirred for 5 h at ambient temperature at which time water (30 mL) was added. The aqueous layer was extracted with DCM (15 mL) three times. The organic layers were combined, dried over $Na_2SO_4$, filtered and concentrated under reduced pressure. The crude residue was purified by FCC ($SiO_2$, ethyl acetate/hexanes, 0-40%) to yield (1S,6R)-tert-butyl 8-(6-methyl-2-(1H-1,2,3-triazol-1-yl)nicotinoyl)-3,8-diazabicyclo[4.2.0]octane-3-carboxylate (1.05 g, 98%). MS (ESI) mass calcd. for $C_{20}H_{26}N_6O_3$, 398.2; m/z found, 399.1 [M+H]$^+$. $^1$H NMR (500 MHz, $CDCl_3$): 8.48-8.38 (m, 1H), 7.82-7.79 (m, 1H), 7.77-7.64 (m, 1H), 7.33-7.23 (m, 1H), 4.53-4.27 (m, 2H), 4.06-3.89 (m, 1H), 3.80-3.36 (m, 4H), 3.01-2.90 (m, 1H), 2.62-2.58 (m, 3H), 2.03-1.76 (m, 2H), 1.53-1.42 (m, 9H).

Step B: To 1S,6R)-tert-butyl 8-(6-methyl-2-(1H-1,2,3-triazol-1-yl)nicotinoyl)-3,8-diazabicyclo[4.2.0]octane-3-carboxylate (1.05 g, 2.64 mmol) in DCM (15 mL) was added TFA (3 mL). The resulting mixture was allowed to stir at ambient temperature. After 16 h the mixture was concentrated under reduced pressure and the crude residue was purified by FCC ($SiO_2$, gradient DCM to 15% MeOH/10% $NH_3$/DCM) to yield the title compound (790 mg, 71%). MS (ESI) mass calcd. for $C_{15}H_{18}N_6O$, 298.2; m/z found, 299.1 [M+H]$^+$.

Intermediate 26: (1S,6R)-3,8-Diazabicyclo[4.2.0]
octan-8-yl(4-methoxy-2-(2H-1,2,3-triazol-2-yl)phenyl)methanone

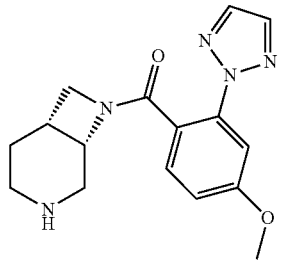 [SMILES: COc1ccc(C(=O)N2C[C@H]3CCNC[C@H]32)c(-n2nccn2)c1]

The title compound was prepared in a manner analogous to Intermediate 25, substituting 4-methoxy-2-(2H-1,2,3-triazol-2-yl)benzoic acid for 6-methyl-2-(1H-1,2,3-triazol-1-yl)nicotinic acid. MS (ESI) mass calcd. for $C_{16}H_{19}N_5O_2$, 313.2; m/z found, 314.1 [M+H]$^+$. $^1$H NMR (500 MHz, CDCl$_3$): 7.92 (s, 1H), 7.87-7.83 (m, 1H), 7.57-7.41 (m, 2H), 6.98-6.93 (m, 1H), 4.67-4.50 (m, 1H), 4.25-4.17 (m, 1H), 3.96-3.87 (m, 5H), 3.86-3.78 (m, 1H), 3.69-3.51 (m, 1H), 3.27-2.99 (m, 2H), 2.83-2.76 (m, 1H), 2.16-1.99 (m, 1H), 1.78-1.70 (m, 1H).

Intermediate 27: (1S,6R)-3,8-Diazabicyclo[4.2.0]octan-8-yl(5-methoxy-2-(2H-1,2,3-triazol-2-yl)phenyl)methanone

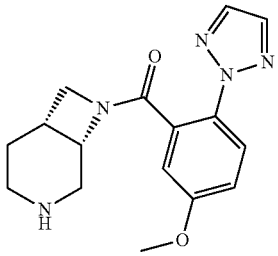 [SMILES: COc1ccc(-n2nccn2)c(C(=O)N2C[C@H]3CCNC[C@H]32)c1]

The title compound was prepared in a manner analogous to Intermediate 25, substituting 5-methoxy-2-(2H-1,2,3-triazol-2-yl)benzoic acid for 6-methyl-2-(1H-1,2,3-triazol-1-yl)nicotinic acid. MS (ESI) mass calcd. for $C_{16}H_{19}N_5O_2$, 313.2; m/z found, 314.1 [M+H]$^+$.

Intermediate 28: (1S,6R)-3,8-Diazabicyclo[4.2.0]octan-8-yl(2-fluoro-6-(2H-1,2,3-triazol-2-yl)phenyl)methanone

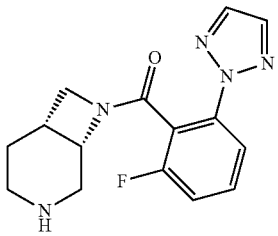 [SMILES: O=C(c1c(F)cccc1-n1nccn1)N1C[C@H]2CCNC[C@H]21]

Step A: (1S,6R)-tert-Butyl 8-(2-fluoro-6-(2H-1,2,3-triazol-2-yl)benzoyl)-3,8-diazabicyclo[4.2.0]octane-3-carboxylate. To 2-fluoro-6-(2H-1,2,3-triazol-2-yl)benzoic acid (406 mg, 1.5 mmol) in PhCH$_3$ (5 mL) was added SOCl$_2$ (117 µL, 1.6 mmol). The flask was heated with an oil bath to 50° C. for 1 h. To (1S,6R)-tert-butyl 3,8-diazabicyclo[4.2.0]octane-3-carboxylate (260 mg, 1.3 mmol) and Na$_2$CO$_3$ (519 mg, 4.9 mmol) in PhCH$_3$ (5 mL) and H$_2$O (5 mL) at 0° C. was added the above solution dropwise. The reaction was allowed to warm slowly to rt and stir for 15 h and extracted with DCM (2×). The combined organics were dried (Na$_2$SO$_4$). Purification via silica gel chromatography (1-7% 2M NH$_3$/MeOH in CH$_2$Cl$_2$) gave 335 mg (68%) of the title compound. MS (ESI) mass calcd. $C_{20}H_{24}FN_5O_3$, 401.44; m/z found 346.1 [M–C(CH$_3$)$_3$]$^+$.

Step B: (1S,6R)-3,8-Diazabicyclo[4.2.0]octan-8-yl(2-fluoro-6-(2H-1,2,3-triazol-2-yl)phenyl)methanone. To (1S,6R)-tert-butyl 8-(2-fluoro-6-(2H-1,2,3-triazol-2-yl)benzoyl)-3,8-diazabicyclo[4.2.0]octane-3-carboxylate (400 mg, 1.0 mmol) in CH$_2$Cl$_2$ (5 mL) was added TFA (5 mL). After the reaction was judged complete, the volatiles were removed under reduced pressure. The resulting residue was neutralized using 5% Na$_2$CO$_3$(aq) followed by extraction with CH$_2$Cl$_2$ (3×). The combined organics were dried (Na$_2$SO$_4$) and concentrated to give the title compound as an oil that was used without further purification.

Intermediate 29: (1R,6S)-3,8-Diazabicyclo[4.2.0]octan-8-yl(2-fluoro-6-(2H-1,2,3-triazol-2-yl)phenyl)methanone

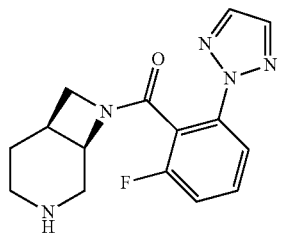 [SMILES: O=C(c1c(F)cccc1-n1nccn1)N1C[C@@H]2CCNC[C@@H]21]

The title compound was prepared in a manner analogous to Intermediate 28, substituting (1R,6S)-tert-butyl 3,8-diazabicyclo[4.2.0]octane-3-carboxylate for (1S,6R)-tert-butyl 3,8-diazabicyclo[4.2.0]octane-3-carboxylate. MS (ESI) mass calcd. $C_{15}H_{16}FN_5O$, 301.32; m/z found 302.0 [M+H]$^+$.

Intermediate 30: (1S,6R)-3,8-Diazabicyclo[4.2.0]octan-8-yl(5-fluoro-2-(2H-1,2,3-triazol-2-yl)phenyl)methanone

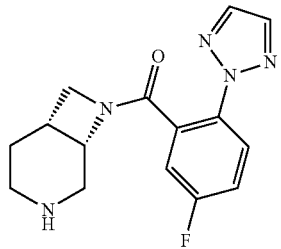 [SMILES: O=C(c1cc(F)ccc1-n1nccn1)N1C[C@H]2CCNC[C@H]21]

The title compound was prepared in a manner analogous to Intermediate 28, substituting 5-fluoro-6-(2H-1,2,3-triazol-2-yl)benzoic acid for 2-fluoro-6-(2H-1,2,3-triazol-2-yl)benzoic acid. MS (ESI) mass calcd. $C_{15}H_{16}FN_5O$, 301.32; m/z found 302.0 [M+H]$^+$.

Intermediate 31: (1S,6R)-3,8-Diazabicyclo[4.2.0]octan-8-yl(3-fluoro-2-(2H-1,2,3-triazol-2-yl)phenyl)methanone

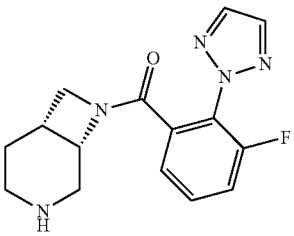 [SMILES: O=C(c1cccc(F)c1-n1nccn1)N1C[C@H]2CCNC[C@H]21]

Step A: (1S,6R)-tert-butyl 8-(3-fluoro-2-(2H-1,2,3-triazol-2-yl)benzoyl)-3,8-diazabicyclo[4.2.0]octane-3-carboxylate. To 3-fluoro-2-(2H-1,2,3-triazol-2-yl)benzoic acid (390 mg, 1.9 mmol) in $CH_2Cl_2$ (18 mL) at 0° C. was added DMF (15 μL, 0.2 mmol) and oxalyl chloride (190 μL, 2.3 mmol). After 20 min, the 0° C. ice bath was removed and the reaction allowed to warm to rt. After 30 min the mixture was concentrated, diluted with $CH_2Cl_2$ (9 mL) and added to (1S,6R)-tert-butyl 3,8-diazabicyclo[4.2.0]octane-3-carboxylate (260 mg, 1.3 mmol) in $CH_2Cl_2$ (9 mL) and TEA (390 μL, 2.9 mmol). After judged complete by TLC and LC-MS, the reaction was diluted further with $CH_2Cl_2$ and washed with 1 N $KHSO_4$. The aqueous layer was with $CH_2Cl_2$. The combined organics were dried ($Na_2SO_4$) to give a yellow foam. Purification via silica gel using 40-100% EtOAc in hexanes gave 656 mg (86%) of the title compound as a colorless oil. MS (ESI) mass calcd. $C_{20}H_{24}FN_5O_3$, 401.44; m/z found 346.0 [M–C(CH$_3$)$_3$]$^+$.

Step B: (1S,6R)-3,8-diazabicyclo[4.2.0]octan-8-yl(3-fluoro-2-(2H-1,2,3-triazol-2-yl)phenyl)methanone. To (1S,6R)-tert-butyl 8-(3-fluoro-2-(2H-1,2,3-triazol-2-yl)benzoyl)-3,8-diazabicyclo[4.2.0]octane-3-carboxylate (656 mg, 1.6 mmol) in $CH_2Cl_2$ (10 mL) was added TFA (10 mL). After 3 h, the volatiles were removed via rotovap. The resulting residue was neutralized using 5% $Na_2CO_3$ (aq) and extracted with $CH_2Cl_2$ (3×). The aqueous layer was saturated with NaCl and extracted with $CH_2Cl_2$ (3×). The combined organics were dried ($Na_2SO_4$) and concentrated to give the title compound as a yellow foam that was used without further purification. MS (ESI) mass calcd. $C_{15}H_{16}FN_5O$, 301.32; m/z found 302.0 [M+H]$^+$.

Intermediate 32:
2-Chloro-5-fluoro-4-methylpyrimidine

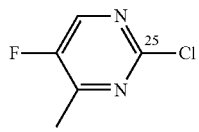

To a solution of 2,4-dichloro-5-fluoropyrimidine (1.02 g, 6.08 mmol) in THF/NMP (38 mL/3 mL) was added Fe(acac)$_3$ (215 mg, 0.61 mmol) and the mixture was cooled to 0° C. 3.0 M methylmagnesium bromide in $Et_2O$ (3.04 mL, 9.12 mmol) was added dropwise. After 30 min at 0° C., the reaction was complete and quenched with saturated aqueous $NH_4Cl$ solution. $Et_2O$ was added and the layers were separated and the aqueous layer was further extracted with several portions of $Et_2O$. The combined organic extracts were dried over $Na_2SO_4$, filtered and concentrated in vacuo. Chromatography (Hexanes to 10% EtOAc/Hexanes) gave the desired product as a waxy white solid (430 mg, 48%). $^1$H NMR (400 MHz, CDCl$_3$): 8.35 (s, 1H), 2.55 (d, J=2.5 Hz, 3H).

Intermediate 33: 2-Chloro-4,5-dimethylpyrimidine

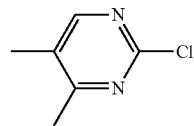

The title compound was prepared in a manner analogous to Intermediate 32, substituting 2,4-dichloro-5-methylpyrimidine for 2,4-dichloro-5-fluoropyrimidine. MS (ESI): mass calculated for $C_6H_7ClN_2$, 142.03, m/z found 143.1 [M+1]$^+$. $^1$H NMR (500 MHz, CDCl$_3$): 8.32-8.25 (m, 1H), 2.52-2.46 (m, 3H), 2.28-2.22 (m, 3H).

Intermediate 34: (1S,6R)-tert-Butyl 3,8-diazabicyclo[4.2.0]octane-3-carboxylate

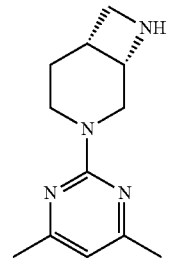

Step A: (1S,6R)-8-Benzyl 3-tert-butyl 3,8-diazabicyclo[4.2.0]octane-3,8-dicarboxylate. To (1S,6R)-tert-butyl 3,8-diazabicyclo[4.2.0]octane-3-carboxylate (1.4 g, 6.8 mmol) in THF (35 mL) and $H_2O$ (35 mL) was added $Na_2CO_3$ (1.4 g. 13.6 mmol) and CbzCl (1.1 mL, 7.5 mmol). After 18 h, the reaction mix was diluted with $H_2O$ and extracted with $CH_2Cl_2$ (2×). The combined organics were dried ($Na_2SO_4$) to give 2.4 g of the title compound as a clear oil that was used without further purification.

Step B: (1S,6R)-Benzyl 3,8-diazabicyclo[4.2.0]octane-8-carboxylate. To (1S,6R)-8-benzyl 3-tert-butyl 3,8-diazabicyclo[4.2.0]octane-3,8-dicarboxylate (300 mg, 0.9 mmol) in $CH_2Cl_2$ was added TFA (1:1). After 2 h, the reaction was concentrated and used without further purification.

Step C: (1S,6R)-Benzyl 3-(4,6-dimethylpyrimidin-2-yl)-3,8-diazabicyclo[4.2.0]octane-8-carboxylate. To (1S,6R)-benzyl 3,8-diazabicyclo[4.2.0]octane-8-carboxylate (2.5 g, 6.9 mmol) and 2-chloro-4,6-dimethylpyrimidine (980 mg, 6.9 mmol) in DMF (35 mL) was added $Cs_2CO_3$ (9.0 g, 27.6 mmol). The reaction flask was heated to 100° C. until starting materials were consumed, cooled to rt, diluted with EtOAc and washed with $H_2O$. The aqueous layer was back-extracted with EtOAc (1×). The combined organics were washed with brine and dried ($Na_2SO_4$) to give an oil. Purification via silica gel (15-75% EtOAc in hexanes) gave 1.6 g (63%) of the title compound as a clear oil. MS (ESI) mass calcd. $C_{20}H_{24}N_4O_2$, 352.44; m/z found 353.2 [M+H]$^+$.

Step D: (1S,6R)-tert-butyl 3,8-diazabicyclo[4.2.0]octane-3-carboxylate. To (1S,6R)-benzyl 3-(4,6-dimethylpyrimidin-2-yl)-3,8-diazabicyclo[4.2.0]octane-8-carboxylate (1.5 g, 4.3 mmol) in MeOH (35 mL) and AcOH (5 mL) was added 10 wt % Pd/C (450 mg) and a $H_2$ balloon. After 2 h the catalyst was filtered away and the filtrate concentrated. The resulting residue was neturalized with 5% $Na_2CO_3$ and extracted with $CH_2Cl_2$ (5×). The combined organics were dried ($Na_2SO_4$) and concentrated to give the title compound as a clear oil that was used without further purification. MS (ESI) mass calcd. $C_{12}H_{18}N_4$, 218.30; m/z found 219.1 [M+H]$^+$. $^1$H NMR (CDCl$_3$): 6.29-6.20 (m, 1H), 4.39 (dd, J=14.4, 2.9 Hz, 1H), 4.32-4.05 (m, 2H), 3.90-3.60 (m, 2H), 3.48-3.26 (m, 2H), 2.96-2.76 (m, 1H), 2.33-2.10 (m, 7H), 2.06-1.93 (m, 1H), 1.92-1.78 (m, 1H).

Intermediate 35: 3-Fluoro-2-(pyrimidin-2-yl)benzoic acid

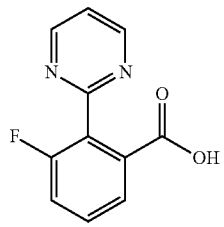 [SMILES: O=C(O)c1cccc(F)c1-c1ncccn1]

Step A: 3-Fluoro-2-(pyrimidin-2-yl)benzonitrile. 2-Iodo-4-fluorobenzonitrile (2.5 g, 10.3 mmol) and 2-tributylstannane pyrimidine (3.7 g, 10.0 mmol) were combined and dissolved in degassed DME (18 ml) then purged with bubbling $N_2$ for 5 minutes. The reaction was treated with $Pd(PPh_3)_4$ (577 mg, 0.5 mmol) and then purged with bubbling for 5 minutes in a sealed vessel and then heated in microwave at 160° C. for 90 min. The reaction was cooled and filtered through celite and concentrated to minimum volume and the ppt the formed was diluted with hexanes (40 ml) and cooled to 0° C. then filtered. The solid purified (FCC) (20-100% EA/hex) to give 3-fluoro-2-(pyrimidin-2-yl)benzonitrile. $^1$H NMR (400 MHz, $CDCl_3$): 8.93 (d, J=4.9 Hz, 2H), 8.14 (dd, J=9.6, 2.7 Hz, 1H), 7.86 (dd, J=8.6, 5.3 Hz, 1H), 7.36 (t, J=4.9 Hz, 1H), 7.32-7.24 (m, 1H).

Step B: 3-Fluoro-2-(pyrimidin-2-yl)benzoic acid. 3-Fluoro-2-(pyrimidin-2-yl)benzonitrile (98 mg, 0.5 mmol) was dissolved in MeOH (3 mL) and 2 M NaOH (aq, 1 mL). The reaction was heated at reflux for 15 h, then cooled to 23° C., acidified with 1 N aq. HCl to pH=1 and extracted with EtOAc (2×). The combined organics were washed with brine and dried over sodium sulfate to give the title compound. $^1$H NMR (400 MHz, DMSO-$d_6$): 8.89 (d, J=4.9 Hz, 1H), 7.74 (dd, J=7.6, 1.2 Hz, 1H), 7.63 (td, J=8.0, 5.5 Hz, 1H), 7.60-7.53 (m, 1H), 7.52 (t, J=4.9 Hz, 1H).

Intermediate 36: 2-Chloro-5-ethyl-4,6-dimethylpyrimidine

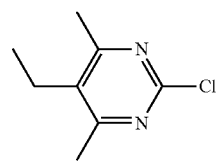

The title compound was prepared in a manner analogous to Intermediate 17, substituting 5-ethyl-4,6-dimethylpyrimidin-2-ol for 4,5,6-trimethylpyrimidin-2-ol. MS (ESI): mass calculated for $C_8H_{11}ClN_2$, 170.06, m/z found 171.1 [M+1]$^+$. $^1$H NMR (500 MHz, $CDCl_3$): 2.65 (q, J=7.6 Hz, 2H), 2.50 (s, 6H), 1.15 (t, J=7.6 Hz, 3H).

Intermediate 37: 3-Methyl-2-(1H-pyrazol-1-yl)benzoic acid

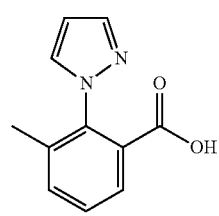

The title compound was prepared in a manner analogous to Intermediate 36 substituting 3-methyl-2-iodobenzoic acid for 3-fluoro-2-iodobenzoic acid. $^1$H NMR (500 MHz, $CDCl_3$): 7.79 (d, J=7.4 Hz, 2H), 7.48 (d, J=7.5 Hz, 1H), 7.42 (t, J=7.6 Hz, 1H), 6.53 (s, 1H), 2.07 (s, 3H).

Intermediate 38: 3-Fluoro-2-(2H-1,2,3-triazol-2-yl)benzoic acid

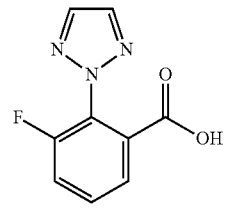

Step A: 3-Fluoro-2-(2H-1,2,3-triazol-2-yl)benzonitrile and 3-fluoro-2-(1H-1,2,3-triazol-1-yl)benzonitrile. A mixture of 2,3-difluorobenzonitrile (4.0 g, 28.8 mmol), 2H-1,2,3-triazole (1.9 g, 28.8 mmol) in DMF (85.0 mL) and $K_2CO_3$ (7.9 g, 57.5 mmol) were heated to 125° C. for 1.5 h. After cooling to rt, water was added and the mixture extracted with EtOAc (2×). The combined organics were washed with brine and dried ($Na_2SO_4$). Purification via FCC (10-100% EtOAc in hexanes) gave two products. 3-Fluoro-2-(2H-1,2,3-triazol-2-yl)benzonitrile (1.6 g, 29%), $^1$H NMR ($CDCl_3$): 7.99 (s, J=6.6 Hz, 2H), 7.67-7.63 (m, 1H), 7.61-7.53 (m, 2H), 7.26 (s, 6H) and 3-fluoro-2-(1H-1,2,3-triazol-1-yl)benzonitrile (2.0 g, 38%) $^1$H NMR ($CDCl_3$): 7.97 (dd, J=4.4, 2.8 Hz, 1H), 7.95 (d, J=1.2 Hz, 1H), 7.70 (tt, J=5.7, 2.8 Hz, 1H), 7.65 (td, J=8.1, 4.9 Hz, 1H), 7.62-7.57 (m, 1H).

Step B: 3-Fluoro-2-(2H-1,2,3-triazol-2-yl)benzoic acid. To 3-fluoro-2-(2H-1,2,3-triazol-2-yl)benzonitrile (1.5 g, 8.0 mmol) in MeOH (30 mL) was added 2M aq. NaOH (10 mL). The reaction was heated at reflux for 15 h, then cooled to rt, acidified with 1 N aq. HCl to pH 1 and extracted with $CH_2Cl_2$ (2×). The combined organics were washed with brine and dried ($Na_2SO_4$). Purification via Agilent (Reverse-Phase HPLC, basic conditions) gave the title compound (290 mg, 18%). $^1$H NMR ($CDCl_3$): 7.90 (s, 2H), 7.89-7.85 (m, 1H),

Intermediate 39: 3-Methoxy-2-(2H-1,2,3-triazol-2-yl)benzoic acid

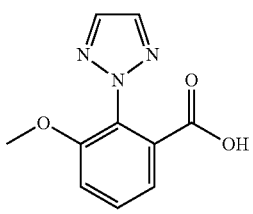 [SMILES: COc1cccc(C(=O)O)c1-n1nccn1]

The title compound was obtained during the synthesis of Intermediate 38, Step B. $^1$H NMR ($CDCl_3$): 7.92-7.83 (m, 2H), 7.66 (dd, J=7.9, 1.3 Hz, 1H), 7.61-7.54 (m, 1H), 7.27 (dd, J=8.4, 1.2 Hz, 1H), 3.82 (s, 3H).

Intermediate 40:
2-Chloro-4,4,4,5,6,6,6-septadeuteriopyrimidine

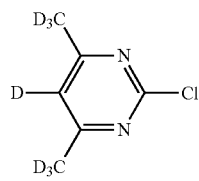

Step A: 1,1,1,3,3,3,5,5-Octadeuteriopentane-2,4-dione. To a solution of acetylacetone (10 mL, 95.1 mmol) in $D_2O$ (90 mL) was added $K_2CO_3$ (1.0 g, 7.29 mmol). The mixture was heated at 120° C. overnight. The aqueous layer was extracted with DCM and the combined organic layers were dried over $Na_2SO_4$, filtered and concentrated in vacuo to an orange liquid (Frediani et. al., *Catalysis Comm.* 2, 2001, 125).

Step B: 2-Deuteriohydroxy-4,4,4,5,6,6,6-septadeuteriopyrimidine. To a solution of 1,1,1,3,3,3,5,5-Octadeuteriopentane-2,4-dione (product of Step A) (1.60 g, 14.82 mmol) in EtOD (7 mL) was added urea-$d_4$ (0.95 g, 14.82 mmol) followed by 35% wt. DCl in $D_2O$ (2 mL, 23.71 mmol). The mixture was heated at 90° C. for 36 h, cooled to room temperature and then chilled in an ice bath before filtration and washing of the white solid with cold EtOD to afford the desired product as the HCl salt (1.53 g, 61%).

Step C: 2-Chloro-4,4,4,5,6,6,6-septadeuteriopyrimidine. To 2-deuteriohydroxy-4,4,4,5,6,6,6-septadeuteriopyrimidine (product of Step B) (1.53 g, 9.04 mmol) was added $POCl_3$ (7.9 mL, 9.04 mmol) and the mixture was heated at reflux for 16 h. The mixture was allowed to cool to room temperature and then added to ice drop wise. The aqueous mixture was neutralized to pH 6 in an ice bath with 5 N NaOH. The aqueous layer was extracted with DCM and the combined organic layers were dried over $Na_2SO_4$, filtered and concentrated in vacuo to afford the desired product as a yellow solid (1.3 g, 96%). (ESI): mass calculated for $C_6D_7ClN_2$, 149.07; m/z found, 150.1.

Intermediate 41:
5-Fluoro-2-[1,2,3]triazol-2-yl-benzoic acid

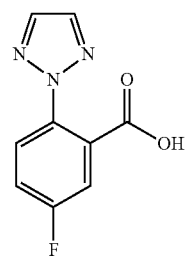

5-Fluoro-2-[1,2,3]triazol-2-yl-benzoic acid. To a solution of 5-fluoro-2-iodo-benzoic acid (3.86 g, 14.65 mmol), 2H-[1,2,3]triazole (2.5 g, 36.2 mmol), $Cs_2CO_3$ (8.62 g, 24.5 mmol), trans-N,N'-dimethyl-cyclohexane-1,2-diamine (0.4 mL), CuI (244 mg) and DMF (13 mL) were added to a microwave ready vessel and heated to 100° C. for 10 min. The mixture was cooled, diluted with water, and extracted with EtOAc. The aqueous layer was acidified and extracted with EtOAc. The organic layer was dried over $Na_2SO_4$ and concentrated. The residue was purified by FCC ($SiO_2$, gradient DCM to 10% MeOH/1% HOAc/DCM) gave the product as a white powder, (2.14 g, 71%). $^1$H NMR (400 MHz, $CD_3OD$): 7.91 (s, 2H), 7.76 (dd, J=8.9, 4.8 Hz, 1H), 7.59 (dd, J=8.5, 2.9 Hz, 1H), 7.49-7.42 (m, 1H).

Intermediate 42: 2-[1,2,3]-Triazol-2-yl-benzoic acid

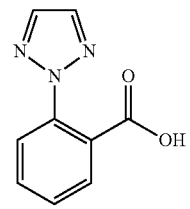 [SMILES: O=C(O)c1ccccc1-n1nccn1]

The title compound was prepared in a manner analogous to Intermediate 41, substituting 2-iodo-benzoic acid for 5-fluoro-2-iodo-benzoic acid. $^1$H NMR (400 MHz, $CD_3OD$): 7.91 (s, 2H), 7.85-7.82 (m, 1H), 7.75 (dd, J=8.1, 1.0 Hz, 1H), 7.69 (td, J=7.7, 1.5 Hz, 1H), 7.60-7.55 (m, 1H).

Intermediate 43:
2-Fluoro-6-[1,2,3]triazol-2-yl-benzoic acid

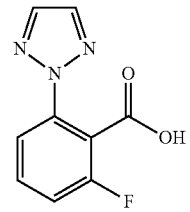

The title compound was prepared in a manner analogous to Intermediate 41, substituting 6-fluoro-2-iodo-benzoic acid for 5-fluoro-2-iodo-benzoic acid. $^1$H NMR (400 MHz, $CD_3OD$): 7.96 (s, 2H), 7.87-7.82 (m, 1H), 7.70 (td, J=8.1, 5.1 Hz, 1H), 7.59 (ddd, J=9.7, 8.4, 1.4 Hz, 1H).

Intermediate 44:
4-Fluoro-2-[1,2,3]triazol-2-yl-benzoic acid

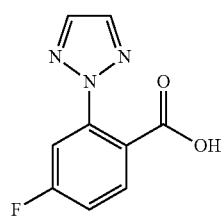

The title compound was prepared in a manner analogous to Intermediate 41, substituting 4-fluoro-2-iodo-benzoic acid for 5-fluoro-2-iodo-benzoic acid. $^1$H NMR (400 MHz, CD$_3$OD): 7.93 (s, 2H), 7.88 (dd, J=8.7, 5.9 Hz, 1H), 7.56 (dd, J=9.2, 2.5 Hz, 1H), 7.38-7.30 (m, 1H).

Intermediate 45: 5-Fluoro-2-pyrimidin-2-yl-benzoic acid

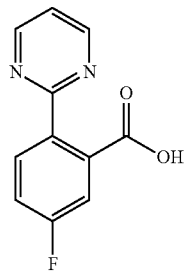 [SMILES: O=C(O)c1cc(F)ccc1-c1ncccn1]

Step A. 5-Fluoro-2-iodo-benzoic acid methyl ester. To a 500 mL round-bottomed flask was added 5-fluoro-2-iodo-benzoic acid (23 g, 86.5 mmol) in methanol (230 mL). To the resulting solution was added conc. sulfuric acid (2.3 mL, 43.2 mmol). The reaction mixture was warmed to 65° C. and stirred for 15 h. The resulting mixture was concentrated under reduced pressure to a crude which was then was partitioned between ethyl acetate (250 mL) and a half sat. Na$_2$CO$_{3(aq)}$ solution (250 mL). The layers were thoroughly mixed and then separated. The organic layer was dried over magnesium sulfate, filtered, and concentrated under reduced pressure to provide a yellow oil (23 g, 95% yield). $^1$H NMR (400 MHz, CDCl$_3$): 7.94 (dd, J=8.7, 5.4 Hz, 1H), 7.54 (dd, J=9.0, 3.1 Hz, 1H), 6.93 (m, 1H), 3.94 (s, 3H).

Step B: 5-Fluoro-2-(4,4,5,5-tetramethyl-[1,3,2]diox-aborolan-2-yl)-benzoic acid methyl ester. To a 1 L round-bottomed flask equipped with a reflux condenser, temperature probe, and nitrogen line, was added 5-fluoro-2-iodo-benzoic acid methyl ester (23 g, 82 mmol) in anhydrous THF (250 mL). Anhydrous triethylamine (34 mL, 246.4 mmol) was added and the resulting mixture was degassed with a nitrogen sparge for 5 minutes. Pinacol borane (17.9 mL, 123.2 mmol) was added and the reaction mixture was degassed once more for 5 minutes. Lastly, tri(o-tolyl)phosphine (1.25 g, 4.1 mmol) and palladium acetate (461 mg, 2.053 mmol) were added. Again, the reaction mixture was degassed with a nitrogen sparge. The mixture was heated to 65° C. and stirred for 1 h. After cooling to room temperature, the reaction mixture was quenched with half sat. ammonium chloride solution (250 mL), and the resulting layers were separated. The aqueous layer was extracted with additional ethyl acetate (250 mL) and the combined organics were dried over magnesium sulfate. After filtration and concentration, the crude product was obtained as a yellow oil (23 g). The crude product was then slurried in 25% EA/hexanes (250 mL). The resulting solids were not desired product and were removed by filtration. The resulting solution was then concentrated to a yellow oil (21 g, 75 wt % desired, 16.1 g actual product, 70% yield), which was used directly in the next step. By $^1$H-NMR, the crude product was also found to contain 14 wt % pinacol, 6.5 wt % ligand, and 4 wt % des-iodo starting material. $^1$H NMR (400 MHz, CDCl$_3$): 7.61 (dd, J=9.5, 2.5 Hz, 1H), 7.52-7.45 (m, 1H), 7.21 (td, J=8.3, 2.5 Hz, 1H), 3.91 (s, 3H), 1.41 (s, 12H).

Step C: 5-Fluoro-2-pyrimidin-2-yl-benzoic acid methyl ester. To a 250 mL round-bottomed flask, was added 5-fluoro-2-(4,4,5,5-tetramethyl-[1,3,2]dioxaborolan-2-yl)-benzoic acid methyl ester (5.9 g, 21.06 mmol) in 2-methyl-THF (50 mL). To the resulting solution was added 2-chloropyrimidine (2.9 g, 25.28 mmol), sodium carbonate (6.7 g, 63.19 mmol), and water (17 mL). The mixture was degassed for 30 minutes. PdCl$_2$(dppf)-dcm adduct (0.688 g, 0.843 mmol) was added and the reaction mixture was degassed once more for 30 minutes. The reaction mixture was warmed to 74° C. and stirred overnight. To the resulting solution was added diethyl ether (100 mL) and water (100 mL). The layers were thoroughly mixed separated. The aqueous layer was extracted with additional diethyl ether (100 mL). The combined organics were dried over magnesium sulfate, filtered, and concentrated under reduced pressure to a brown crude material (5.85 g, 49% desired, 2.87 actual product). The crude product was further purified through recrystallization in 10% EA/hexanes. The mixture was warmed to 70° C. and cooled slowly to room temperature. After filtration, the desired product was obtained as a brown solid (1.72 g actual product, 35% yield overall after recrystallization). $^1$H NMR (400 MHz, CDCl$_3$): 8.78 (d, J=4.9 Hz, 2H), 8.09 (dd, J=8.7, 5.5 Hz, 1H), 7.39 (dd, J=8.6, 2.7 Hz, 1H), 7.30-7.20 (m, 2H), 3.77 (s, 3H).

Step D: 5-Fluoro-2-pyrimidin-2-yl-benzoic acid. To a solution of 5-fluoro-2-pyrimidin-2-yl-benzoic acid methyl ester (1.72 g, 7.407 mmol) in 2-methyl-THF (20 mL) was added sodium hydroxide (0.74 g, 18.517 mmol) and water (20 mL). The mixture was heated to 72° C. and stirred for 2 h. The layers were separated and the aqueous layer was extracted with additional MTBE. A 50% HCl$_{(aq)}$ solution was then dripped into the aqueous layer until a pH of 1 was reached. The resulting solids were filtered to provide the desired product as an off-white solid (1.34 g, 83% yield). $^1$H NMR (400 MHz, CD$_3$OD): 8.82 (d, J=5.0 Hz, 2H), 7.89 (dd, J=8.6, 5.4 Hz, 1H), 7.53 (dd, J=9.0, 2.7 Hz, 1H), 7.39 (m, 2H).

Intermediate 46: 6-Methyl-2-[1,2,3]triazol-2-yl-nicotinic acid

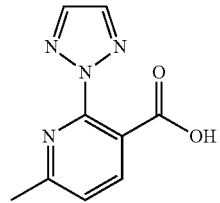

To a 100 ml round bottom flask containing 2-chloro-6-methylnicotinic acid (3 g, 17.4 mmol), copper iodide (0.16 g, 0.5 mol %), and cesium carbonate (11.4 g, 35 mmol) was added a mixture of dioxane (20 mL) and H$_2$O (0.1 ml, 5.25 mmol). Next triazole (2.03 mL, 35 mmol) and finally (R,R)-(−)-N,N'-dimethyl-1,2-cyclohexanediamine ligand (0.56 mL, 3.5 mmol) were added. The resulting clumpy yellow slurry was stirred until evenly dispersed. Upon heating to 100° C. the reaction mixture changed from a yellow slurry to pale green. As heating progressed the slurry became less thick and was stirred more easily. The light green slurry was stirred for 4 hr at 100° C. and left to stir at room temp overnight. At this point the reaction mixture appeared as a cobalt blue slurry which was then diluted with 20 mL ether and 20 mL H$_2$O. The resulting solution was thoroughly stirred and transferred to a seperatory funnel then the RBF was subsequently rinsed with 20 mL ether and H$_2$O each. The aqueous layer was separated from the organic layer and acidified to pH 1 with 6 mL conc. HCl. The now brown/lime green aqueous layer was extracted twice with EtOAc. The bright yellow organic layers were combined and dried with Na$_2$SO$_4$ and then conc. into a yellow powder under reduced pressure. To the yellow powder was added EtOAc to form a yellow slurry. The solids were filtered off and washed with EtOAc to give a very pale yellow powder, which was found by $^1$H NMR to be Intermediate 53 (25% yield). The filtrate was conc. into a yellow solid and purified by FCC using 0-5% MeOH in DCM w/0.5% AcOH to give the title compound in a 20% yield. MS (ESI): mass calculated for C$_9$H$_8$N$_4$O$_2$, 204.18; m/z found 205.3 [M+H]$^+$. $^1$H NMR (400 MHz, CD$_3$OD): 8.21-8.18 (m, 1H), 7.98 (s, 2H), 7.51 (d, J=7.9 Hz, 1H), 2.64 (s, 3H).

Intermediate 47: 2-Fluoro-6-(pyrimidin-2-yl)benzoic acid

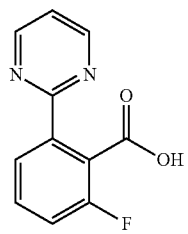 [SMILES: O=C(O)c1c(F)cccc1-c1ncccn1]

Step A: 2-Fluoro-6-iodo-benzoic acid methyl ester. To a 200 mL round-bottomed flask were added 2-fluoro-6-iodo-benzoic acid (7.5 g, 28.2 mmol), LiOH.H$_2$O (1.42 g, 33.8 mmol), and THF (100 mL). The resulting mixture was warmed to 50° C. and stirred for 2 h. Dimethyl sulfate (4.03 mL, 42.3 mmol) was then added and the mixture was warmed to 65° C. After 2 h, the mixture was cooled to room temperature and NH$_4$Cl$_{(aq)}$ (50 mL, 13 wt % solution) was added. The two resulting layers were thoroughly mixed and then separated. The organic layer was dried over MgSO$_4$, filtered, and concentrated under reduced pressure to a light brown oil (7.79 g, 99% yield). $^1$H NMR (400 MHz, CDCl$_3$): 7.68-7.60 (m, 1H), 7.15-7.06 (m, 2H), 3.98 (s, 3H).

Step B: 2-Fluoro-6-(4,4,5,5-tetramethyl-[1,3,2]dioxaborolan-2-yl)-benzoic acid methyl ester. To a 500 mL round-bottomed flask were added 2-fluoro-6-iodo-benzoic acid methyl ester (7.29 g, 26.0 mmol) and anhydrous THF (150 mL). This mixture was cooled to 0° C. and i-PrMgCl (13.7 mL, 2 M in THF, 27.3 mmol) was added dropwise. After 10 min, 2-isopropoxy-4,4,5,5-tetramethyl-1,3,2-dioxaborolane (5.58 mL, 27.3 mmol) was added. The mixture was allowed to warm to room temperature, and after 30 min NH$_4$Cl$_{(aq)}$ (150 mL, 13 wt % solution) was added. The layers were mixed and then separated, and the aqueous layer was extracted with 100 mL of MTBE. The combined organic layers were dried over Na$_2$SO$_4$, filtered, and concentrated to a final mass of 6.07 g (90% wt %, 75% yield). $^1$H NMR (400 MHz, CDCl$_3$): 7.47-7.38 (m, 2H), 7.17-7.11 (m, 1H), 3.92 (s, 3H), 1.36 (s, 12H).

Step C: 2-Fluoro-6-pyrimidin-2-yl-benzoic acid methyl ester. To a 250 mL round-bottomed flask under nitrogen were added 2-fluoro-6-(4,4,5,5-tetramethyl-[1,3,2]dioxaborolan-2-yl)-benzoic acid methyl ester (5.46 g, 19.5 mmol) in 2-methyl-THF (50 mL), 2-chloropyrimidine (2.68 g, 23.4 mmol), and sodium carbonate (6.2 g, 58.5 mmol) in water (17 mL). PdCl$_2$(dppf)-dcm adduct (CAS#72287-26-4) (1.27 g, 1.56 mmol) was then added and the reaction mixture was warmed to 74° C. and stirred for 2.5 h. After cooling, the mixture was diluted with MTBE (50 mL) and water (80 mL). The layers were thoroughly mixed separated. The aqueous layer was extracted with additional MTBE (100 mL). The combined organics were dried over magnesium sulfate, filtered, concentrated and then purified by flash chromatography (0-25% EA/hexanes) to provide the title compound (1.72 g, 72 wt %, 30% yield). $^1$H NMR (400 MHz, CDCl$_3$): 8.79 (d, J=4.9 Hz, 2H), 8.15 (d, J=7.9 Hz, 1H), 7.51 (td, J=8.1, 5.6 Hz, 1H), 7.28-7.20 (m, 2H), 3.92 (s, 3H).

Step D: 2-Fluoro-6-pyrimidin-2-yl-benzoic acid. To a solution of 2-fluoro-6-pyrimidin-2-yl-benzoic acid methyl ester (1.36 g, 5.85 mmol) in 2-methyl-THF (20 mL) was added sodium hydroxide (2 M in water, 9.3 mL, 18.6 mmol). The mixture was heated to 72° C. and stirred for 9 h. The layers were separated and the aqueous layer acified to pH 2 by dropwise addition of 50% HCl$_{(aq)}$ (3.1 mL). The resulting solids were stirred for 1 h, filtered, washed with water, MTBE, and heptanes, and then dried to provide the desired product as a white solid (1.12 g, 88% yield). $^1$H NMR (400 MHz, CD$_3$OD): 8.83 (d, J=4.9 Hz, 2H), 8.03 (dd, J=7.9, 0.8 Hz, 1H), 7.59 (td, J=8.1, 5.6 Hz, 1H), 7.40 (t, J=4.9 Hz, 1H), 7.34 (ddd, J=9.4, 8.4, 1.0 Hz, 1H).

Intermediate 48: 4-Methoxy-2-(2H-1,2,3-triazol-2-yl)benzoic acid

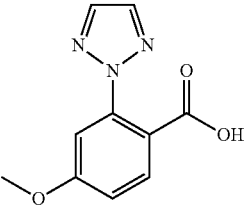 [SMILES: COc1ccc(C(=O)O)c(-n2nccn2)c1]

To 2-bromo-4-methoxybenzoic acid (4 g, 17.3 mmol), CuI (266 mg, 1.4 mmol) and Cs$_2$CO$_3$ (11.2 g, 34.6 mmol) was added dioxane (36 mL), water (94 µL, 5.1 mmol), 2H-1,2,3-triazole (2.0 mL, 34.6 mmol) and (1R,2R)—N1,N2-dimethylcyclohexane-1,2-diamine (683 µL, 4.3 mmol). The reaction mixture was heated to 100° C. for 3 hr. The reaction mixture was cooled rt, then EtOAc and water were added. The mixture was transferred to a separatory funnel and the aqueous layer separated. The aqueous layer was acidified with conc. HCl to pH~2 and extracted with EtOAc (2×). The organic layers were washed with brine and dried (Na$_2$SO$_4$) to give a yellow solid. This material was slurried with EtOAc (~20 mL) and the solids filtered (>95% 4-methoxy-2-(1H-1,2,3-triazol-1-yl)benzoic acid by HPLC). Purification (FCC) (50% DCM to 100% DCM containing 10% (5% formic acid/MeOH)) gave the title compound (2.6 g) as a yellow solid. $^1$H NMR (CDCl$_3$): 7.99-7.90 (m, 1H), 7.83 (s, 2H), 7.20 (d, J=2.5 Hz, 1H), 7.03 (dd, J=8.8, 2.6 Hz, 1H), 3.89 (s, J=17.6 Hz, 3H).

Intermediate 49: 6-Methyl-2-[1,2,3]triazol-1-yl-nicotinic acid

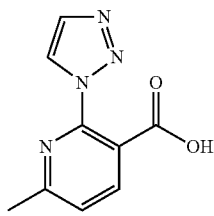

The title compound was isolated from the procedure used to prepare Intermediate 46 with a 25% yield. MS (ESI): mass calculated for C$_9$H$_8$N$_4$O$_2$, 204.18; m/z found 205.3 [M+H]$^+$. $^1$H NMR (400 MHz, CD$_3$OD): 8.48 (d, J=1.1 Hz, 1H), 8.25 (dd, J=7.9, 3.8 Hz, 1H), 7.88 (d, J=1.1 Hz, 1H), 7.54 (d, J=7.9 Hz, 1H), 2.64 (s, 3H).

Intermediate 50: 2-[1,2,3]Triazol-1-yl-benzoic acid

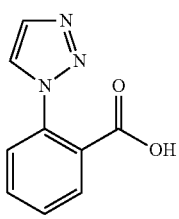 [SMILES: O=C(O)c1ccccc1-n1ccnn1]

The title compound was isolated from the synthesis of Intermediate 42. $^1$H NMR (400 MHz, CD$_3$OD): 6.70 (d, J=0.9 Hz, 1H), 6.50 (dd, J=7.7, 1.5 Hz, 1H), 6.30 (d, J=1.0 Hz, 1H), 6.24.6.18 (m, 1H), 6.17-6.11 (m, 1H), 6.01 (dd, J=7.8, 1.0 Hz, 1H).

Intermediate 51:
3-Fluoro-2-[1,2,3]triazol-2-yl-benzoic acid

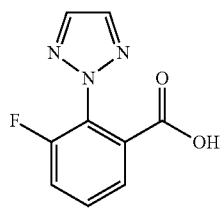 [SMILES: O=C(O)c1cccc(F)c1-n1nccn1]

The title compound was prepared in a manner analogous to Intermediate 41, substituting for 3-fluoro-2-iodo-benzoic acid for 5-fluoro-2-iodo-benzoic acid in Step A. $^1$H NMR (400 MHz, CD$_3$OD): 7.93 (s, 2H), 7.81 (d, J=8.3 Hz, 1H), 7.63-7.58 (m, 1H), 7.29 (td, J=8.9, 0.9 Hz, 1H).

Intermediate 52:
4-Chloro-2-[1,2,3]triazol-2-yl-benzoic acid

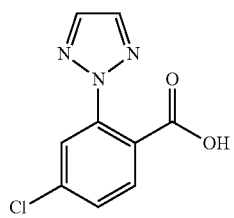 [SMILES: O=C(O)c1ccc(Cl)cc1-n1nccn1]

The title compound was prepared in a manner analogous to Intermediate 41, substituting 4-chloro-2-iodo-benzoic acid for 5-fluoro-2-iodo-benzoic acid in Step A. $^1$H NMR (400 MHz, CD$_3$OD): 7.93 (s, 2H), 7.84-7.78 (m, 2H), 7.59 (dd, J=8.3, 2.1 Hz, 1H).

Intermediate 53: 5-Iodo-2-[1,2,3]triazol-2-yl-benzoic acid

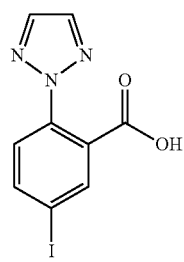

The title compound was prepared in a manner analogous to Intermediate 41, substituting 2-bromo-5-iodobenzoic acid for 5-fluoro-2-iodo-benzoic acid in Step A. $^1$H NMR (400 MHz, CD$_3$OD): 8.09 (d, J=2.0, 1H), 8.03-7.97 (m, 1H), 7.95-7.86 (m, 3H), 7.53 (d, J=8.4, 1H).

Intermediate 54:
5-Methyl-2-[1,2,3]triazol-2-yl-benzoic acid

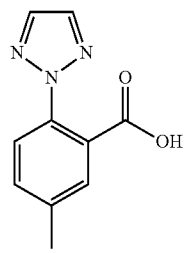

The title compound was prepared in a manner analogous to Intermediate 41, substituting for 2-iodo-5-methyl benzoic acid for 5-fluoro-2-iodo-benzoic acid in Step A. $^1$H NMR (400 MHz, CD$_3$OD): 7.87 (s 2H), 7.66 (d, J=1.3 Hz, 1H), 7.59 (d, J=8.2 Hz, 1H), 7.53-7.46 (m, 1H), 2.45 (s, 3H).

Intermediate 55:
5-Chloro-2-[1,2,3]triazol-2-yl-benzoic acid

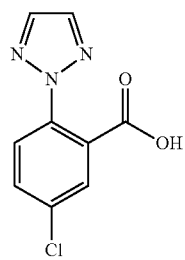 [SMILES: O=C(O)c1cc(Cl)ccc1-n1nccn1]

The title compound was prepared in a manner analogous to Intermediate 41, substituting 5-chloro-2-iodo-benzoic acid for 5-fluoro-2-iodo-benzoic acid in Step A. $^1$H NMR (400 MHz, CD$_3$OD): 7.91 (s, 2H), 7.82-7.74 (m, 2H), 7.71-7.66 (m, 1H).

Intermediate 56:
5-Methoxy-2-[1,2,3]triazol-2-yl-benzoic acid

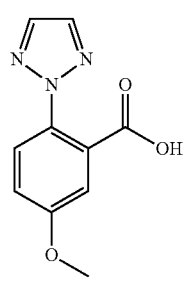 [SMILES: COc1ccc(-n2nccn2)c(C(=O)O)c1]

The title compound was prepared in a manner analogous to Intermediate 41, substituting for 2-iodo-5-methoxy benzoic acid for 5-fluoro-2-iodo-benzoic acid in Step A. $^1$H NMR (400 MHz, CD$_3$OD): 7.81 (s, J=6.4, 2H), 7.55 (d, J=8.8, 1H), 7.33 (d, J=2.9, 1H), 7.18 (dd, J=8.8, 2.9, 1H), 3.85 (s, 3H).

Intermediate 57:
5-Fluoro-2-(1H-pyrazol-5-yl)benzoic acid

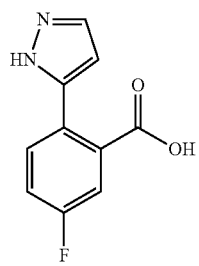 [SMILES: O=C(O)c1cc(F)ccc1-c1ccn[nH]1]

Step A: Methyl 2-bromo-5-fluorobenzoate (1.0 g, 4.2 mmol) and (1H-pyrazol-5-yl)boronic acid (485 mg, 4.6 mmol) were combined and dissolved in degassed DME (15 ml) then treated with NaHCO$_3$ (706 mg, 8.4 mmol) in water and the reaction purged with bubbling N$_2$ for 5 minutes. The reaction was treated with Pd(PPh$_3$)$_4$ (243 mg (0.2 mmol) and then purged with bubbling for 5 minutes in a sealed vessel and then heated to reflux for 2 h. The reaction mixture was cooled to 23° C., filtered, and solid rinsed with EtOAc. The organic layers were separated, dried and concentrated. Purification via FCC (ethyl acatate/hexanes, 0-30%) afforded methyl 5-fluoro-2-(1H-pyrazol-5-yl)benzoate (415 mg, 44%).

Step B: A solution of methyl 5-fluoro-2-(1H-pyrazol-5-yl) benzoate (415 mg, 1.9 mmol) in EtOH (10 ml) was treated with 4.0 eq of LiOH and stirred and monitored for two hours the reaction was complete. Reaction was made to pH=5, and then the solution concentrated under reduced pressure, during which time a ppt formed. The solution was concentrated to minimum volume and cooled in ice, filtered and washed with ice water to give 5-fluoro-2-(1H-pyrazol-5-yl)benzoic acid (172 mg, 44%). $^1$H NMR (400 MHz, DMSO-d$_6$): 13.03 (s, 1H), 7.71 (d, J=2.0 Hz, 1H), 7.67 (dd, J=8.3, 5.6 Hz, 1H), 7.37 (td, J=8.6, 2.9 Hz, 2H), 6.44 (d, J=2.2 Hz, 1H).

Intermediate 58:
2-Methyl-6-[1,2,3]triazol-2-yl-benzoic acid

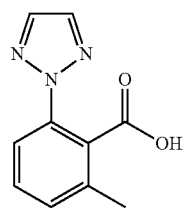

The title compound was prepared in a manner analogous to Intermediate 41, substituting for 2-iodo-6-methyl benzoic acid for 5-fluoro-2-iodo-benzoic acid in Step A. $^1$H NMR (400 MHz, CD$_3$OD): 7.89 (s, 2H), 7.72 (d, J=8.1 Hz, 1H), 7.48 (t, J=7.9 Hz, 1H), 7.36 (d, J=7.7 Hz, 1H), 2.46 (s, 3H).

Intermediate 59:
3-[1,2,3]Triazol-2-yl-pyridine-2-carboxylic acid

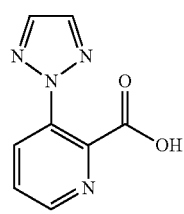

The title compound was prepared in a manner analogous to Intermediate 46 substituting 3-bromo-2-pyridinecarboxylic acid for 2-chloro-6-methylnicotinic acid. MS (ESI): mass calculated for C$_8$H$_6$N$_4$O$_2$, 190.10; m/z found 191.1 [M+H]$^+$. $^1$H NMR (400 MHz, CDCl$_3$): 8.77 (d, J=4.3 Hz, 1H), 8.26 (dt, J=6.5, 3.3 Hz, 1H), 7.88 (s, 2H), 7.65 (dd, J=8.2, 4.7 Hz, 1H).

Intermediate 60:
2,3-Dimethoxy-6-[1,2,3]triazol-2-yl-benzoic acid

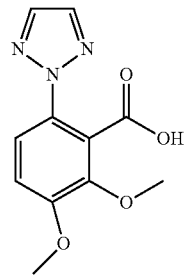 [SMILES: COc1ccc(-n2nccn2)c(C(=O)O)c1OC]

To a 20 ml microwave vial containing 2-bromo-4,5-dimethoxybenzoic acid (3 g, 11.5 mmol), copper iodide (0.04 g, 0.5 mol %), cesium carbonate (7.5 g, 23 mmol), triazole (1.33 mL, 23 mmol) and finally (R,R)-(–)-N,N'-dimethyl-1, 2-cyclohexanediamine ligand (0.36 mL, 2.3 mmol) was added DMF (12 mL). The resulting clumpy yellow slurry was stirred until evenly dispersed then heated to 120° C. for 10-20 min using a microwave. At this point the reaction mixture appeared as a blue slurry which was then diluted with 20 mL ether and 20 mL H$_2$O. The resulting solution was thoroughly stirred and transferred to a seperatory funnel then the RBF was subsequently rinsed with 20 mL ether and H$_2$O each. The aqueous layer was separated from the organic layer and acidified to pH 1 with 6 mL conc. HCl. The now brown/lime green aqueous layer was extracted twice with EtOAc. The bright yellow organic layers were combined and dried with Na$_2$SO$_4$ and then conc. into a yellow powder under reduced pressure which was purified by FCC (0-5% MeOH in DCM w/0.5% AcOH) to afford 2,3-dimethoxy-6-[1,2,3]triazol-2-yl-benzoic acid (60%) and 2,3-dimethoxy-6-[1,2,3]triazol-1-yl-benzoic acid (20%). Data for 2,3-dimethoxy-6-[1,2,3]triazol-2-yl-benzoic acid, MS (ESI): mass calculated for C$_{11}$H$_{11}$N$_3$O$_4$, 249.23; m/z found 250.3 [M+H]$^+$. $^1$H NMR (400 MHz, CD$_3$OD): 7.87 (s, 2H), 7.47 (s, 1H), 7.18 (s, 1H), 3.94 (s, 3H), 3.91 (s, 3H).

Intermediate 61:
2,3-Dimethoxy-6-[1,2,3]triazol-1-yl-benzoic acid

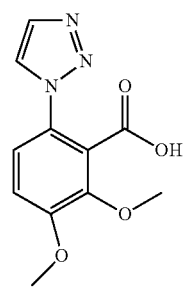 [SMILES: COc1ccc(-n2ccnn2)c(C(=O)O)c1OC]

The title compound was isolated from the procedure used to prepare Intermediate 60 with a 20% yield. MS (ESI): mass calculated for $C_{11}H_{11}N_3O_4$, 249.23; m/z found 250.3 [M+H]$^+$. $^1$H NMR (400 MHz, CD$_3$OD): 8.17 (d, J=1.0 Hz, 1H), 7.82 (d, J=1.0 Hz, 1H), 7.62 (s, 1H), 7.09 (s, 1H), 3.95 (s, 3H), 3.91 (s, 3H).

Intermediate 62: 4-(1H-1,2,3-Triazol-1-yl)nicotinic acid

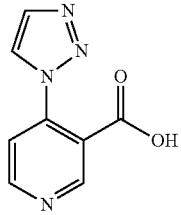 [SMILES: O=C(O)c1cnccc1-n1ccnn1]

The title compound was prepared in a manner analogous to Intermediate 46 substituting 4-chloronicotinic acid for 2-chloro-6-methylnicotinic acid. MS (ESI): mass calculated for $C_{11}H_{10}N_4O_3$, 246.22; m/z found 247.3 [M+H]$^+$. $^1$H NMR (400 MHz, CD$_3$OD): 8.09 (t, J=2.8 Hz, 1H), 7.92-7.86 (m, 3H), 7.66 (dd, J=8.7, 3.3 Hz, 1H), 2.17 (dd, J=2.5, 1.3 Hz, 3H).

Intermediate 63: 4-Fluoro-2-(pyrimidin-2-yl)benzoic acid

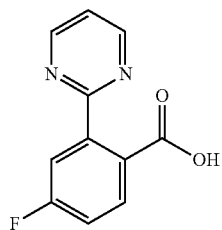 [SMILES: O=C(O)c1ccc(F)cc1-c1ncccn1]

Step A: 2-Iodo-4-fluorobenzonitrile (2.54 g, 10.3 mmol) and 2-tributylstannane pyrimidine (3.69 g, 10.0 mmol) were dissolved in domethoxyethane (18 mL) and treated with tetrakistriphenylphosphine) palladium (0) (578 mg, 0.5 mmol) and copper (I) iodide (95 mg, 0.5 mmol). The reaction was then heated to 160 C. for 90 minutes in the microwave. The reaction was cooled, concentrated under reduced pressure. Chromatography (20-100% EA in hexanes gave the desired product. $^1$H NMR (400 MHz, CDCl$_3$): 8.93 (d, J=4.9 Hz, 2H), 8.14 (dd, J=9.6, 2.7 Hz, 1H), 7.86 (dd, J=8.6, 5.3 Hz, 1H), 7.36 (t, J=4.9 Hz, 1H), 7.32-7.23 (m, 1H).

Step B: 3-Fluoro-2-(pyrimidin-2-yl)benzonitrile (85 mg, 0.4 mmol) was hydrolyzed to the acid in water (1 mL) by addition of 18 M H$_2$SO$_4$ (1 mL). The reaction was heated at 100° C. for 10 min, then cooled to 23° C., and extracted with EtOAc (3×5 mL). The combined organics were dried (Na$_2$SO$_4$) and concentrated under reduced pressure. This material was used crude in subsequent reactions.

Intermediate 64: 4-Methoxy-2-(pyrimidin-2-yl)benzoic acid

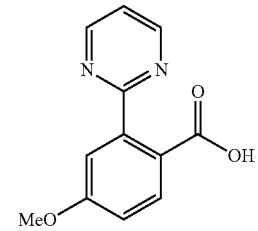 [SMILES: COc1ccc(C(=O)O)c(-c2ncccn2)c1]

Step A: 3-Fluoro-2-(pyrimidin-2-yl)benzonitrile was prepared in a manner analogous to Intermediate 63. $^1$H NMR (400 MHz, CDCl$_3$): 8.93 (d, J=4.9 Hz, 2H), 8.14 (dd, J=9.6, 2.7 Hz, 1H), 7.86 (dd, J=8.6, 5.3 Hz, 1H), 7.36 (t, J=4.9 Hz, 1H), 7.32-7.23 (m, 1H).

Step B: 3-Fluoro-2-(pyrimidin-2-yl)benzonitrile (85 mg, 0.4 mmol) was dissolved in MeOH (20 mL) was treated with 2M aq NaOH (15 mL). The reaction was heated at reflux overnight, the reaction was cooled to room temperature and filtered to remove the solid (amide) and washed with cold MeOH. The filtrate was concentrated to minimum volume and then acidified to pH=3 with 6 N aq. HCl and cooled to 0° C. then filtered and washed with cold water. This material was used crude in subsequent reactions.

Example 1

Biphenyl-2-yl-(3-quinoxalin-2-yl-3,8-diaza-bicyclo[4.2.0]oct-8-yl)-methanone

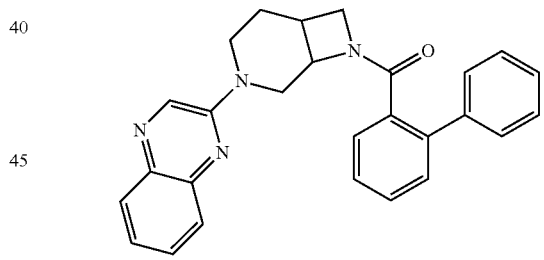

A mixture of trifluoro acetic acid salt of biphenyl-2-yl-(3,8-diaza-bicyclo[4.2.0]oct-8-yl)-methanone (Intermediate 3, 122.0 mg, 0.3 mmol), 2-chloro quinoxaline (60.0 mg, 0.36 mmol), K$_2$CO$_3$ (166 mg, 4 mmol) in DMF (7 mL) was stirred at 80° C. for 18 h. The reaction mixture was partitioned between ethyl acetate (25 mL) and water (120 mL). The organic layers were washed with water (2×30 mL), combined, dried (Na$_2$SO$_4$), filtered and concentrated. The crude residue was purified on HPLC (basic system) to yield the title compound (51 mg, 40%). MS (ESI) mass calcd. for $C_{27}H_{24}N_4O$, 420.51; m/z found, 421 [M+H]$^+$. $^1$H NMR (CDCl$_3$): 8.44 (s, 0.55H), 8.17 (s, 0.45H), 7.97-7.87 (m, 1H), 7.76-7.71 (m, 0.5H), 7.65-7.50 (m, 2H), 7.48-7.30 (m, 7H), 7.09-6.94 (m, 2H), 7.20-7.12 (m, 0.5H), 4.78-4.49 (m, 1H), 4.02-3.78 (m, 1H), 3.76-3.58 (m, 2H), 3.55-3.48 (m, 0.5H), 3.32-3.23 (m, 0.5H), 3.15-2.97 (m, 1H), 2.74-2.39 (m, 1H), 2.12-1.54 (m, 3H).

Example 2

(3-Benzooxazol-2-yl-3,8-diaza-bicyclo[4.2.0]oct-8-yl)-biphenyl-2-yl-methanone

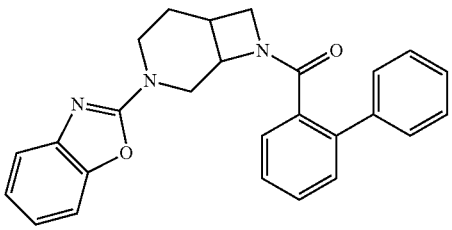 [SMILES: O=C(c1ccccc1-c1ccccc1)N1CC2CCN(c3nc4ccccc4o3)CC21]

The title compound was prepared in a manner analogous to Example 1, substituting 2-chlorobenzoxazole for 2-chloro quinoxaline. MS (ESI) mass calcd. for $C_{26}H_{23}N_3O_2$, 409.48; m/z found, 410 [M+H]$^+$. $^1$H NMR (CDCl$_3$): 7.55-7.29 (m, 8H), 7.24-7.00 (m, 5H), 4.72-3.77 (m, 2.5H), 3.74-3.45 (m, 2.5H), 3.36-3.00 (m, 2H), 2.75-2.38 (m, 1H), 2.03-1.45 (m, 2H).

Example 3

(2,6-Dimethoxy-phenyl)-(3-quinoxalin-6-yl-3,8-diaza-bicyclo[4.2.0]oct-8-yl)-methanone

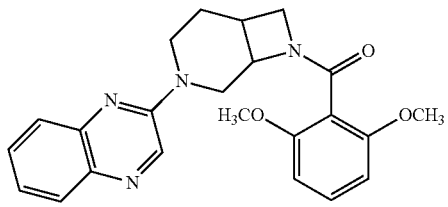 [SMILES: COc1cccc(OC)c1C(=O)N1CC2CCN(c3cnc4ccccc4n3)CC21]

The title compound was prepared in a manner analogous to Example 1, substituting (3,8-diaza-bicyclo[4.2.0]oct-8-yl)-(2,6-dimethoxy-phenyl)-methanone (Intermediate 4) for biphenyl-2-yl-(3,8-diaza-bicyclo[4.2.0]oct-8-yl)-methanone. MS (ESI) mass calcd. for $C_{23}H_{24}N_4O_3$, 404.46; m/z found, 405 [M+H]$^+$. $^1$H NMR (CDCl$_3$): 8.65 (S, 0.36H), 8.28 (S, 0.64H), 7.93-7.83 (m, 1H), 7.70 (dd, J=8.4, 0.9, 0.5H), 7.61-7.51 (m, 1H), 7.41-7.31 (m, 1H), 7.29-7.21 (m, 1H), 7.17 (t, J=8.2, 0.5H), 6.58-6.18 (m, 2H), 5.02-4.81 (m, 0.5H), 4.64 (d, J=8.2, 1H), 4.37-4.29 (m, 0.5H), 4.14-3.98 (m, 1H), 3.94-3.67 (m, 6H), 3.36-3.15 (m, 1H), 3.00-2.82 (m, 3H), 2.28-2.13 (m, 1H), 2.12-1.92 (m, 1H), 1.8 (s br, 1H).

Example 4

[5-(2-Fluoro-phenyl)-2-methyl-thiazol-4-yl]-(3-quinoxalin-6-yl-3,8-diaza-bicyclo[4.2.0]oct-8-yl)-methanone

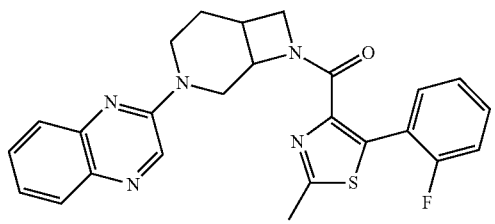 [SMILES: Cc1nc(C(=O)N2CC3CCN(c4cnc5ccccc5n4)CC32)c(-c2ccccc2F)s1]

The title compound was prepared in a manner analogous to Example 1, substituting (3,8-diaza-bicyclo[4.2.0]oct-8-yl)-[4-(2-fluoro-phenyl)-2-methyl-thiazol-5-yl]-methanone (Intermediate 6) for biphenyl-2-yl-(3,8-diaza-bicyclo[4.2.0]oct-8-yl)-methanone. MS (ESI) mass calcd. for $C_{25}H_{22}FN_5OS$, 459.54; m/z found, 460.2 [M+H]$^+$. $^1$H NMR (CDCl$_3$): 8.65 (s, 0.4H), 8.27 (s, 0.6H), 7.90-7.84 (m, 1H), 7.69 (dd, J=8.4, 0.9, 0.4H), 7.60-7.47 (m, 1.6H), 7.41-7.31 (m, 1H), 7.29-7.22 (m, 1.5H), 7.17 (t, J=8.4, 0.5H), 6.54 (d, J=8.3, 1H), 6.21 (d, J=8.4, 1H), 5.05-4.25 (m, 2H), 4.16-4.00 (m, 2H), 3.95-3.65 (m, 2H), 3.24-3.15 (m, 1H), 3.00-2.76 (m, 3H), 2.32-1.68 (m, 3H).

Example 5

Biphenyl-2-yl-[3-(4-phenyl-pyrimidin-2-yl)-3,8-diaza-bicyclo[4.2.0]oct-8-yl]-methanone

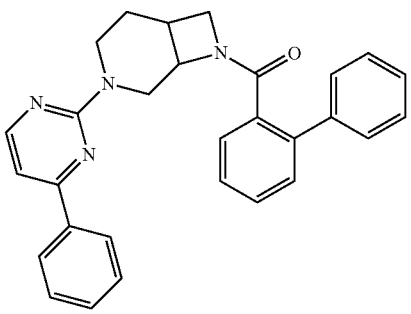 [SMILES: O=C(c1ccccc1-c1ccccc1)N1CC2CCN(c3nccc(-c4ccccc4)n3)CC21]

The title compound was prepared in a manner analogous to Example 1, substituting 2-chloro-4-phenyl-pyrimidine for 2-chloro quinoxaline. MS (ESI) mass calcd. for $C_{29}H_{26}N_4O$, 446.54; m/z found, 447.0 [M+H]$^+$. $^1$H NMR (CDCl$_3$): 8.68-8.28 (m, 1H), 8.02-7.86 (m, 2H), 7.56-7.24 (m, 9H), 7.22-6.88 (m, 4H), 4.06-3.62 (m, 4H), 3.30-3.00 (m, 2H), 2.70-2.34 (m, 2H), 2.08-1.75 (m, 2H).

Example 6

(3-Benzooxazol-2-yl-3,8-diaza-bicyclo[4.2.0]oct-8-yl)-(2,6-dimethoxy-phenyl)-methanone

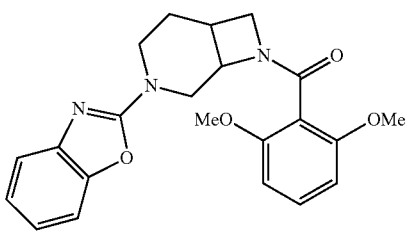 [SMILES: COc1cccc(OC)c1C(=O)N1CC2CCN(c3nc4ccccc4o3)CC21]

The title compound was prepared in a manner analogous to Example 1, substituting the trifluoro acetic acid salt of (3,8-diaza-bicyclo[4.2.0]oct-8-yl)-(2,6-dimethoxy-phenyl)-methanone (Intermediate 4) for biphenyl-2-yl-(3,8-diaza-bicyclo[4.2.0]oct-8-yl)methanone and 2-chlorobenzoxazole for 2-chloro quinoxaline. MS (ESI) mass calcd. for $C_{22}H_{23}N_3O_3$, 393.45; m/z found, 394.0 [M+H]$^+$. $^1$H NMR (CDCl$_3$): 7.54-7.26 (m, 3H), 7.24-7.10 (m, 2H), 7.08-7.02 (m, 0.6H), 6.80-6.73 (m, 0.4H), 6.33-6.22 (m, 1H), 4.74-4.64

(m, 1H), 4.14-3.56 (m, 5H), 3.50-3.35 (m, 1H), 2.99-2.85 (m, 1H), 2.72-2.56 (m, 1H), 2.36-2.20 (m, 5H), 2.03-1.78 (m, 2H).

Example 7

(2,6-Dimethoxy-phenyl)-[3-(4-phenyl-pyrimidin-2-yl)-3,8-diaza-bicyclo[4.2.0]oct-8-yl]-methanone

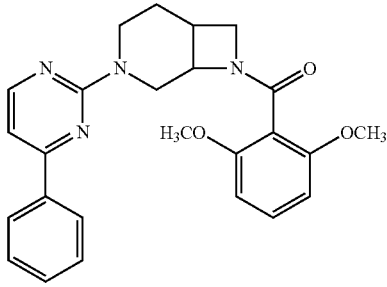 [SMILES: COc1cccc(OC)c1C(=O)N1CC2CCN(c3nccc(-c4ccccc4)n3)CC21]

The title compound was prepared in a manner analogous to Example 1, substituting substituting the trifluoro acetic acid salt of (3,8-diaza-bicyclo[4.2.0]oct-8-yl)-(2,6-dimethoxy-phenyl)-methanone (Intermediate 4) for biphenyl-2-yl-(3,8-diaza-bicyclo[4.2.0]oct-8-yl)-methanone and 2-chloro phenyl pyrimidine for 2-chloro quinoxaline. MS (ESI) mass calcd. for $C_{25}H_{26}N_4O_3$, 430.20; m/z found, 431.3 [M+H]$^+$. $^1$H NMR (CDCl$_3$): 8.64 (d, J=5.3, 0.75H), 8.42 (d, J=5.2, 0.25H), 8.11-8.00 (m, 2H), 7.65 (d, J=5.3, 0.75H), 7.58-7.37 (m, 4H), 7.23-7.11 (m, 0.75H), 6.95 (d, J=5.2, 0.75H), 6.54 (d, J=8.4, 0.75H), 5.33-4.76 (m, 0.5H), 4.60-4.20 (m, 1.5H), 4.09-3.04 (m, 9H), 3.00-2.72 (m, 1H), 2.25-1.80 (m, 2H), 1.75-1.60 (m, 2H).

Example 8

(1R,6S) [3-(4,6-Dimethyl-pyrimidin-2-yl)-3,8-diaza-bicyclo[4.2.0]oct-8-yl]-(2-thiophen-2-yl-phenyl)-methanone

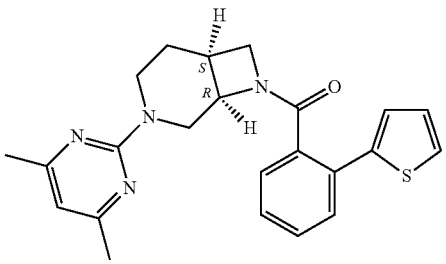

The title compound was prepared in a manner analogous to Example 1, substituting (1R,6S) (3,8-diaza-bicyclo[4.2.0]oct-8-yl)-(2-thiophen-2-yl-phenyl)-methanone (Intermediate 7) for biphenyl-2-yl-(3,8-diaza-bicyclo[4.2.0]oct-8-yl)-methanone and 2-chloro-4,6-dimethyl-pyrimidine for 2-chloro quinoxaline. MS (ESI) mass calcd. for $C_{23}H_{24}N_4OS$, 404.53; m/z found 405.2 [M+H]$^+$. $^1$H NMR (CDCl$_3$) 7.54-7.27 (m, 4H), 7.25-7.12 (m, 2H), 7.07 (dd, J=5.1, 3.6, 0.7H), 6.81-6.75 (m, 0.3H), 6.29 (d, J=17.6, 1H), 4.78-4.54 (m, 0.75H), 4.10-3.55 (m, 4.5H), 3.52-3.33 (m, 0.75H), 3.01-2.90 (m, 0.6H), 2.73-2.56 (m, 1H), 2.30 (d, J=23.8, 6H), 2.10-1.50 (m, 2.4H).

Example 9

8-[(2,5-Dimethylphenyl)sulfonyl]-3-(2-phenylpyrimidin-4-yl)-3,8-diazabicyclo[4.2.0]octane

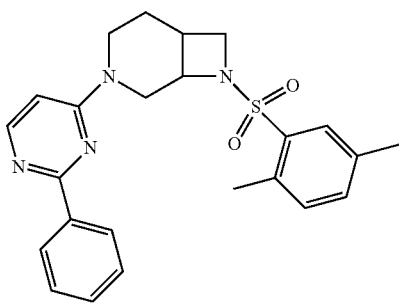 [SMILES: Cc1ccc(C)c(S(=O)(=O)N2CC3CCN(c4ccnc(-c5ccccc5)n4)CC32)c1]

A mixture of 8-(2,4-dimethyl-benzenesulfonyl)-3,8-diaza-bicyclo[4.2.0]octane (Intermediate 5, 68 mg, 0.24 mmol), 2-chloro-4-phenyl pyrimidine (53 mg, 0.28 mmol) and K$_2$CO$_3$ (101 mg, 0.73 mmol) in DMF (5.0 mL) was heated for 18 h at 80° C. The reaction mixture was partitioned between ethyl acetate (25 mL) and water (120 mL). The organic layers were washed with water (2×30 mL), combined, dried (Na$_2$SO$_4$), filtered and concentrated. The crude residue was purified on HPLC (basic system) to yield the title compound (41 mg, 39%). MS (ESI) mass calcd. for $C_{24}H_{26}N_4O_2S$, 434.55; m/z found 435.3 [M+H]$^+$. $^1$H NMR (CDCl$_3$) 8.46-8.18 (m, 1H), 7.94 (s br, 2H), 7.70 (s, 1H), 7.53-7.37 (m, 3H), 6.93 (d, J=5.2, 1H), 6.80-6.55 (m, 2H), 4.77.4.64 (m, 1H), 4.43-4.20 (m, 2H), 4.10-3.78 (m, 2H), 3.55 (dd, J=7.9, 3.2, 1H), 3.22 (dd, J=15.1, 1.9, 1H), 2.91-2.75 (m, 1H), 2.32-2.06 (m, 7H), 2.05-1.88 (m, 1H)

Example 10

2-[8-(2,5-Dimethyl-benzenesulfonyl)-3,8-diaza-bicyclo[4.2.0]oct-3-yl]-quinoxaline

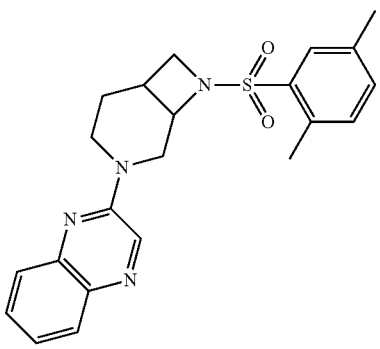 [SMILES: Cc1ccc(C)c(S(=O)(=O)N2CC3CCN(c4cnc5ccccc5n4)CC32)c1]

The title compound was prepared in a manner analogous to Example 9, substituting 2-chloro quinoxaline for 2-chloro-4-phenyl pyrimidine. MS (ESI) mass calcd. for $C_{22}H_{24}N_4O_2S$, 408.52; m/z found 409.0 [M+H]$^+$. $^1$H NMR (CDCl$_3$) 8.26 (s, 1H), 7.88 (d, J=7.9, 1H), 7.68 (d, J=1.1, 1H), 7.63-7.48 (m, 2H), 7.44-7.33 (m, 1H), 6.78 (d, J=6.9, 1H), 6.47 (d, J=7.7, 1H), 4.81-4.68 (m, 1H), 4.35 (t, J=8.2, 1H), 4.15-3.90 (m, 2H), 3.85-3.69 (m, 1H), 3.56 (dd, J=7.9, 3.2, 1H), 3.29 (dd, J=14.7, 1.9, 1H), 2.91-2.73 (m, 1H), 2.31-2.11 (m, 7H), 2.09-1.96 (m, 1H).

Example 11

(1R,6S) Biphenyl-2-yl-[3-(4,6-dimethyl-pyrimidin-2-yl)-3,8-diaza-bicyclo[4.2.0]oct-8-yl]-methanone

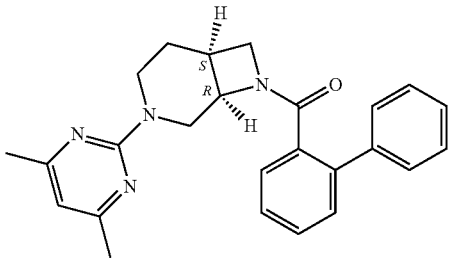

The title compound was prepared in a manner analogous to Example 1, substituting (1R,6S) biphenyl-2-yl-(3,8-diaza-bicyclo[4.2.0]oct-8-yl)-methanone for biphenyl-2-yl-(3,8-diaza-bicyclo[4.2.0]oct-8-yl)-methanone and 2-chloro-4,6-dimethyl-pyrimidine for 2-chloro quinoxaline. MS (ESI) mass calcd. for $C_{25}H_{26}N_4O$, 398.50; m/z found 399.2 [M+H]$^+$. $^1$H NMR (CDCl$_3$): 7.54-7.31 (m, 7H), 7.25-7.11 (m, 2H), 6.33-6.23 (m 1H), 4.64-4.36 (0.5H), 4.00-3.39 (m, 5H), 3.25-2.85 (m, 1.25H), 2.60-2.37 (m, 1.25H), 2.33 (s, 3H), 2.25 (s, 3H), 2.00-1.37 (m, 2H).

Example 12

6-(Biphenyl-2-ylcarbonyl)-3-(4-phenylpyrimidin-2-yl)-3,6-diazabicyclo[3.2.0]heptane

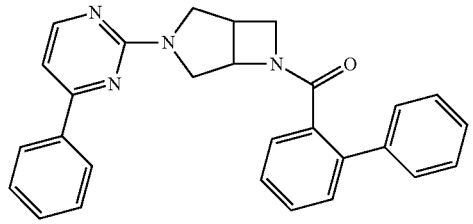 [SMILES: O=C(c1ccccc1-c1ccccc1)N1CC2CN(c3nccc(-c4ccccc4)n3)CC21]

The title compound was prepared from Intermediate 11 in a manner analogous to Example 1. MS (ESI) mass calcd. for $C_{26}H_{24}N_4O$, 432,53; m/z found 433.3 [M+H]$^+$.

Example 13

2-[6-(Biphenyl-2-ylcarbonyl)-3,6-diazabicyclo[3.2.0]hept-3-yl]quinoxaline

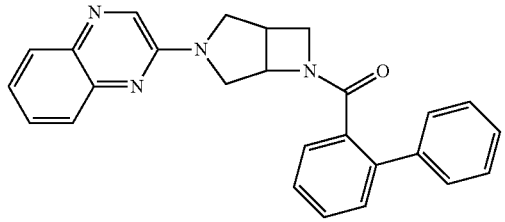 [SMILES: O=C(c1ccccc1-c1ccccc1)N1CC2CN(c3cnc4ccccc4n3)CC21]

The title compound was prepared from Intermediate 8 in a manner analogous to Example 1, MS (ESI) mass calcd. for $C_{26}H_{22}N_4O$, 406.49; m/z found, 407.2 [M+H]$^+$.

Example 14

6-[(2-Bromophenyl)carbonyl]-3-(4,6-dimethylpyrimidin-2-yl)-3,6-diazabicyclo[3.2.0]heptane

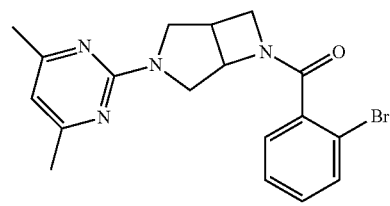 [SMILES: Cc1cc(C)nc(N2CC3CN(C(=O)c4ccccc4Br)C3C2)n1]

The title compound was prepared from Intermediate 9 in a manner analogous to Example 1, MS (ESI) mass calcd. for $C_{18}H_{19}BrN_4O$, 387.28; m/z found, 387.1 [M+H]$^+$.

Example 15

3-(4,6-Dimethylpyrimidin-2-yl)-6-[(2-thiophen-2-ylphenyl)carbonyl]-3,6-diazabicyclo[3.2.0]heptane

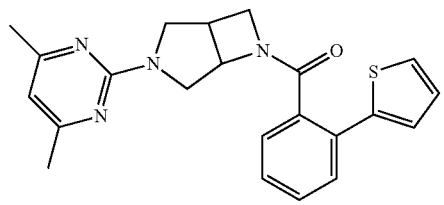 [SMILES: Cc1cc(C)nc(N2CC3CN(C(=O)c4ccccc4-c4cccs4)C3C2)n1]

The title compound was prepared from Intermediate 9 in a manner analogous to Example 1. MS (ESI) mass calcd. for $C_{22}H_{22}N_4OS$, 390.51; m/z found, 391.2 [M+H]$^+$.

Example 16

6-(Biphenyl-2-ylcarbonyl)-3-(4,6-dimethylpyrimidin-2-yl)-3,6-diazabicyclo[3.2.0]heptane

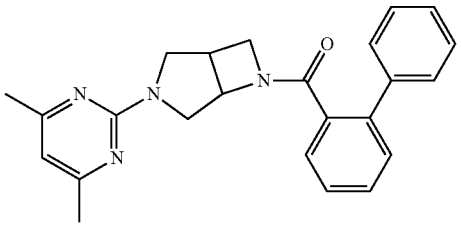 [SMILES: Cc1cc(C)nc(N2CC3CN(C(=O)c4ccccc4-c4ccccc4)C3C2)n1]

The title compound was prepared from Intermediate 9 in a manner analogous to Example 1, substituting biphenyl-2-yl-(3,6-diaza-bicyclo[3.2.0]hept-6-yl)-methanone for biphenyl-2-yl-(3,8-diaza-bicyclo[4.2.0]oct-8-yl)-methanone and 2-chloro-4,6-dimethyl-pyrimidine for 2-chloro quinoxaline. MS (ESI) mass calcd. for $C_{24}H_{24}N_4O$, 384.49; m/z found, 385.2 $[M+H]^+$.

Example 17

6-[(2-Bromophenyl)carbonyl]-3-(4-methylpyrimidin-2-yl)-3,6-diazabicyclo[3.2.0]heptane

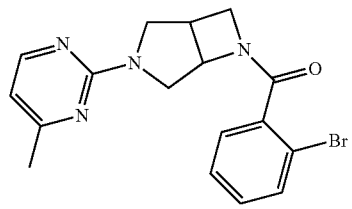 [SMILES: Cc1ccnc(N2CC3CN(C(=O)c4ccccc4Br)C3C2)n1]

The title compound was prepared from Intermediate 10 in a manner analogous to Example 1, substituting 2-bromobenzoic acid chloride for biphenyl-2-carbonyl chloride. MS (ESI) mass calcd. for $C_{17}H_{17}BrN_4O$, 373.26; m/z found, 373.1 $[M+H]^+$

Example 18

3-(4-Methylpyrimidin-2-yl)-6-[(2-thiophen-2-ylphenyl)carbonyl]-3,6-diazabicyclo[3.2.0]heptane

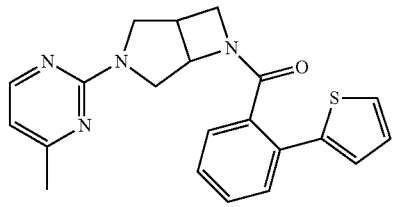 [SMILES: Cc1ccnc(N2CC3CN(C(=O)c4ccccc4-c4cccs4)C3C2)n1]

The title compound was prepared from Intermediate 10 in a manner analogous to Example 1. MS (ESI) mass calcd. for $C_{21}H_{20}N_4OS$, 376.48; m/z found, 377.2 $[M+H]^+$.

Example 19

6-(Biphenyl-2-ylcarbonyl)-3-(4-methylpyrimidin-2-yl)-3,6-diazabicyclo[3.2.0]heptane

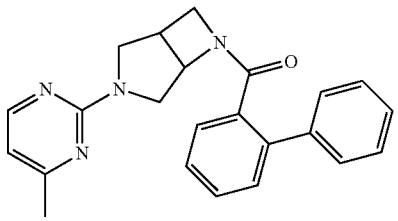 [SMILES: Cc1ccnc(N2CC3CN(C(=O)c4ccccc4-c4ccccc4)C3C2)n1]

The title compound was prepared from Intermediate 10 in a manner analogous to Example 1. MS (ESI) mass calcd. for $C_{23}H_{22}N_4O$, 370.46; m/z found, 371.2 $[M+H]^+$.

Examples 20-27 may be synthesized using the general schemes provided above.

Example 20

[3-(4,6-Dimethyl-pyrimidin-2-yl)-3,6-diaza-bicyclo [3.2.0]hept-6-yl]-(5-fluoro-2-pyrimidin-2-yl-phenyl)-methanone

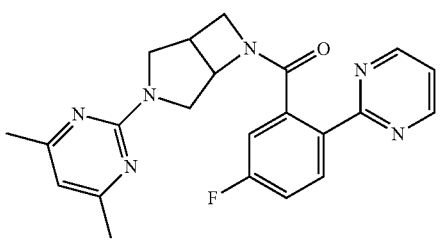 [SMILES: Cc1cc(C)nc(N2CC3CN(C(=O)c4cc(F)ccc4-c4ncccn4)C3C2)n1]

MS (ESI) mass calcd. for $C_{22}H_{21}FN_6O_4$, 404.44.

Example 21

[3-(4,6-Dimethyl-pyrimidin-2-yl)-3,6-diaza-bicyclo [3.2.0]hept-6-yl]-(2-[1,2,3]triazol-2-yl-phenyl)-methanone

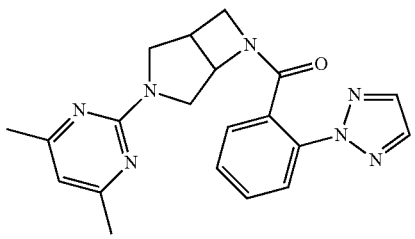 [SMILES: Cc1cc(C)nc(N2CC3CN(C(=O)c4ccccc4-n4nccn4)C3C2)n1]

MS (ESI) mass calcd. for $C_{20}H_{21}N_7O$, 375.43.

Example 22

[3-(4,6-Dimethyl-pyrimidin-2-yl)-3,6-diaza-bicyclo [3.2.0]hept-6-yl]-(2-fluoro-6-[1,2,3]triazol-2-yl-phenyl)-methanone

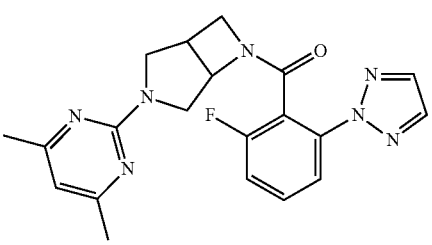 [SMILES: Cc1cc(C)nc(N2CC3CN(C(=O)c4c(F)cccc4-n4nccn4)C3C2)n1]

MS (ESI) mass calcd. for $C_{20}H_{20}FN_7O$, 393.17.

Example 23

[3-(4,6-Dimethyl-pyrimidin-2-yl)-3,6-diaza-bicyclo[3.2.0]hept-6-yl]-(3-fluoro-2-[1,2,3]triazol-2-yl-phenyl)-methanone

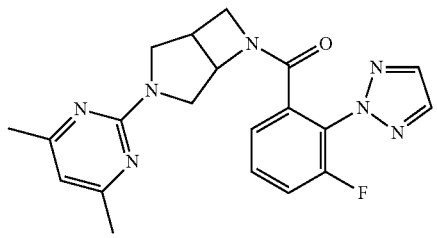 [SMILES: Cc1cc(C)nc(N2CC3CN(C(=O)c4cccc(F)c4-n4nccn4)C3C2)n1]

MS (ESI) mass calcd. for $C_{20}H_{20}FN_7O$, 393.17.

Example 24

[3-(4,6-Dimethoxy-pyrimidin-2-yl)-3,6-diaza-bicyclo[3.2.0]hept-6-yl]-(2-fluoro-6-[1,2,3]triazol-2-yl-phenyl)-methanone

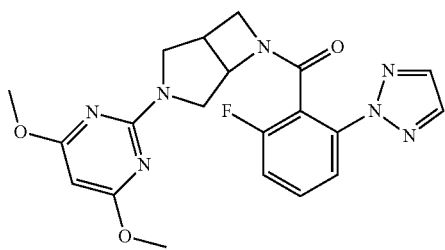 [SMILES: COc1cc(OC)nc(N2CC3CN(C(=O)c4c(F)cccc4-n4nccn4)C3C2)n1]

MS (ESI) mass calcd. for $C_{20}H_{20}FN_7O_3$, 425.42.

Example 25

(2-Fluoro-6-[1,2,3]triazol-2-yl-phenyl)-[3-(4-methoxy-pyrimidin-2-yl)-3,6-diaza-bicyclo[3.2.0]hept-6-yl]-methanone

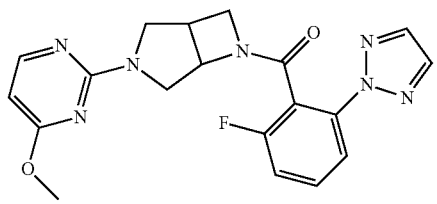 [SMILES: COc1ccnc(N2CC3CN(C(=O)c4c(F)cccc4-n4nccn4)C3C2)n1]

MS (ESI) mass calcd. for $C_{19}H_{18}FN_7O_2$, 395.39.

Example 26

[3-(3,6-Dimethyl-pyrazin-2-yl)-3,6-diaza-bicyclo[3.2.0]hept-6-yl]-(2-fluoro-6-[1,2,3]triazol-2-yl-phenyl)-methanone

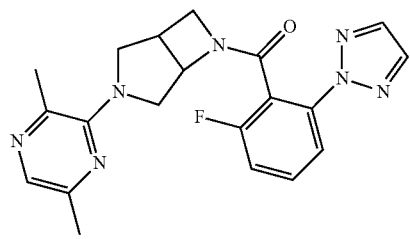 [SMILES: Cc1cnc(C)c(N2CC3CN(C(=O)c4c(F)cccc4-n4nccn4)C3C2)n1]

MS (ESI) mass calcd. for $C_{20}H_{20}FN_7O$, 393.42.

Example 27

(2-Fluoro-6-[1,2,3]triazol-2-yl-phenyl)-[3-(4-methyl-6-trifluoromethyl-pyrimidin-2-yl)-3,6-diaza-bicyclo[3.2.0]hept-6-yl]-methanone

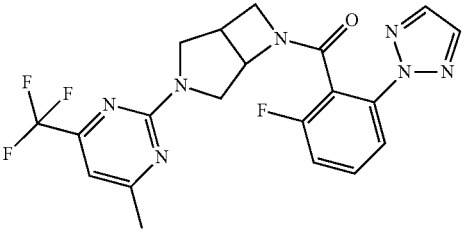 [SMILES: Cc1cc(C(F)(F)F)nc(N2CC3CN(C(=O)c4c(F)cccc4-n4nccn4)C3C2)n1]

MS (ESI) mass calcd. for $C_{20}H_{17}F_4N_7O$, 447.14.

Example 28

(1S,6R)-3-(4,6-Dimethylpyrimidin-2-yl)-8-{[2-(3-methyl-1,2,4-oxadiazol-5-yl)phenyl]carbonyl}-3,8-diazabicyclo[4.2.0]octane

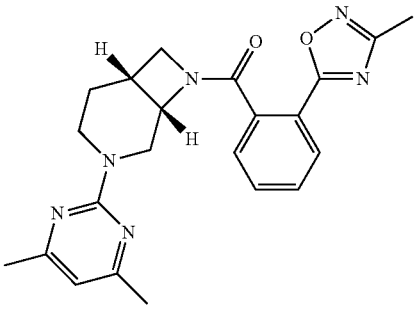

A mixture of Intermediate 12 (50 mg, 0.17 mmol), 2-chloro-4,6-dimethylpyrimidine (24 mg, 0.17 mmol) and DIPEA (0.87 mL, 0.5 mmol) in ACN (1 mL) was heated in the microwave at 200° C. for 90 min. The mixture was concentrated in vacuo and was purified on a Prep Agilent system with a XBridge $C_{18}$ OBD 50×100 mm column eluting with 5 to 99% 0.05% $NH_4OH$ in $H_2O$/ACN over 17 min to afford the desired product as a colorless foam (41 mg, 60%). MS (ESI) mass calculated for $C_{22}H_{24}N_6O_2$, 404.20; m/z found, 405.2. $^1$H NMR (500 MHz, $CDCl_3$): 8.12-8.03 (m, 1H), 7.59-7.49 (m, 2H), 7.41-7.36 (m, 1H), 6.31-6.26 (m, 1H), 4.41-4.23 (m, 3H), 4.11-4.05 (m, 1H), 4.05-3.78 (m, 2H), 3.68-3.64 (m, 0H), 3.05-2.83 (m, 2H), 2.46-2.40 (m, 3H), 2.34-2.24 (m, 6H), 2.15-2.04 (m, 1H), 2.00-1.86 (m, 1H).

Example 29

(1S,6R)-3-(5-Chloro-4-methylpyrimidin-2-yl)-8-{[2-(3-methyl-1,2,4-oxadiazol-5-yl)phenyl]carbonyl}-3,8-diazabicyclo[4.2.0]octane

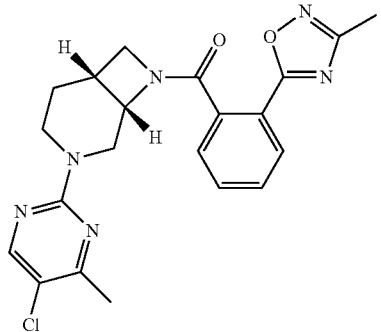 [SMILES: Cc1noc(-c2ccccc2C(=O)N2C[C@H]3CCN(c4ncc(Cl)c(C)n4)C[C@H]32)n1]

The title compound was prepared in a manner analogous to Example 28 substituting Intermediate 13 for 2-chloro-4,6-dimethylpyrimidine. MS (ESI) mass calculated for $C_{21}H_{21}ClN_6O_2$, 424.14; m/z found, 425.1. $^1$H NMR (500 MHz, CDCl$_3$): 8.19-8.03 (m, 2H), 7.61-7.49 (m, 2H), 7.37-7.28 (m, 1H), 4.44-4.31 (m, 2H), 4.19-4.04 (m, 1H), 3.98-3.74 (m, 3H), 3.68-3.63 (m, 0H), 3.06-2.84 (m, 2H), 2.48-2.35 (m, 6H), 2.17-2.05 (m, 1H), 2.01-1.86 (m, 1H).

Example 30

(1S,6R)-3-(5-Chloro-4,6-dimethylpyrimidin-2-yl)-8-{[2-(3-methyl-1,2,4-oxadiazol-5-yl)phenyl]carbonyl}-3,8-diazabicyclo[4.2.0]octane

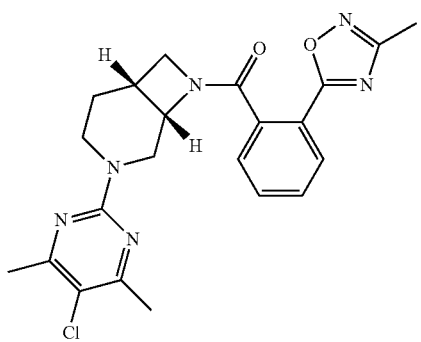

The title compound was prepared in a manner analogous to Example 28 substituting Intermediate 14 for 2-chloro-4,6-dimethylpyrimidine. MS (ESI) mass calculated for $C_{22}H_{23}ClN_6O_2$, 438.16; m/z found, 439.2. $^1$H NMR (500 MHz, CDCl$_3$): 8.14-8.03 (m, 1H), 7.61-7.50 (m, 2H), 7.38-7.32 (m, 1H), 4.42-4.30 (m, 2H), 4.20-4.13 (m, 1H), 4.10-4.04 (m, 1H), 4.00-3.73 (m, 2H), 3.03-2.82 (m, 2H), 2.47-2.35 (m, 9H), 2.14-2.03 (m, 1H), 2.00-1.85 (m, 1H).

Example 31

(1S,6R)-8-{[2-(3-Methyl-1,2,4-oxadiazol-5-yl)phenyl]carbonyl}-3-(4,5,6-trimethylpyrimidin-2-yl)-3,8-diazabicyclo[4.2.0]octane

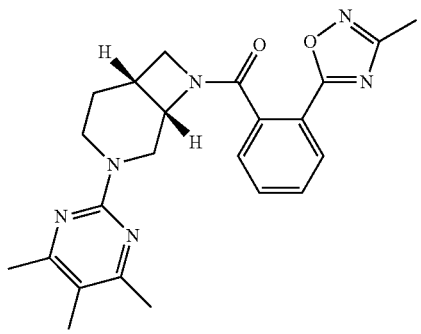

The title compound was prepared in a manner analogous to Example 28 substituting Intermediate 17 for 2-chloro-4,6-dimethylpyrimidine. MS (ESI) mass calculated for $C_{23}H_{26}N_6O_2$, 418.21; m/z found, 419.2. $^1$H NMR (500 MHz, CDCl$_3$): 8.12-8.02 (m, 1H), 7.59-7.48 (m, 2H), 7.42-7.36 (m, 1H), 4.39-4.23 (m, 3H), 4.11-4.04 (m, 1H), 4.03-3.73 (m, 2H), 3.04-2.82 (m, 2H), 2.46-2.39 (m, 3H), 2.38-2.26 (m, 6H), 2.13-2.03 (m, 4H), 1.99-1.84 (m, 1H).

Example 32

(1S,6R)-3-(4,6-Dimethylpyrimidin-2-yl)-8-{[2-fluoro-6-(3-methyl-1,2,4-oxadiazol-5-yl)phenyl]carbonyl}-3,8-diazabicyclo[4.2.0]octane

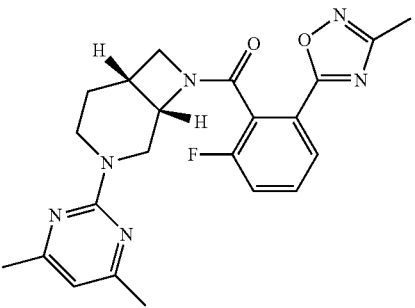

The title compound was prepared in a manner analogous to Intermediate 12, Step B substituting Intermediate 34 for (1R,6S) 3,8-diaza-bicyclo[4.2.0]octane-3-carboxylic acid tert-butyl ester and Intermediate 16 for 2-(3-methyl-1,2,4-oxadiazol-5-yl)benzoic acid. MS (ESI) mass calculated for $C_{22}H_{23}FN_6O_2$, 422.19; m/z found, 423.2.

Example 33

N,N-Dimethyl-6-[(1S,6R)-8-{[2-(3-methyl-1,2,4-oxadiazol-5-yl)phenyl]carbonyl}-3,8-diazabicyclo[4.2.0]oct-3-yl]pyrimidin-4-amine

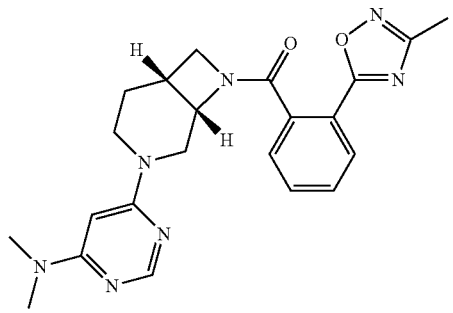

A mixture of Intermediate 12 (50 mg, 0.17 mmol), 2-chloro-4,6-dimethylpyrimidine (24 mg, 0.17 mmol) and DIPEA (0.87 mL, 0.5 mmol) in ACN (1 mL) was heated in the microwave at 200° C. for 2 h. The mixture was concentrated in vacuo and chromatography (Hex to 100% EtOAc/Hex) to afford the desired product as a pale yellow foam (39 mg, 55%). MS (ESI) mass calculated for $C_{22}H_{25}N_7O_2$, 419.2; m/z found, 420.2. $^1$H NMR (500 MHz, CDCl$_3$): 8.15 (s, 1H), 8.12-8.04 (m, 1H), 7.59-7.50 (m, 2H), 7.25-7.17 (m, 1H), 5.22 (s, 1H), 4.44-4.33 (m, 2H), 4.11-3.99 (m, 1H), 3.94-3.73

(m, 2H), 3.68-3.60 (m, 1H), 3.11-3.05 (m, 6H), 3.02-2.86 (m, 2H), 2.45-2.42 (m, 3H), 2.22-1.97 (m, 2H).

Example 34

(1S,6R)-3-(5-Fluoro-4,6-dimethylpyrimidin-2-yl)-8-{[2-(3-methyl-1,2,4-oxadiazol-5-yl)phenyl]carbonyl}-3,8-diazabicyclo[4.2.0]octane

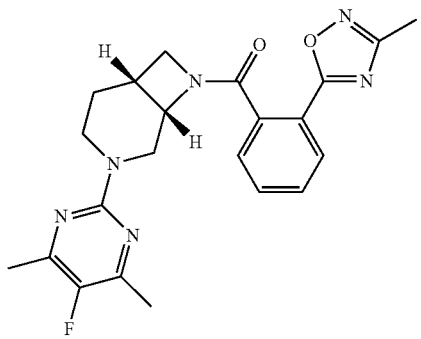

The title compound was prepared in a manner analogous to Example 28 substituting Intermediate 18 for 2-chloro-4,6-dimethylpyrimidine. MS (ESI) mass calculated for $C_{22}H_{23}FN_6O_2$, 422.19; m/z found, 423.2. $^1$H NMR (500 MHz, CDCl$_3$): 8.12-8.03 (m, 1H), 7.60-7.50 (m, 2H), 7.38-7.32 (m, 1H), 4.41-4.30 (m, 1H), 4.16-4.04 (m, 2H), 3.98-3.71 (m, 2H), 3.03-2.81 (m, 2H), 2.45-2.40 (m, 3H), 2.36-2.29 (m, 6H), 2.14-1.84 (m, 3H).

Example 35

(6-Methyl-2-(1H-1,2,3-triazol-1-yl)pyridin-3-yl)((1S,6R)-3-(4,5,6-trimethylpyrimidin-2-yl)-3,8-diazabicyclo[4.2.0]octan-8-yl)methanone

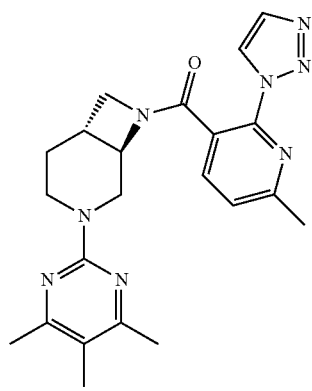

To a microwave safe vial was added (1S,6R)-3,8-diazabicyclo[4.2.0]octan-8-yl(6-methyl-2-(1H-1,2,3-triazol-1-yl)pyridin-3-yl)methanone (80 mg, 0.27 mmol), 2-chloro-4,5,6-trimethylpyrimidine (84 mg, 0.54 mmol), ACN (3 mL) and DIPEA (0.093 mL, 0.54 mmol). The resulting mixture was heated to 180° C. in a microwave reactor. After 2 hours the mixture was cooled to ambient temperature and concentrated under reduced pressure. The crude residue was purified by reverse-phase HPLC (acidic) to yield the title compound (60.3 mg, 42%) as the TFA salt. MS (ESI) mass calcd. for $C_{22}H_{26}N_8O$, 418.2; m/z found, 419.1 [M+H]$^+$. $^1$H NMR (500 MHz, CDCl$_3$): 8.44-8.32 (m, 1H), 7.82-7.72 (m, 2H), 7.22-7.16 (m, 1H), 4.52-4.46 (m, 1H), 4.30 (dd, J=10.0, 9.0 Hz, 1H), 4.04 (tt, J=9.6, 4.8 Hz, 1H), 3.99-3.92 (m, 1H), 3.89-3.57 (m, 2H), 3.13-2.83 (m, 2H), 2.65-2.57 (m, 3H), 2.39-2.31 (m, 6H), 2.15-2.02 (m, 4H), 1.99-1.81 (m, 1H).

Example 36

(1S,6R)-3-(5-Fluoro-4-methylpyrimidin-2-yl)-8-{[6-methyl-2-(1H-1,2,3-triazol-1-yl)pyridin-3-yl]carbonyl}-3,8-diazabicyclo[4.2.0]octane

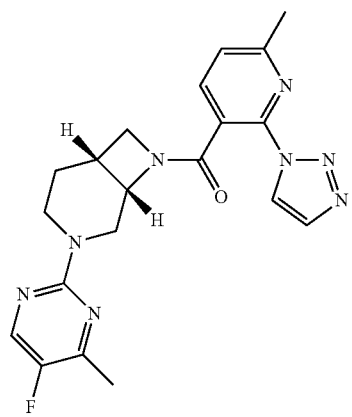 [SMILES: Cc1ccc(C(=O)N2C[C@H]3CCN(c4ncc(F)c(C)n4)C[C@H]32)c(-n2ccnn2)n1]

The title compound was prepared in a manner analogous to Example 35 substituting 2-chloro-5-fluoro-4-methylpyrimidine for 2-chloro-4,5,6-trimethylpyrimidine. MS (ESI) mass calcd. for $C_{20}H_{21}FN_8O$, 408.4; m/z found, 409.2 [M+H]$^+$. $^1$H NMR (500 MHz, CDCl$_3$): 8.46-8.32 (m, 1H), 8.11-8.01 (m, 1H), 7.81-7.74 (m, 1H), 7.67-7.50 (m, 1H), 7.20 (dd, J=7.7, 2.5 Hz, 1H), 4.75-4.48 (m, 1H), 4.38-4.29 (m, 1H), 3.98 (ddd, J=15.5, 13.0, 6.6 Hz, 2H), 3.86-3.60 (m, 2H), 3.17-3.11 (m, 1H), 3.08-2.85 (m, 1H), 2.65-2.57 (m, 3H), 2.41-2.33 (m, 3H), 2.17-2.02 (m, 1H), 2.01-1.83 (m, 1H).

Example 37

(1S,6R)-3-(4,5-Dimethylpyrimidin-2-yl)-8-{[6-methyl-2-(1H-1,2,3-triazol-1-yl)pyridin-3-yl]carbonyl}-3,8-diazabicyclo[4.2.0]octane

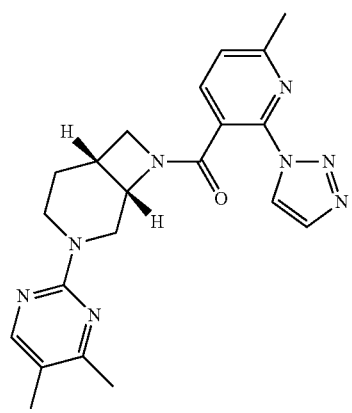 [SMILES: Cc1ccc(C(=O)N2C[C@H]3CCN(c4ncc(C)c(C)n4)C[C@H]32)c(-n2ccnn2)n1]

The title compound was prepared in a manner analogous to Example 35 substituting 2-chloro-4,5-dimethylpyrimidine for 2-chloro-4,5,6-trimethylpyrimidine. MS (ESI) mass calcd. for $C_{21}H_{24}N_8O$, 404.5; m/z found, 405.2 [M+H]+. 1H NMR (500 MHz, CDCl3): 8.44-8.33 (m, 1H), 8.04-8.00 (m, 1H), 7.81-7.74 (m, 1H), 7.74-7.48 (m, 1H), 7.22-7.16 (m, 1H), 4.54-4.28 (m, 2H), 4.07-3.92 (m, 2H), 3.90-3.60 (m, 2H), 3.12 (dd, J=14.9, 2.0 Hz, 1H), 3.08-2.85 (m, 1H), 2.64-2.57 (m, 3H), 2.38-2.31 (m, 3H), 2.15-2.04 (m, 4H), 2.00-1.84 (m, 1H).

Example 38

(1S,6R)-3-(4,6-Dimethylpyrimidin-2-yl)-8-{[6-methyl-2-(1H-1,2,3-triazol-1-yl)pyridin-3-yl]carbonyl}-3,8-diazabicyclo[4.2.0]octane

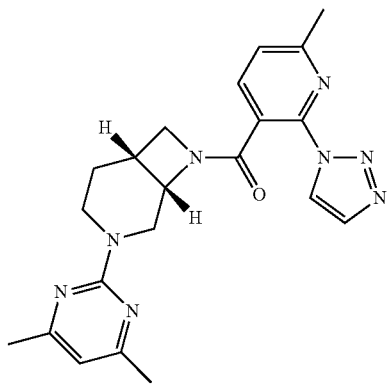 [SMILES: Cc1cc(C)nc(N2CC[C@@H]3CN(C(=O)c4ccc(C)nc4-n4ccnn4)[C@@H]3C2)n1]

The title compound was prepared in a manner analogous to Example 35 substituting 2-choro-4,6-dimethylpyrimidine for 2-chloro-4,5,6-trimethylpyrimidine. MS (ESI) mass calcd. for $C_{21}H_{24}N_8O$, 404.5; m/z found, 405.2 [M+H]+. 1H NMR (500 MHz, CDCl3): 8.45-8.32 (m, 1H), 7.81-7.72 (m, 2H), 7.22-7.15 (m, 1H), 6.97 (5, 1H), 6.34-6.27 (m, 1H), 4.56-4.50 (m, 1H), 4.35-4.26 (m, 1H), 4.11-3.93 (m, 2H), 3.85-3.71 (m, 1H), 3.20-3.08 (m, 1H), 3.07-2.84 (m, 1H), 2.64-2.57 (m, 3H), 2.35-2.25 (m, 6H), 2.15-1.90 (m, 2H).

Example 39

(1S,6R)-8-{[6-Methyl-2-(1H-1,2,3-triazol-1-yl)pyridin-3-yl]carbonyl}-3-[4-(trifluoromethyl)pyrimidin-2-yl]-3,8-diazabicyclo[4.2.0]octane

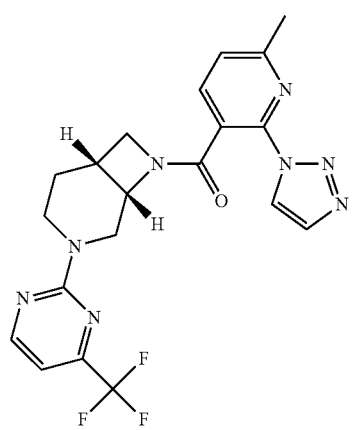 [SMILES: Cc1ccc(C(=O)N2C[C@H]3CCN(c4nccc(C(F)(F)F)n4)C[C@H]32)c(-n2ccnn2)n1]

The title compound was prepared in a manner analogous to Example 35 substituting 2-chloro-4-trifluoromethylpyrimidine for 2-chloro-4,5,6-trimethylpyrimidine. MS (ESI) mass calcd. for $C_{20}H_{19}F_3N_8O$, 444.4; m/z found, 445.2 [M+H]+.

Example 40

6-Chloro-2-[(1S,6R)-8-{[6-methyl-2-(1H-1,2,3-triazol-1-yl)pyridin-3-yl]carbonyl}-3,8-diazabicyclo[4.2.0]oct-3-yl]-1,3-benzoxazole

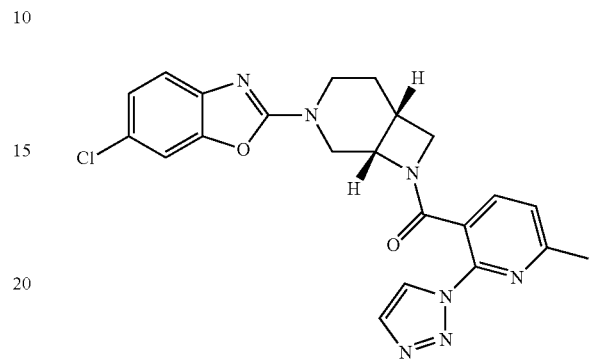

The title compound was prepared in a manner analogous to Example 35 substituting 2,6-dichlorobenzo[d]oxazole for 2-chloro-4,5,6-trimethylpyrimidine. MS (ESI) mass calcd. for $C_{22}H_{20}ClN_7O_2$, 449.9; m/z found, 450.2 [M+H]+. 1H NMR (500 MHz, CDCl3): 8.48-8.37 (m, 1H), 7.77 (d, J=3.3 Hz, 1H), 7.68-7.44 (m, 1H), 7.33 (dd, J=10.5, 1.9 Hz, 1H), 7.24-7.13 (m, 2H), 7.03-6.95 (m, 1H), 4.94-4.35 (m, 2H), 4.12-3.94 (m, 2H), 3.90-3.74 (m, 2H), 3.71-3.30 (m, 1H), 3.12-2.93 (m, 1H), 2.67-2.56 (m, 3H), 2.24-2.11 (m, 1H), 2.06-1.90 (m, 1H).

Example 41

(1S,6R)-8-{[6-Methyl-2-(1H-1,2,3-triazol-1-yl)pyridin-3-yl]carbonyl}-3-[4-(trifluoromethyl)pyridin-2-yl]-3,8-diazabicyclo[4.2.0]octane

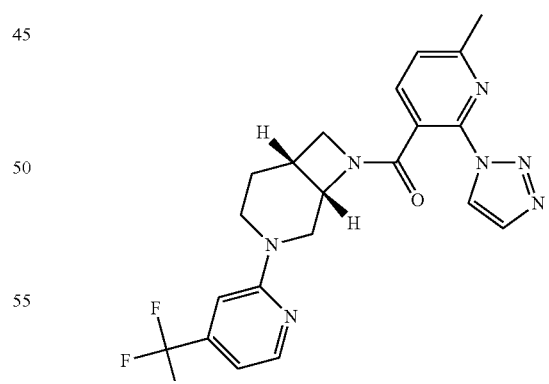

The title compound was prepared in a manner analogous to Example 35 substituting 2-chloro-4-trifluoromethylpyridine for 2-chloro-4,5,6-trimethylpyrimidine. MS (ESI) mass calcd. for $C_{21}H_{20}F_3N_7O$, 443.4; m/z found, 444.2 [M+H]+. 1H NMR (500 MHz, CDCl3): 8.46-8.35 (m, 1H), 8.35-8.23 (m, 1H), 7.81-7.73 (m, 1H), 7.46 (d, 1H), 7.21-7.11 (m, 1H), 6.82-6.56 (m, 2H), 4.96-4.12 (m, 3H), 4.05-3.93 (m, 1H), 3.90-3.79 (m, 1H), 3.78-3.56 (m, 2H), 3.08-2.88 (m, 1H), 2.64-2.57 (m, 3H), 2.29-2.10 (m, 1H), 2.08-1.91 (m, 1H).

Example 42

(1S,6R)-3-(4-Methylpyridin-2-yl)-8-{[6-methyl-2-(1H-1,2,3-triazol-1-yl)pyridin-3-yl]carbonyl}-3,8-diazabicyclo[4.2.0]octane

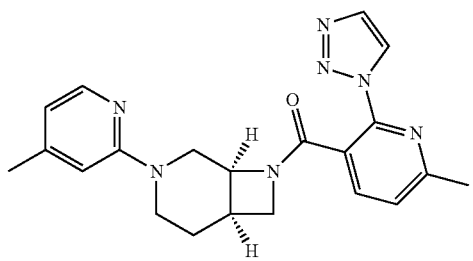

The title compound was prepared in a manner analogous to Example 35 substituting 2-chloro-4-methylpyridine for 2-chloro-4,5,6-trimethylpyrimidine. MS (ESI) mass calcd. for $C_{21}H_{23}N_7O$, 389.5; m/z found, 390.2 [M+H]$^+$. $^1$H NMR (400 MHz, CDCl$_3$): 8.50-8.38 (m, 1H), 8.09-8.01 (m, 1H), 7.86-7.77 (m, 1H), 7.73-7.64 (m, 1H), 7.25-6.58 (m, 3H), 5.12-4.94 (m, 1H), 4.48-4.34 (m, 1H), 4.17-3.96 (m, 2H), 3.93-3.82 (m, 1H), 3.74-3.62 (m, 2H), 3.08-2.91 (m, 1H), 2.61 (s, 3H), 2.41 (s, 3H), 2.29-2.03 (m, 2H).

Example 43

(1S,6R)-3-(4,6-Dimethylpyrimidin-2-yl)-8-{[5-methoxy-2-(2H-1,2,3-triazol-2-yl)phenyl]carbonyl}-3,8-diazabicyclo[4.2.0]octane

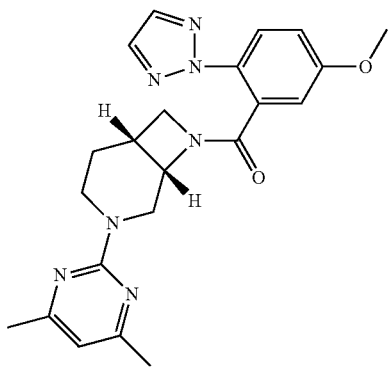

The title compound was prepared in a manner analogous to Example 35 substituting Intermediate 27 for Intermediate 25 and 2-chloro-4,6-dimethylpyrimidine for 2-chloro-4,5,6-trimethylpyrimidine. MS (ESI) mass calcd. for $C_{22}H_{25}N_7O_2$, 419.5; m/z found, 420.2 [M+H]$^+$. $^1$H NMR (500 MHz, CDCl$_3$): 7.91-7.78 (m, 1H), 7.78-7.69 (m, 2H), 7.10-7.00 (m, 1H), 6.87-6.76 (m, 1H), 6.55-6.39 (m, 1H), 4.86-4.66 (m, 1H), 4.30-4.16 (m, 1H), 4.07-3.86 (m, 4H), 3.86-3.77 (m, 3H), 3.59-3.21 (m, 1H), 2.99-2.78 (m, 1H), 2.63-2.33 (m, 6H), 2.22-1.91 (m, 2H).

Example 44

(1S,6R)-3-(5-Fluoro-4-methylpyrimidin-2-yl)-8-{[5-methoxy-2-(2H-1,2,3-triazol-2-yl)phenyl]carbonyl}-3,8-diazabicyclo[4.2.0]octane

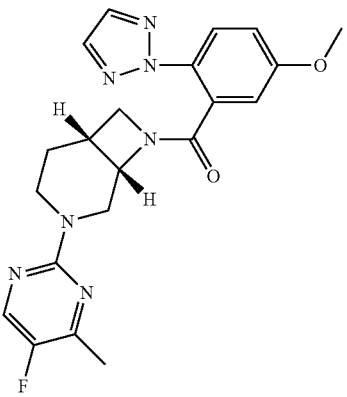 [SMILES: COc1ccc(-n2nccn2)c(C(=O)N2C[C@H]3CCN(c4ncc(F)c(C)n4)C[C@H]32)c1]

The title compound was prepared in a manner analogous to Example 43 substituting 2-chloro-5-fluoro-4-methylpyrimidine for 2-chloro-4,6-dimethylpyrimidine. MS (ESI) mass calcd. for $C_{21}H_{22}FN_7O_2$, 423.5; m/z found, 424.2 [M+H]$^+$. $^1$H NMR (500 MHz, CDCl$_3$): 8.28-8.09 (m, 1H), 7.91-7.77 (m, 1H), 7.76-7.67 (m, 2H), 7.08-7.00 (m, 1H), 6.76 (dd, J=12.1, 2.8 Hz, 1H), 4.84-4.71 (m, 1H), 4.26-3.71 (m, 8H), 3.15-3.06 (m, 1H), 2.92-2.77 (m, 1H), 2.49-2.34 (m, 3H), 2.15-1.83 (m, 2H).

Example 45

(1S,6R)-8-{[5-Methoxy-2-(2H-1,2,3-triazol-2-yl)phenyl]carbonyl}-3-(4,5,6-trimethylpyrimidin-2-yl)-3,8-diazabicyclo[4.2.0]octane

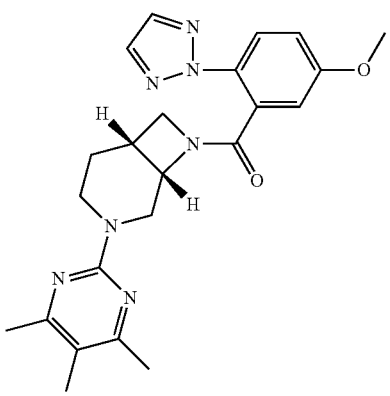

The title compound was prepared in a manner analogous to Example 43 substituting 2-chloro-4,5,6-trimethylpyrimidine for 2-chloro-4,6-dimethylpyrimidine. MS (ESI) mass calcd. for $C_{23}H_{27}N_7O_2$, 433.5; m/z found, 434.5 [M+H]$^+$. $^1$H NMR (500 MHz, CDCl$_3$): 7.91-7.79 (m, 1H), 7.78-7.68 (m, 2H), 7.09-7.00 (m, 1H), 6.85-6.76 (m, 1H), 4.84-4.65 (m, 1H), 4.44-4.13 (m, 2H), 4.06-3.88 (m, 3H), 3.87-3.76 (m, 3H), 3.59-3.20 (m, 1H), 3.00-2.75 (m, 1H), 2.63-2.39 (m, 6H), 2.20-1.90 (m, 5H).

Example 46

2-[(1S,6R)-8-{[5-Methoxy-2-(2H-1,2,3-triazol-2-yl)phenyl]carbonyl}-3,8-diazabicyclo[4.2.0]oct-3-yl]-4-methyl-6,7-dihydro-5H-cyclopenta[d]pyrimidine

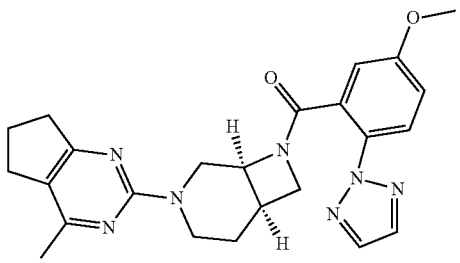 [SMILES: COc1ccc(-n2nccn2)c(C(=O)N2C[C@H]3CCN(c4nc(C)c5c(n4)CCC5)C[C@H]32)c1]

The title compound was prepared in a manner analogous to Example 43 substituting 2-chloro-4-methyl-6,7-dihydro-5H-cyclopenta[d]pyrimidine for 2-chloro-4,6-dimethylpyrimidine. MS (ESI) mass calcd. for $C_{24}H_{27}N_7O_2$, 445.5; m/z found, 446.2 [M+H]$^+$. $^1$H NMR (500 MHz, CDCl$_3$): 7.91-7.78 (m, 1H), 7.78-7.69 (m, 2H), 7.08-7.01 (m, 1H), 6.85-6.78 (m, 1H), 4.84-4.66 (m, 1H), 4.46-3.87 (m, 5H), 3.87-3.77 (m, 3H), 3.59-3.20 (m, 1H), 3.12-2.90 (m, 2H), 2.88-2.76 (m, 3H), 2.48 (d, J=33.7 Hz, 3H), 2.25-1.89 (m, 4H).

Example 47

2-[(1S,6R)-8-{[5-Methoxy-2-(2H-1,2,3-triazol-2-yl)phenyl]carbonyl}-3,8-diazabicyclo[4.2.0]oct-3-yl]pyrimidin-4-amine

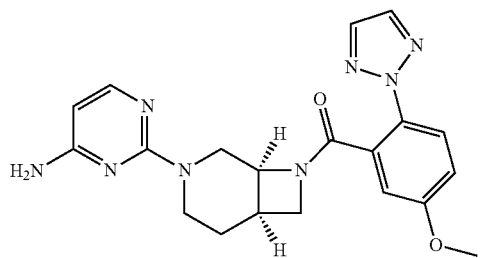 [SMILES: COc1ccc(-n2nccn2)c(C(=O)N2C[C@H]3CCN(c4nccc(N)n4)C[C@H]32)c1]

The title compound was prepared in a manner analogous to Example 43 substituting 4-amino-2-chloro-pyrimidine for 2-chloro-4,6-dimethylpyrimidine. MS (ESI) mass calcd. for $C_{20}H_{22}N_8O_2$, 406.5; m/z found, 407.2 [M+H]$^+$.

Example 48

(1S,6R)-8-{[5-Methoxy-2-(2H-1,2,3-triazol-2-yl)phenyl]carbonyl}-3-[4-(trifluoromethyl)pyrimidin-2-yl]-3,8-diazabicyclo[4.2.0]octane

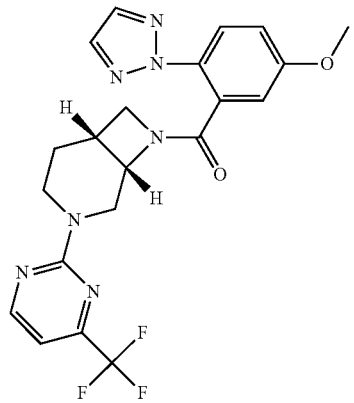 [SMILES: COc1ccc(-n2nccn2)c(C(=O)N2C[C@H]3CCN(c4nccc(C(F)(F)F)n4)C[C@H]32)c1]

The title compound was prepared in a manner analogous to Example 43 substituting 2-chloro-4-trifluoromethylpyrimidine for 2-chloro-4,6-dimethylpyrimidine. MS (ESI) mass calcd. for $C_{21}H_{20}F_3N_7O_2$, 459.4; m/z found, 460.2 [M+H]$^+$. $^1$H NMR (500 MHz, CDCl$_3$): 8.59-8.29 (m, 1H), 7.90-7.74 (m, 1H), 7.74-7.59 (m, 2H), 7.09-6.96 (m, 1H), 6.85-6.69 (m, 2H), 4.31-3.85 (m, 5H), 3.83-3.62 (m, 4H), 3.55-3.06 (m, 1H), 2.95-2.79 (m, 1H), 2.14-1.78 (m, 2H).

Example 49

6-[(1S,6R)-8-{[5-Methoxy-2-(2H-1,2,3-triazol-2-yl)phenyl]carbonyl}-3,8-diazabicyclo[4.2.0]oct-3-yl]-N,N-dimethylpyrimidin-4-amine

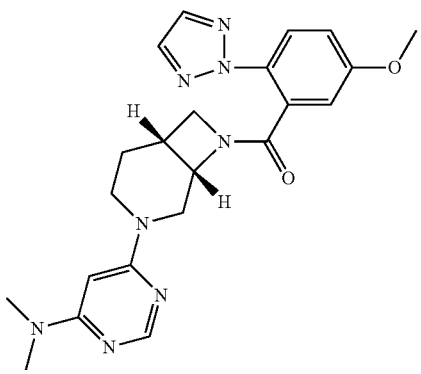

The title compound was prepared in a manner analogous to Example 43 substituting 6-chloro-N,N-dimethylpyrimidin-4-amine for 2-chloro-4,6-dimethylpyrimidine. MS (ESI) mass calcd. for $C_{22}H_{26}N_8O_2$, 434.5; m/z found, 435.2 [M+H]$^+$. $^1$H NMR (500 MHz, CDCl$_3$): 8.39-8.22 (m, 1H), 7.95-7.78 (m, 1H), 7.78-7.70 (m, 2H), 7.09-7.01 (m, 1H), 6.78-6.57 (m, 1H), 5.45 (s, 1H), 4.87-3.85 (m, 4H), 3.85-3.76 (m, 4H), 3.63-3.48 (m, 2H), 3.27-3.10 (m, 6H), 2.93-2.79 (m, 1H), 2.24-1.85 (m, 2H).

Example 50

6-[(1S,6R)-8-{[5-Methoxy-2-(2H-1,2,3-triazol-2-yl)phenyl]carbonyl}-3,8-diazabicyclo[4.2.0]oct-3-yl]-2-methylpyrimidin-4-amine

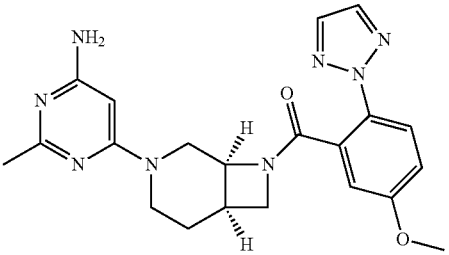

The title compound was prepared in a manner analogous to Example 43 substituting 6-chloro-2-methylpyrimidin-4- amine for 2-chloro-4,6-dimethylpyrimidine. MS (ESI) mass calcd. for $C_{21}H_{24}N_8O_2$, 420.5; m/z found, 421.2 [M+H]$^+$.

Example 51

(1S,6R)-3-(4,6-Dimethylpyrimidin-2-yl)-8-{[4-methoxy-2-(2H-1,2,3-triazol-2-yl)phenyl]carbonyl}-3,8-diazabicyclo[4.2.0]octane

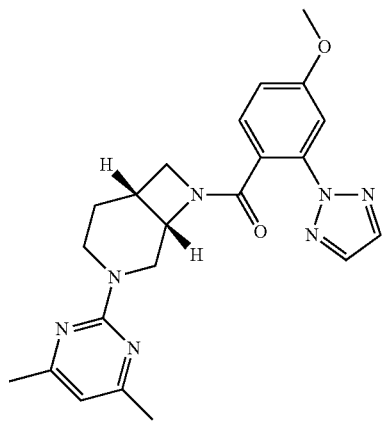 [SMILES: COc1ccc(C(=O)N2C[C@H]3CCN(c4nc(C)cc(C)n4)C[C@H]32)c(-n2nccn2)c1]

The title compound was prepared in a manner analogous to Example 35 substituting Intermediate 26 for Intermediate 25 and 2-chloro-4,6-dimethylpyrimidine for 2-chloro-4,5,6-trimethylpyrimdine. MS (ESI) mass calcd. for $C_{22}H_{25}N_7O_2$, 419.5; m/z found, 420.2 [M+H]$^+$.

Example 52

(1S,6R)-3-(4,6-Dimethylpyrimidin-2-yl)-8-{[3-methyl-2-(1H-1,2,3-triazol-1-yl)phenyl]carbonyl}-3,8-diazabicyclo[4.2.0]octane

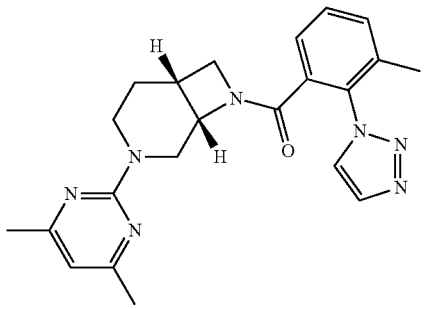

The title compound was prepared in a manner analogous to Example 32, substituting 3-methyl-2-(1H-1,2,3-triazol-1-yl) benzoic acid for 2-(3-methyl-1,2,4-oxadiazol-5-yl)benzoic acid. MS (ESI) mass calcd. for $C_{22}H_{25}N_7O$, 403.5; m/z found, 404.2 [M+H]$^+$. $^1$H NMR (500 MHz, MeOD): 8.10-8.01 (m, 1H), 7.97-7.75 (m, 1H), 7.64-7.60 (m, 1H), 7.58-7.49 (m, 2H), 6.91-6.64 (m, 1H), 4.24-4.05 (m, 2H), 3.93-3.75 (m, 3H), 3.59-3.32 (m, 1H), 3.04-2.95 (m, 1H), 2.76-2.37 (m, 4H), 2.37-2.19 (m, 3H), 2.10-1.91 (m, 5H).

Example 53

(1S,6R)-8-{[5-Methoxy-2-(2H-1,2,3-triazol-2-yl)phenyl]carbonyl}-3-[6-methyl-2-(1-methylethyl)pyrimidin-4-yl]-3,8-diazabicyclo[4.2.0]octane

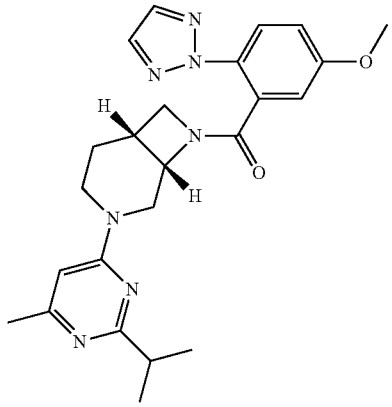

The title compound was prepared in a manner analogous to Example 43 substituting 6-chloro-2-isopropyl-4-methylpyrimidine for 2-chloro-4,6-dimethylpyrimidine. MS (ESI) mass calcd. for $C_{24}H_{29}N_7O_2$, 447.5; m/z found, 448.2 [M+H]$^+$.

Example 54

6-[(1S,6R)-8-{[5-Methoxy-2-(2H-1,2,3-triazol-2-yl)phenyl]carbonyl}-3,8-diazabicyclo[4.2.0]oct-3-yl]-N,N,2-trimethylpyrimidin-4-amine

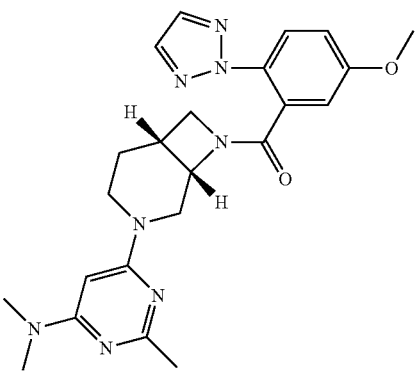

The title compound was prepared in a manner analogous to Example 43 substituting 6-chloro-N,N,2-trimethylpyrimidin-4-amine for 2-chloro-4,6-dimethylpyrimidine. MS (ESI) mass calcd. for $C_{23}H_{28}N_8O_2$, 448.5; m/z found, 449.2 [M+H]$^+$. $^1$H NMR (500 MHz, CDCl$_3$): 7.87-7.67 (m, 3H), 7.04-6.97 (m, 1H), 6.74-6.69 (m, 1H), 4.79-4.05 (m, 3H), 4.01-3.94 (m, 1H), 3.80-3.70 (m, 3H), 3.62-3.49 (m, 3H), 3.10-3.01 (m, 6H), 3.00-2.89 (m, Hz, 1H), 2.86-2.74 (m, 1H), 2.43-2.32 (m, 3H), 2.14-1.97 (m, 1H), 1.96-1.74 (m, 1H).

Example 55

4-[(1S,6R)-8-{[5-Methoxy-2-(2H-1,2,3-triazol-2-yl)phenyl]carbonyl}-3,8-diazabicyclo[4.2.0]oct-3-yl]-N,N,6-trimethylpyrimidin-2-amine

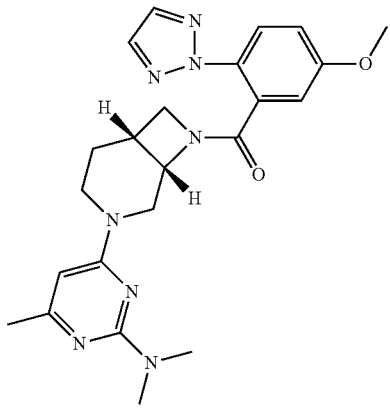

The title compound was prepared in a manner analogous to Example 43 substituting 4-chloro-N,N,6-trimethylpyrimidin-2-amine for 2-chloro-4,6-dimethylpyrimidine. MS (ESI) mass calcd. for $C_{23}H_{28}N_8O_2$, 448.5; m/z found, 449.2 [M+H]+. $^1$H NMR (500 MHz, CDCl$_3$): 7.88-7.64 (m, 3H), 7.04-6.95 (m, 1H), 6.74-6.61 (m, 1H), 5.76-5.38 (m, 1H), 4.77-3.94 (m, 3H), 3.81-3.58 (m, 3H), 3.58-3.46 (m, 3H), 3.18-3.10 (m, 3H), 3.09-2.98 (m, 4H), 2.88-2.68 (m, 1H), 2.29-2.18 (m, 3H), 2.12-1.98 (m, 1H), 1.97-1.74 (m, 1H).

Example 56

(1S,6R)-3-(4,6-Dimethylpyrimidin-2-yl)-8-{[3-fluoro-2-(1H-pyrazol-1-yl)phenyl]carbonyl}-3,8-diazabicyclo[4.2.0]octane

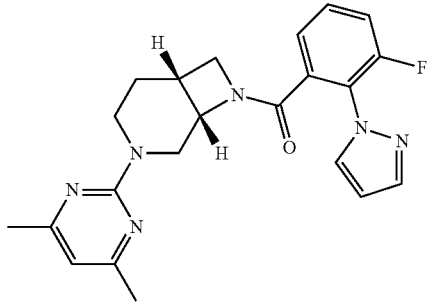 [SMILES: Cc1cc(C)nc(N2CC[C@@H]3CN(C(=O)c4cccc(F)c4-n4cccn4)[C@@H]3C2)n1]

The title compound was prepared in a manner analogous to Example 32 substituting 3-fluoro-2-(1H-pyrazol-1-yl)benzoic acid for 2-(3-methyl-1,2,4-oxadiazol-5-yl)benzoic acid. MS (ESI) mass calcd. for $C_{22}H_{23}FN_6O$, 406.5; m/z found, 407.2 [M+H]+.

Example 57

(1S,6R)-8-{[4-Methoxy-2-(2H-1,2,3-triazol-2-yl)phenyl]carbonyl}-3-(4,5,6-trimethylpyrimidin-2-yl)-3,8-diazabicyclo[4.2.0]octane

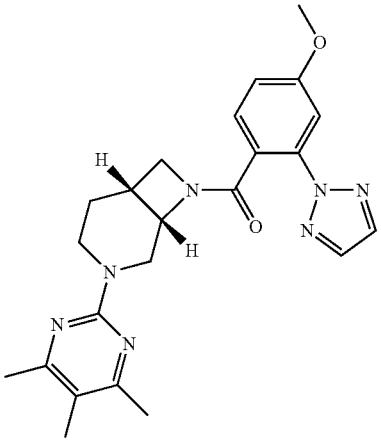 [SMILES: COc1ccc(C(=O)N2C[C@H]3CCN(c4nc(C)c(C)c(C)n4)C[C@H]32)c(-n2nccn2)c1]

The title compound was prepared in a manner analogous to Example 52 substituting 2-chloro-4,5,6-trimethylpyrimidine for 2-chloro-4,6-dimethylpyrimidine. MS (ESI) mass calcd. for $C_{23}H_{27}N_7O_2$, 433.5; m/z found, 434.2 [M+H]+. $^1$H NMR (500 MHz, CDCl$_3$): 7.83-7.72 (m, 1H), 7.53-7.42 (m, 1H), 7.30-7.17 (m, 1H), 6.96-6.84 (m, 1H), 4.87-4.72 (m, 1H), 4.44-3.95 (m, 4H), 3.95-3.81 (m, 5H), 3.59-3.20 (m, 1H), 2.99-2.77 (m, 1H), 2.67-2.32 (m, 6H), 2.21-2.09 (m, 4H), 2.09-1.92 (m, 1H).

Example 58

(1S,6R)-8-{[4-Methoxy-2-(2H-1,2,3-triazol-2-yl)phenyl]carbonyl}-3-[4-(trifluoromethyl)pyrimidin-2-yl]-3,8-diazabicyclo[4.2.0]octane

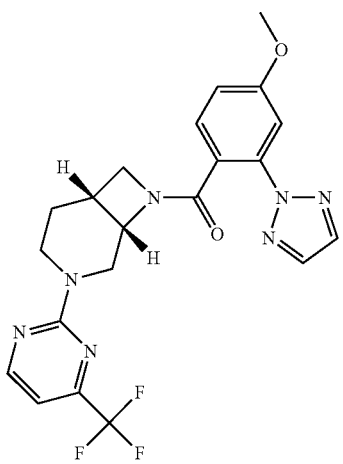 [SMILES: COc1ccc(C(=O)N2C[C@H]3CCN(c4nccc(C(F)(F)F)n4)C[C@H]32)c(-n2nccn2)c1]

The title compound was prepared in a manner analogous to Example 52 substituting 2-chloro-4-trifluoromethylpyrimidine for 2-chloro-4,6-dimethylpyrimidine. MS (ESI) mass calcd. for $C_{21}H_{20}F_3N_7O_2$, 459.4; m/z found, 460.2 [M+H]+.

Example 59

(1S,6R)-8-{[4-Methoxy-2-(2H-1,2,3-triazol-2-yl)phenyl]carbonyl}-3-[4-(trifluoromethyl)pyridin-2-yl]-3,8-diazabicyclo[4.2.0]octane

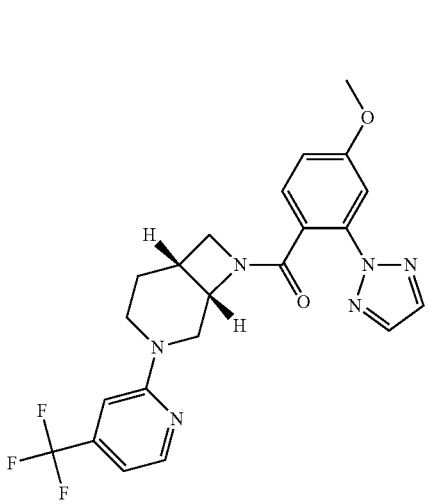 [SMILES: COc1ccc(C(=O)N2C[C@H]3CCN(c4cc(C(F)(F)F)ccn4)C[C@H]32)c(-n2nccn2)c1]

The title compound was prepared in a manner analogous to Example 52 substituting 2-chloro-4-trifluoromethylpyridine for 2-chloro-4,6-dimethylpyrimidine. MS (ESI) mass calcd. for $C_{22}H_{21}F_3N_6O_2$, 458.5; m/z found, 459.2 [M+H]$^+$.

Example 60

6-[(1S,6R)-8-{[4-Methoxy-2-(2H-1,2,3-triazol-2-yl)phenyl]carbonyl}-3,8-diazabicyclo[4.2.0]oct-3-yl]-N,N-dimethylpyrimidin-4-amine

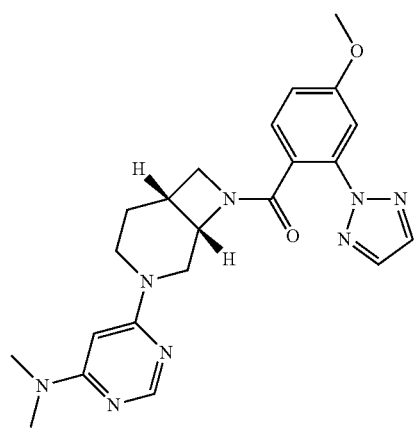 [SMILES: COc1ccc(C(=O)N2C[C@H]3CCN(c4cc(N(C)C)ncn4)C[C@H]32)c(-n2nccn2)c1]

The title compound was prepared in a manner analogous to Example 52 substituting 6-chloro-N,N-dimethylpyrimidin-4-amine for 2-chloro-4,6-dimethylpyrimidine. MS (ESI) mass calcd. for $C_{22}H_{26}N_8O_2$, 434.5; m/z found, 435.2 [M+H]$^+$. $^1$H NMR (500 MHz, CDCl$_3$): 8.32-8.15 (m, 1H), 7.8-7.7 (m, 2H), 7.53-7.37 (m, 1H), 7.23-7.05 (m, 1H), 6.93-6.80 (m, 1H), 5.25-4.73 (m, 1H), 4.39-3.92 (m, 2H), 3.91-3.86 (m, 3H), 3.85-3.64 (m, 2H), 3.57-3.42 (m, 1H), 3.15-3.04 (m, 6H), 2.88-2.75 (m, 1H), 2.20-1.92 (m, 2H), 1.90-1.73 (m, 2H).

Example 61

6-[(1S,6R)-8-{[4-Methoxy-2-(2H-1,2,3-triazol-2-yl)phenyl]carbonyl}-3,8-diazabicyclo[4.2.0]oct-3-yl]-N,N,2-trimethylpyrimidin-4-amine

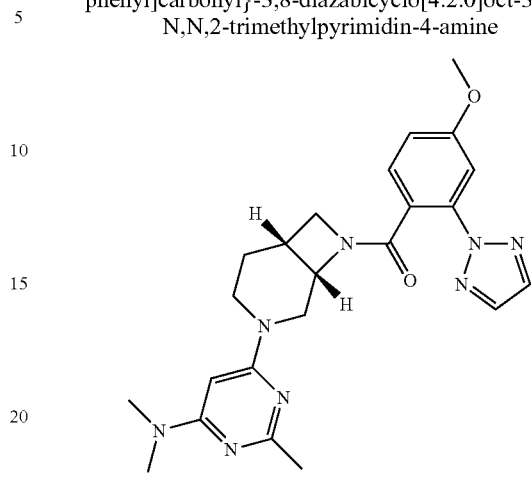

The title compound was prepared in a manner analogous to Example 52 substituting 6-chloro-N,N,2-trimethylpyrimidin-4-amine for 2-chloro-4,6-dimethylpyrimidine. MS (ESI) mass calcd. for $C_{23}H_{28}N_8O_2$, 448.5; m/z found, 449.2 [M+H]$^+$. $^1$H NMR (500 MHz, CDCl$_3$): 7.83-7.69 (m, 2H), 7.52-7.40 (m, 1H), 7.24-7.15 (m, 1H), 6.94-6.82 (m, 1H), 5.32-5.06 (m, 1H), 4.80-3.93 (m, 3H), 3.92-3.85 (m, 3H), 3.85-3.63 (m, 2H), 3.53-3.44 (m, 1H), 3.13-3.02 (m, 6H), 3.01-2.93 (m, 1H), 2.89-2.73 (m, 1H), 2.47-2.36 (m, 3H), 2.18-1.74 (m, 2H).

Example 62

4-[(1S,6R)-8-{[4-Methoxy-2-(2H-1,2,3-triazol-2-yl)phenyl]carbonyl}-3,8-diazabicyclo[4.2.0]oct-3-yl]-N,N,6-trimethylpyrimidin-2-amine

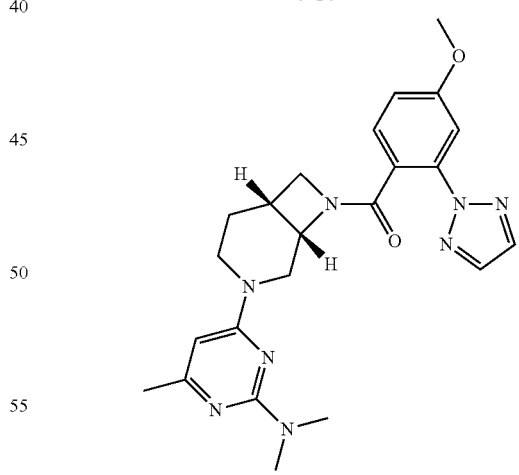

The title compound was prepared in a manner analogous to Example 52 substituting 4-chloro-N,N,6-trimethylpyrimidin-2-amine for 2-chloro-4,6-dimethylpyrimidine. MS (ESI) mass calcd. for $C_{23}H_{28}N_8O_2$, 448.5; m/z found, 449.2 [M+H]$^+$. $^1$H NMR (500 MHz, CDCl$_3$): 7.83-7.65 (m, 2H), 7.52-7.38 (m, 1H), 7.23-7.04 (m, 1H), 6.93-6.75 (m, 1H), 5.70-5.49 (m, 1H), 4.79-3.92 (m, 3H), 3.91-3.85 (m, 3H), 3.78-3.42 (m, 3H), 3.19-3.01 (m, 6H), 2.85-2.71 (m, 1H), 2.30-2.22 (m, 3H), 2.16-1.71 (m, 3H).

Example 63

(1S,6R)-8-{[4-Methoxy-2-(2H-1,2,3-triazol-2-yl)phenyl]carbonyl}-3-[6-methyl-2-(1-methylethyl)pyrimidin-4-yl]-3,8-diazabicyclo[4.2.0]octane

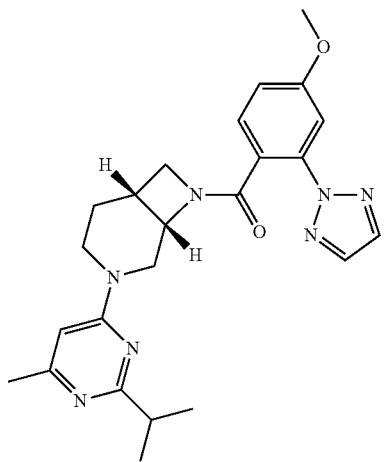 [SMILES: COc1ccc(C(=O)N2C[C@H]3CCN(c4cc(C)nc(C(C)C)n4)C[C@H]32)c(-n2nccn2)c1]

The title compound was prepared in a manner analogous to Example 52 substituting 4-chloro-2-isopropyl-6-methylpyrimidine for 2-chloro-4,6-dimethylpyrimidine. MS (ESI) mass calcd. for $C_{24}H_{29}N_7O_2$, 447.5; m/z found, 448.2 [M+H]$^+$. $^1$H NMR (500 MHz, CDCl$_3$): 7.80-7.59 (m, 2H), 7.54-7.38 (m, 1H), 7.21-7.13 (m, 1H), 6.93-6.82 (m, 1H), 6.23-5.87 (m, 1H), 4.82-3.94 (m, 3H), 3.93-3.84 (m, 3H), 3.81-3.40 (m, 3H), 3.23-2.75 (m, 3H), 2.40-2.32 (m, 3H), 2.18-1.76 (m, 2H), 1.39-1.18 (m, 6H).

Example 64

((1S,6R)-3-(4-amino-6-methylpyrimidin-2-yl)-3,8-diazabicyclo[4.2.0]octan-8-yl)(4-methoxy-2-(2H-1,2,3-triazol-2-yl)phenyl)methanone

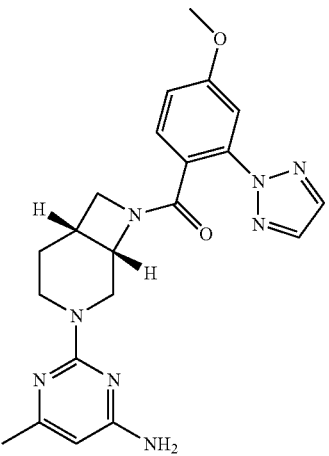 [SMILES: COc1ccc(C(=O)N2C[C@H]3CCN(c4nc(C)cc(N)n4)C[C@H]32)c(-n2nccn2)c1]

The title compound was prepared in a manner analogous to Example 52 substituting 2-chloro-6-methylpyrimidin-4-amine for 2-chloro-4,6-dimethylpyrimidine. MS (ESI) mass calcd. for $C_{21}H_{24}N_8O_2$, 420.2; m/z found, 421.1 [M+H]$^+$.

Example 65

(1R,6S)-3-(4,6-Dimethylpyrimidin-2-yl)-8-{[2-fluoro-6-(2H-1,2,3-triazol-2-yl)phenyl]carbonyl}-3,8-diazabicyclo[4.2.0]octane

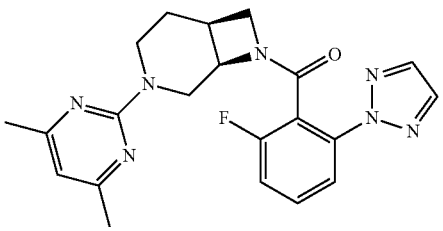 [SMILES: Cc1cc(C)nc(N2CC[C@H]3CN(C(=O)c4c(F)cccc4-n4nccn4)[C@H]3C2)n1]

(1R,6S)-3,8-Diazabicyclo[4.2.0]octan-8-yl(2-fluoro-6-(2H-1,2,3-triazol-2-yl)phenyl)methanone (Intermediate 29, 56 mg, 0.19 mmol), 2-chloro-4,6-dimethylpyrimidine (32 mg, 0.22 mmol) and DIPEA (96 μL, 0.56 mmol) in ACN (2 mL) were heated in a microwave reactor for 1 h at 150° C. Then the reaction mixture was diluted with water and extracted with DCM (2×). The combined organics were dried (Na$_2$SO$_4$) and concentrated. Purification via prep HPLC (Agilent, basic) gave 40 mg (53%) of the title compound as a clear oil. MS (ESI) mass calcd. For $C_{21}H_{22}FN_7O$, 407.45; m/z found 408.0 [M+H]$^+$. $^1$H NMR (CDCl$_3$): 8.00-6.88 (m, 5H), 6.38-5.88 (m, 1H), 4.95-3.57 (m, 6H), 3.29-2.61 (m, 2H), 2.47-1.80 (m, 8H).

Example 66

(1S,6R)-3-(4,6-Dimethylpyrimidin-2-yl)-8-{[2-fluoro-6-(2H-1,2,3-triazol-2-yl)phenyl]carbonyl}-3,8-diazabicyclo[4.2.0]octane

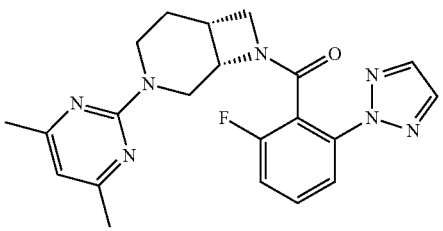 [SMILES: Cc1cc(C)nc(N2CC[C@@H]3CN(C(=O)c4c(F)cccc4-n4nccn4)[C@@H]3C2)n1]

The title compound was prepared in a manner analogous to Example 65, substituting (1S,6R)-3,8-Diazabicyclo[4.2.0]octan-8-yl(2-fluoro-6-(2H-1,2,3-triazol-2-yl)phenyl)methanone (Intermediate 28) for (1R,6S)-3,8-Diazabicyclo[4.2.0]octan-8-yl(2-fluoro-6-(2H-1,2,3-triazol-2-yl)phenyl)methanone (Intermediate 29). MS (ESI) mass calcd. For $C_{21}H_{22}FN_7O$, 407.45; m/z found 408.0 [M+H]$^+$. $^1$H NMR (CDCl$_3$): 8.00-6.88 (m, 5H), 6.38-5.88 (m, 1H), 4.95-3.57 (m, 6H), 3.29-2.61 (m, 2H), 2.47-1.80 (m, 8H).

Example 67

(1R,6S)-8-{[2-Fluoro-6-(2H-1,2,3-triazol-2-yl)phenyl]carbonyl}-3-[4-(trifluoromethyl)pyrimidin-2-yl]-3,8-diazabicyclo[4.2.0]octane

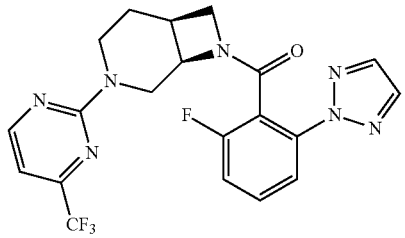 [SMILES: O=C(c1c(F)cccc1-n1nccn1)N1C[C@@H]2CCN(c3nccc(C(F)(F)F)n3)C[C@@H]21]

The title compound was prepared in a manner analogous to Example 65, substituting 2-chloro-4-(trifluoromethyl)pyrimidine for 2-chloro-4,6-dimethylpyrimidine. MS (ESI) mass calcd. For $C_{20}H_{17}F_4N_7O$, 447.40; m/z found 448.0 [M+H]$^+$. $^1$H NMR (CDCl$_3$): 8.63-8.28 (m, 1H), 8.11-6.43 (m, 6H), 5.07-3.57 (m, 6H), 3.31-2.73 (m, 2H), 2.29-1.81 (m, 2H).

Example 68

(1S,6R)-8-{[2-Fluoro-6-(2H-1,2,3-triazol-2-yl)phenyl]carbonyl}-3-[4-(trifluoromethyl)pyrimidin-2-yl]-3,8-diazabicyclo[4.2.0]octane

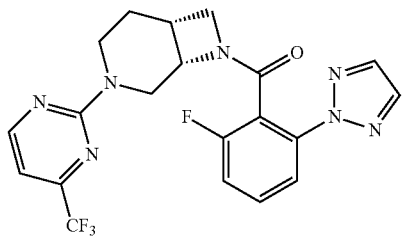 [SMILES: O=C(c1c(F)cccc1-n1nccn1)N1C[C@H]2CCN(c3nccc(C(F)(F)F)n3)C[C@H]21]

The title compound was prepared in a manner analogous to Example 66, substituting 2-chloro-4-(trifluoromethyl)pyrimidine for 2-chloro-4,6-dimethylpyrimidine. MS (ESI) mass calcd. For $C_{20}H_{17}F_4N_7O$, 447.40; m/z found 448.0 [M+H]$^+$. $^1$H NMR (CDCl$_3$): 8.63-8.28 (m, 1H), 8.11-6.43 (m, 6H), 5.07-3.57 (m, 6H), 3.31-2.73 (m, 2H), 2.29-1.81 (m, 2H).

Example 69

(1S,6R)-3-(4,6-Dimethylpyridin-2-yl)-8-{[2-fluoro-6-(2H-1,2,3-triazol-2-yl)phenyl]carbonyl}-3,8-diazabicyclo[4.2.0]octane

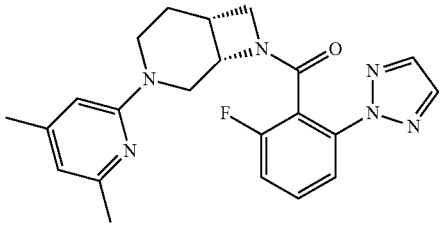 [SMILES: Cc1cc(C)nc(N2CC[C@@H]3CN(C(=O)c4c(F)cccc4-n4nccn4)[C@@H]3C2)c1]

The title compound was prepared in a manner analogous to Example 66, substituting 2-chloro-4,6-dimethylpyridine for 2-chloro-4,6-dimethylpyrimidine. MS (ESI) mass calcd. For $C_{22}H_{23}FN_6O$, 406.47; m/z found 407.0 [M+H]$^+$. $^1$H NMR (CDCl$_3$):

Example 70

(1S,6R)-8-{[2-Fluoro-6-(2H-1,2,3-triazol-2-yl)phenyl]carbonyl}-3-(4,5,6-trimethylpyrimidin-2-yl)-3,8-diazabicyclo[4.2.0]octane

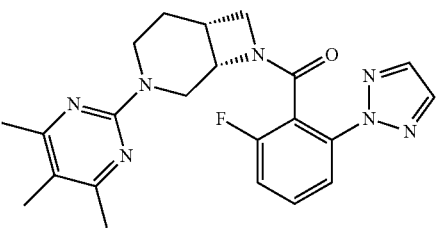 [SMILES: Cc1nc(N2CC[C@@H]3CN(C(=O)c4c(F)cccc4-n4nccn4)[C@@H]3C2)nc(C)c1C]

The title compound was prepared in a manner analogous to Example 66, substituting 2-chloro-4,5,6-trimethylpyrimidine (Intermediate 17) for 2-chloro-4,6-dimethylpyrimidine. MS (ESI) mass calcd. For $C_{22}H_{24}FN_7O$, 421.48; m/z found 422.0 [M+H]$^+$. $^1$H NMR (CDCl$_3$):

Example 71

4-[(1S,6R)-8-{[2-Fluoro-6-(2H-1,2,3-triazol-2-yl)phenyl]carbonyl}-3,8-diazabicyclo[4.2.0]oct-3-yl]quinoline

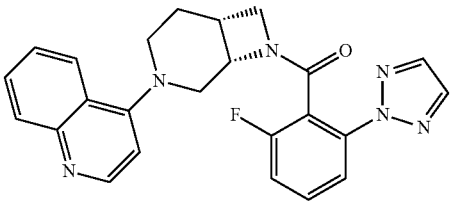 [SMILES: O=C(c1c(F)cccc1-n1nccn1)N1C[C@H]2CCN(c3ccnc4ccccc34)C[C@H]21]

The title compound was prepared in a manner analogous to Example 66, substituting 4-chloroquinoline for 2-chloro-4,6-dimethylpyrimidine. MS (ESI) mass calcd. For $C_{24}H_{21}FN_6O$, 428.47; m/z found 429.0 [M+H]$^+$. $^1$H NMR (CDCl$_3$): 8.76-8.56 (m, 1H), 8.22-8.00 (m, 2H), 7.93-7.25 (m, 6H), 7.22-6.49 (m, 2H), 4.94-2.68 (m, 6H), 2.36-1.66 (m, 4H).

Example 72

4-[(1S,6R)-8-{[2-Fluoro-6-(2H-1,2,3-triazol-2-yl)phenyl]carbonyl}-3,8-diazabicyclo[4.2.0]oct-3-yl]-2-methylquinoline

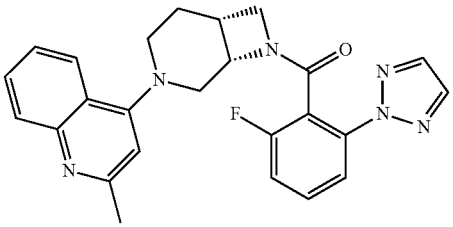 [SMILES: Cc1cc(N2CC[C@@H]3CN(C(=O)c4c(F)cccc4-n4nccn4)[C@@H]3C2)c2ccccc2n1]

The title compound was prepared in a manner analogous to Example 66, substituting 4-chloro-2-methylquinoline for 2-chloro-4,6-dimethylpyrimidine. MS (ESI) mass calcd. For $C_{25}H_{23}FN_6O$, 442.50; m/z found 443.0 [M+H]$^+$. $^1$H NMR (CDCl$_3$):

Example 73

(1S,6R)-3-(4,6-Dimethylpyrimidin-2-yl)-8-{[5-fluoro-2-(2H-1,2,3-triazol-2-yl)phenyl]carbonyl}-3,8-diazabicyclo[4.2.0]octane

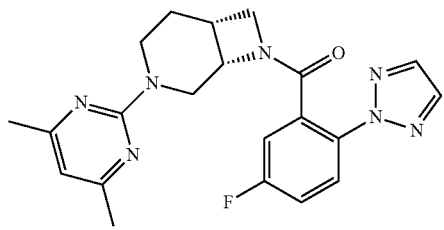 [SMILES: Cc1cc(C)nc(N2CC[C@@H]3CN(C(=O)c4cc(F)ccc4-n4nccn4)[C@@H]3C2)n1]

The title compound was prepared in a manner analogous to Example 65, substituting (1S,6R)-3,8-diazabicyclo[4.2.0]octan-8-yl(5-fluoro-2-(2H-1,2,3-triazol-2-yl)phenyl)methanone (Intermediate 30) for (1R,6S)-3,8-diazabicyclo[4.2.0]octan-8-yl(2-fluoro-6-(2H-1,2,3-triazol-2-yl)phenyl)methanone (Intermediate 28). MS (ESI) mass calcd. For $C_{21}H_{22}FN_7O$, 407.45; m/z found 408.0 [M+H]$^+$. $^1$H NMR (CDCl$_3$): 8.01-7.83 (m, 1H), 7.83-7.65 (m, 2H), 7.31-6.94 (m, 2H), 6.36-6.27 (m, 1H), 4.85-4.44 (m, 1H), 4.35-3.95 (m, 3H), 3.91-3.49 (m, 2H), 3.13-2.76 (m, 2H), 2.39-2.27 (m, 7H), 2.13-1.78 (m, 2H).

Example 74

(1S,6R)-3-(3,6-Dimethylpyrazin-2-yl)-8-{[5-fluoro-2-(2H-1,2,3-triazol-2-yl)phenyl]carbonyl}-3,8-diazabicyclo[4.2.0]octane

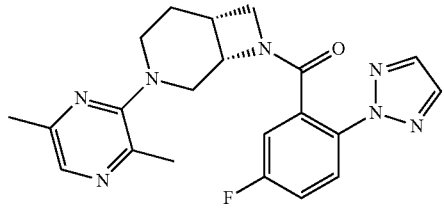 [SMILES: Cc1cnc(C)c(N2CC[C@@H]3CN(C(=O)c4cc(F)ccc4-n4nccn4)[C@@H]3C2)n1]

The title compound was prepared in a manner analogous to Example 73, substituting 3-chloro-2,5-dimethylpyrazine for 2-chloro-4,6-dimethylpyrimidine. MS (ESI) mass calcd. For $C_{21}H_{22}FN_7O$, 407.45; m/z found 408.0 [M+H]$^+$. $^1$H NMR (CDCl$_3$): 7.98-7.74 (m, 3H), 7.27-6.78 (m, 3H), 4.81-3.72 (m, 4H), 3.67-3.51 (m, 1H), 3.30-2.98 (m, 2H), 2.87-2.69 (m, 1H), 2.59-2.26 (m, 6H), 2.17-1.83 (m, 2H).

Example 75

(1S,6R)-8-{[5-Fluoro-2-(2H-1,2,3-triazol-2-yl)phenyl]carbonyl}-3-(4-methylpyrimidin-2-yl)-3,8-diazabicyclo[4.2.0]octane

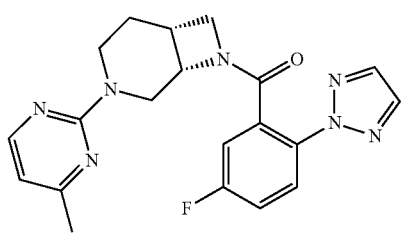 [SMILES: Cc1ccnc(N2CC[C@@H]3CN(C(=O)c4cc(F)ccc4-n4nccn4)[C@@H]3C2)n1]

The title compound was prepared in a manner analogous to Example 73, substituting 2-chloro-4-methylpyrimidine for 2-chloro-4,6-dimethylpyrimidine. MS (ESI) mass calcd. For $C_{20}H_{20}FN_7O$, 393.43; m/z found 394.0 [M+H]$^+$. $^1$H NMR (CDCl$_3$): 8.27-8.16 (m, 1H), 8.00-7.83 (m, 1H), 7.83-7.64 (m, 2H), 7.27-6.94 (m, 2H), 6.46-6.38 (m, 1H), 4.87-3.51 (m, 6H), 3.14-2.78 (m, 2H), 2.42-2.30 (m, 3H), 2.17-1.77 (m, 2H).

Example 76

(1S,6R)-3-(4,5-Dimethylpyrimidin-2-yl)-8-{[5-fluoro-2-(2H-1,2,3-triazol-2-yl)phenyl]carbonyl}-3,8-diazabicyclo[4.2.0]octane

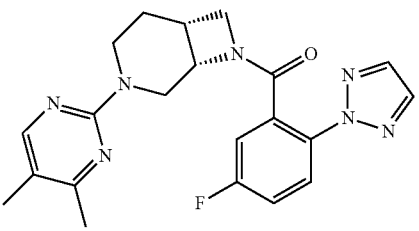 [SMILES: Cc1cnc(N2CC[C@@H]3CN(C(=O)c4cc(F)ccc4-n4nccn4)[C@@H]3C2)nc1C]

The title compound was prepared in a manner analogous to Example 73, substituting 2-chloro-4,5-dimethylpyrimidine (Intermediate 33) for 2-chloro-4,6-dimethylpyrimidine. MS (ESI) mass calcd. For $C_{21}H_{22}FN_7O$, 407.45; m/z found 408.1 [M+H]$^+$. $^1$H NMR (CDCl$_3$): 8.13-7.66 (m, 4H), 7.26-6.91 (m, 2H), 4.82-4.37 (m, 1H), 4.31-3.93 (m, 3H), 3.83-3.51 (m, 2H), 3.15-2.75 (m, 2H), 2.36-2.31 (m, 3H), 2.16-2.03 (m, 4H), 2.00-1.78 (m, 1H).

Example 77

(1S,6R)-8-{[5-Fluoro-2-(2H-1,2,3-triazol-2-yl)phenyl]carbonyl}-3-(4,5,6-trimethylpyrimidin-2-yl)-3,8-diazabicyclo[4.2.0]octane

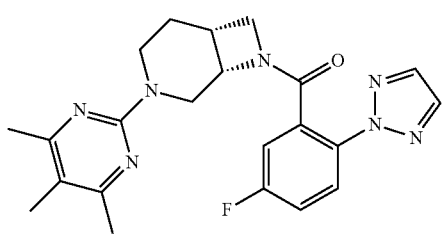 [SMILES: Cc1nc(N2CC[C@@H]3CN(C(=O)c4cc(F)ccc4-n4nccn4)[C@@H]3C2)nc(C)c1C]

The title compound was prepared in a manner analogous to Example 73, substituting 2-chloro-4,5,6-trimethylpyrimidine (Intermediate 17) for 2-chloro-4,6-dimethylpyrimidine. MS (ESI) mass calcd. For $C_{22}H_{24}FN_7O$, 421.48; m/z found 422.0 [M+H]$^+$. $^1$H NMR (CDCl$_3$): 7.98-7.84 (m, 1H), 7.83-7.69 (m, 2H), 7.25-7.15 (m, 1H), 7.15-6.90 (m, 1H), 4.85-3.50 (m, 6H), 3.16-2.76 (m, 2H), 2.40-2.30 (m, 5H), 2.16-1.88 (m, 5H), 1.87-1.34 (m, 1H).

Example 78

(1S,6R)-8-{[5-Fluoro-2-(2H-1,2,3-triazol-2-yl)phenyl]carbonyl}-3-[4-(trifluoromethyl)pyrimidin-2-yl]-3,8-diazabicyclo[4.2.0]octane

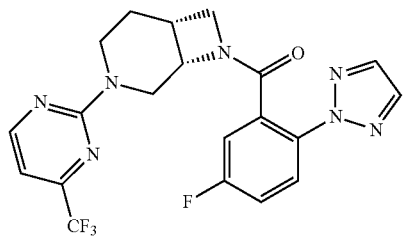 [SMILES: O=C(c1cc(F)ccc1-n1nccn1)N1C[C@H]2CCN(c3nccc(C(F)(F)F)n3)C[C@H]21]

The title compound was prepared in a manner analogous to Example 73, substituting 2-chloro-4-(trifluoromethyl)pyrimidine for 2-chloro-4,6-dimethylpyrimidine. MS (ESI) mass calcd. For $C_{20}H_{17}F_4N_7O$, 447.40; m/z found 448.0 $[M+H]^+$. $^1$H NMR (CDCl$_3$): 8.64-8.37 (m, 1H), 8.08-7.57 (m, 3H), 7.28-6.72 (m, 3H), 5.00-3.41 (m, 6H), 3.24-2.77 (m, 2H), 2.21-1.74 (m, 2H).

Example 79

(1S,6R)-8-{[5-Fluoro-2-(2H-1,2,3-triazol-2-yl)phenyl]carbonyl}-3-[6-(trifluoromethyl)pyrimidin-4-yl]-3,8-diazabicyclo[4.2.0]octane

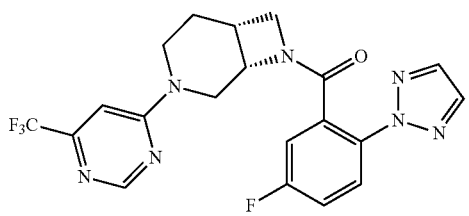 [SMILES: O=C(c1cc(F)ccc1-n1nccn1)N1C[C@H]2CCN(c3cc(C(F)(F)F)ncn3)C[C@H]21]

The title compound was prepared in a manner analogous to Example 73, substituting 4-chloro-6-(trifluoromethyl)pyrimidine for 2-chloro-4,6-dimethylpyrimidine. MS (ESI) mass calcd. For $C_{20}H_{17}F_4N_7O$, 447.40; m/z found 448.0 $[M+H]^+$. $^1$H NMR (CDCl$_3$): 8.84-8.55 (m, 1H), 8.08-7.60 (m, 3H), 7.28-6.58 (m, 3H), 4.95-3.35 (m, 6H), 3.19-2.77 (m, 2H), 2.33-1.82 (m, 2H).

Example 80

(1S,6R)-8-{[5-Fluoro-2-(2H-1,2,3-triazol-2-yl)phenyl]carbonyl}-3-[6-(trifluoromethyl)pyridin-2-yl]-3,8-diazabicyclo[4.2.0]octane

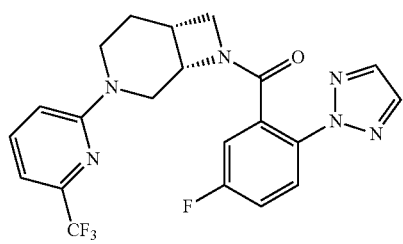 [SMILES: O=C(c1cc(F)ccc1-n1nccn1)N1C[C@H]2CCN(c3cccc(C(F)(F)F)n3)C[C@H]21]

The title compound was prepared in a manner analogous to Example 73, substituting 2-chloro-6-(trifluoromethyl)pyridine for 2-chloro-4,6-dimethylpyrimidine. MS (ESI) mass calcd. For $C_{21}H_{18}F_4N_6O$, 446.41; m/z found 447.0 $[M+H]^+$. $^1$H NMR (CDCl$_3$): 7.99-7.80 (m, 1H), 7.80-7.54 (m, 3H), 7.24-7.15 (m, 1H), 6.99-6.85 (m, 1H), 6.79-6.50 (m, 1H), 4.86-4.18 (m, 2H), 4.14-3.96 (m, 2H), 3.90-3.67 (m, 2H), 3.63-3.06 (m, 2H), 2.96-2.80 (m, 1H), 2.25-1.78 (m, 2H).

Example 81

(1S,6R)-8-{[5-Fluoro-2-(2H-1,2,3-triazol-2-yl)phenyl]carbonyl}-3-[4-(trifluoromethyl)pyridin-2-yl]-3,8-diazabicyclo[4.2.0]octane

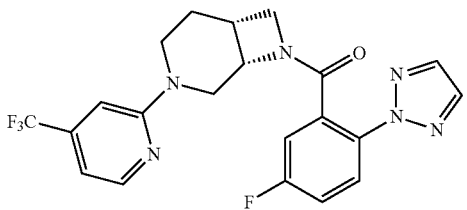 [SMILES: O=C(c1cc(F)ccc1-n1nccn1)N1C[C@H]2CCN(c3cc(C(F)(F)F)ccn3)C[C@H]21]

The title compound was prepared in a manner analogous to Example 73, substituting 2-chloro-4-(trifluoromethyl)pyridine for 2-chloro-4,6-dimethylpyrimidine. MS (ESI) mass calcd. For $C_{21}H_{18}F_4N_6O$, 446.41; m/z found 447.0 $[M+H]^+$. $^1$H NMR (CDCl$_3$): 8.42-8.22 (m, 1H), 8.01-7.84 (m, 1H), 7.82-7.54 (m, 2H), 7.26-7.16 (m, 1H), 7.01-6.85 (m, 1H), 6.82-6.50 (m, 2H), 4.88-4.47 (m, 1H), 4.36-4.18 (m, 2H), 4.06-3.02 (m, 4H), 2.97-2.81 (m, 1H), 2.29-1.84 (m, 2H).

Example 82

(1S,6R)-3-(4,6-Dimethylpyrimidin-2-yl)-8-{[3-fluoro-2-(2H-1,2,3-triazol-2-yl)phenyl]carbonyl}-3,8-diazabicyclo[4.2.0]octane

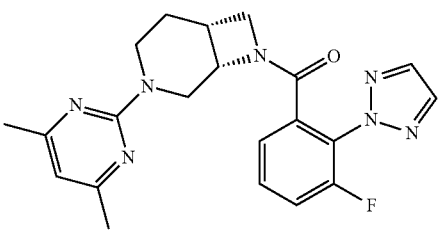 [SMILES: Cc1cc(C)nc(N2CC[C@@H]3CN(C(=O)c4cccc(F)c4-n4nccn4)[C@@H]3C2)n1]

The title compound was prepared in a manner analogous to Example 65, substituting (1S,6R)-3,8-diazabicyclo[4.2.0]octan-8-yl(3-fluoro-2-(2H-1,2,3-triazol-2-yl)phenyl)methanone (Intermediate 31) for (1R,6S)-3,8-diazabicyclo[4.2.0]octan-8-yl(2-fluoro-6-(2H-1,2,3-triazol-2-yl)phenyl)methanone (Intermediate 28). MS (ESI) mass calcd. For $C_{21}H_{22}FN_7O$, 407.45; m/z found 408.0 $[M+H]^+$. $^1$H NMR (CDCl$_3$): 7.94-7.62 (m, 2H), 7.48-7.12 (m, 3H), 6.30 (s, 1H), 4.74-4.43 (m, 2H), 4.09-3.63 (m, 4H), 3.23-2.74 (m, 2H), 2.31 (s, 6H), 2.17-1.75 (m, 2H).

Example 83

(1S,6R)-3-(5-Fluoro-4-methylpyrimidin-2-yl)-8-{[3-fluoro-2-(2H-1,2,3-triazol-2-yl)phenyl]carbonyl}-3,8-diazabicyclo[4.2.0]octane

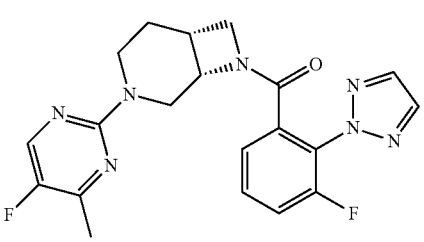 [SMILES: Cc1nc(N2CC[C@@H]3CN(C(=O)c4cccc(F)c4-n4nccn4)[C@@H]3C2)ncc1F]

The title compound was prepared in a manner analogous to Example 82, substituting 2-chloro-5-fluoro-4-methylpyrimidine (Intermediate 7) for 2-chloro-4,6-dimethylpyrimidine. MS (ESI) mass calcd. For $C_{20}H_{19}F_2N_7O$, 411.42; m/z found 412.0 $[M+H]^+$. $^1$H NMR (CDCl$_3$): 8.12-8.03 (m, 1H), 7.90-7.67 (m, 2H), 7.49-7.28 (m, 2H), 7.16 (dd, J=22.9, 7.6 Hz, 1H), 4.72-4.28 (m, 2H), 4.09-3.59 (m, 4H), 3.23-2.76 (m, 2H), 2.37 (dd, J=4.7, 2.5 Hz, 3H), 2.15-1.76 (m, 2H).

Example 84

(1S,6R)-8-{[3-Fluoro-2-(2H-1,2,3-triazol-2-yl)phenyl]carbonyl}-3-[6-(trifluoromethyl)pyrimidin-4-yl]-3,8-diazabicyclo[4.2.0]octane

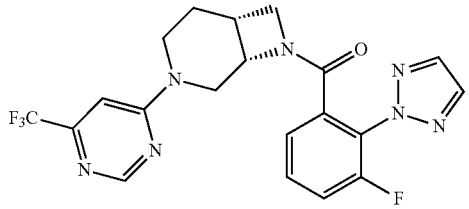 [SMILES: O=C(c1cccc(F)c1-n1nccn1)N1C[C@H]2CCN(c3cc(C(F)(F)F)ncn3)C[C@H]21]

The title compound was prepared in a manner analogous to Example 82, substituting 4-chloro-6-(trifluoromethyl)pyrimidine for 2-chloro-4,6-dimethylpyrimidine. MS (ESI) mass calcd. For $C_{20}H_{17}F_4N_7O$, 447.40; m/z found 447.9 $[M+H]^+$. $^1H$ NMR (CDCl$_3$): 8.88-8.49 (m, 1H), 7.94-7.58 (m, 2H), 7.55-6.58 (m, 4H), 4.89-2.79 (m, 8H), 2.34-1.80 (m, 2H).

Example 85

(1S,6R)-8-{[3-Fluoro-2-(2H-1,2,3-triazol-2-yl)phenyl]carbonyl}-3-[6-(trifluoromethyl)pyridin-2-yl]-3,8-diazabicyclo[4.2.0]octane

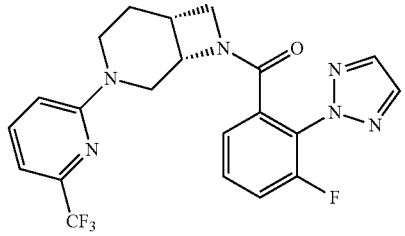 [SMILES: O=C(c1cccc(F)c1-n1nccn1)N1C[C@H]2CCN(c3cccc(C(F)(F)F)n3)C[C@H]21]

The title compound was prepared in a manner analogous to Example 82, substituting 2-chloro-6-(trifluoromethyl)pyridine for 2-chloro-4,6-dimethylpyrimidine. MS (ESI) mass calcd. For $C_{21}H_{18}F_4N_6O$, 446.41; m/z found 446.9 $[M+H]^+$. $^1H$ NMR (CDCl$_3$): 7.91-7.52 (m, 3H), 7.49-7.27 (m, 2H), 7.20-7.06 (m, 1H), 6.99-6.91 (m, 1H), 6.72-6.57 (m, 1H), 4.76-4.16 (m, 2H), 4.08-3.07 (m, 5H), 3.05-2.79 (m, 1H), 2.25-1.76 (m, 2H).

Example 86

(1S,6R)-8-{[3-Fluoro-2-(2H-1,2,3-triazol-2-yl)phenyl]carbonyl}-3-[4-(trifluoromethyl)pyridin-2-yl]-3,8-diazabicyclo[4.2.0]octane

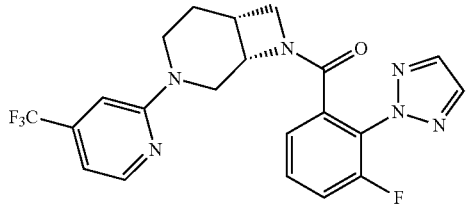

The title compound was prepared in a manner analogous to Example 82, substituting 2-chloro-4-(trifluoromethyl)pyridine for 2-chloro-4,6-dimethylpyrimidine. MS (ESI) mass calcd. For $C_{21}H_{18}F_4N_6O$, 446.41; m/z found 446.9 $[M+H]^+$. $^1H$ NMR (CDCl$_3$): 8.40-8.18 (m, 1H), 7.92-7.56 (m, 2H), 7.52-7.28 (m, 2H), 7.17-6.94 (m, 1H), 6.86-6.49 (m, 2H), 4.78-4.46 (m, 1H), 4.42-4.12 (m, 1H), 4.09-2.76 (m, 6H), 2.25-1.84 (m, 2H).

Example 87

(1S,6R)-3-(4,6-Dimethylpyrimidin-2-yl)-8-[(3-fluoro-2-pyrimidin-2-ylphenyl)carbonyl]-3,8-diazabicyclo[4.2.0]octane

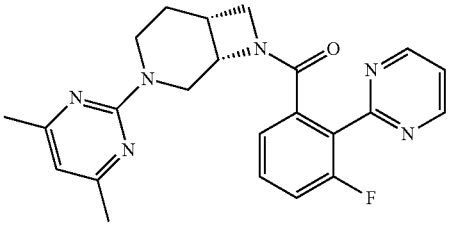 [SMILES: Cc1cc(C)nc(N2CC[C@@H]3CN(C(=O)c4cccc(F)c4-c4ncccn4)[C@@H]3C2)n1]

To a mixture of (1S,6R)-3-(4,6-dimethylpyrimidin-2-yl)-3,8-diazabicyclo[4.2.0]octane (Intermediate 34, 30 mg, 0.14 mmol), 3-fluoro-2-(pyrimidin-2-yl)benzoic acid (Intermediate 35, 30 mg, 0.14 mmol), and TEA (29 µL, 0.21 mmol) in DMF (1.3 mL) was added HATU (58 mg, 0.15 mmol) After 15 h, the reaction mixture was purified using prep HPLC (agilent, basic) to give 22.4 mg (39%) of the title compound as a clear oil. MS (ESI) mass calcd. For $C_{23}H_{23}FN_6O$, 418.48; m/z found 419.2 $[M+H]^+$. $^1H$ NMR (CDCl$_3$): 8.89-8.57 (m, 2H), 7.50-7.32 (m, 1H), 7.28-7.04 (m, 3H), 6.37-6.23 (m, 1H), 4.76-4.50 (m, 2H), 4.15-3.45 (m, 4H), 3.25-2.73 (m, 2H), 2.43-2.24 (m, 6H), 2.20-1.69 (m, 2H).

Example 88

(1S,6R)-3-(4,6-Dimethylpyrimidin-2-yl)-8-{[3-fluoro-2-(1H-pyrazol-5-yl)phenyl]carbonyl}-3,8-diazabicyclo[4.2.0]octane

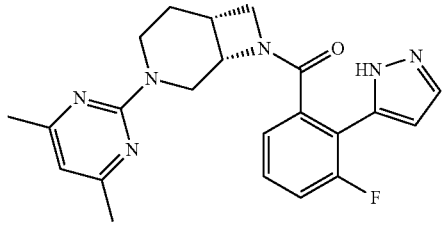 [SMILES: Cc1cc(C)nc(N2CC[C@@H]3CN(C(=O)c4cccc(F)c4-c4ccn[nH]4)[C@@H]3C2)n1]

The title compound was prepared in a manner analogous to Example 87, substituting 3-fluoro-2-(1H-pyrazol-5-yl)benzoic acid (Intermediate 36) for 3-fluoro-2-(pyrimidin-2-yl)benzoic acid (Intermediate 35). MS (ESI) mass calcd. For $C_{22}H_{23}FN_6O$, 406.47; m/z found 407.2 $[M+H]^+$. $^1H$ NMR (CDCl$_3$): 7.66-7.48 (m, 1H), 7.33-6.96 (m, 4H), 6.70-6.54 (m, 1H), 6.38-6.26 (m, 1H), 5.07-4.59 (m, 1H), 4.25-4.03 (m, 2H), 4.01-2.97 (m, 4H), 2.79-2.61 (m, 1H), 2.34-2.25 (m, 6H), 2.05-1.94 (m, 1H), 1.89-1.68 (m, 1H).

Example 89

(1S,6R)-3-(4,6-Dimethylpyrimidin-2-yl)-8-{[3-methyl-2-(1H-pyrazol-1-yl)phenyl]carbonyl}-3,8-diazabicyclo[4.2.0]octane

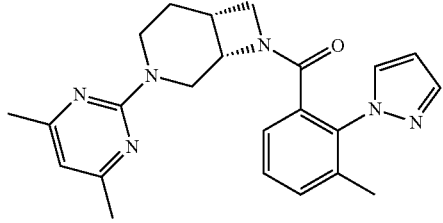 [SMILES: Cc1cc(C)nc(N2CC[C@@H]3CN(C(=O)c4cccc(C)c4-n4cccn4)[C@@H]3C2)n1]

The title compound was prepared in a manner analogous to Example 87, substituting 3-methyl-2-(1H-pyrazol-1-yl)benzoic acid (Intermediate 37) for 3-fluoro-2-(pyrimidin-2-yl)benzoic acid (Intermediate 35). MS (ESI) mass calcd. For $C_{23}H_{26}N_6O$, 402.50; m/z found 403.2 [M+H]$^+$. $^1$H NMR (CDCl$_3$): 7.74-7.51 (m, 2H), 7.39-7.09 (m, 3H), 6.45-6.12 (m, 2H), 4.58-4.26 (m, 2H), 4.07-2.98 (m, 5H), 2.80-2.64 (m, 1H), 2.33-2.28 (m, 6H), 2.19-2.11 (m, 3H), 2.06-1.71 (m, 2H).

Example 90

1S,6R)-3-(4,6-Dimethylpyrimidin-2-yl)-8-{[3-methoxy-2-(2H-1,2,3-triazol-2-yl)phenyl]carbonyl}-3,8-diazabicyclo[4.2.0]octane

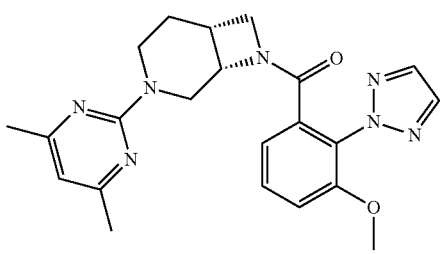 [SMILES: COc1cccc(C(=O)N2C[C@H]3CCN(c4nc(C)cc(C)n4)C[C@H]32)c1-n1nccn1]

The title compound was prepared in a manner analogous to Example 87, substituting 3-methoxy-2-(2H-1,2,3-triazol-2-yl)benzoic acid (Intermediate 39) for 3-fluoro-2-(pyrimidin-2-yl)benzoic acid (Intermediate 35). MS (ESI) mass calcd. For $C_{22}H_{25}N_7O_2$, 419.49; m/z found 420.2 [M+H]$^+$. $^1$H NMR (CDCl$_3$): 7.87-7.58 (m, 2H), 7.47-7.37 (m, 1H), 7.27-6.90 (m, 2H), 6.33-6.26 (m, 1H), 4.64-4.42 (m, 2H), 4.04-3.09 (m, 8H), 2.93-2.72 (m, 1H), 2.34-2.27 (m, 6H), 2.10-1.97 (m, 1H), 1.94-1.76 (m, 1H).

Example 91

(1S,6R)-3-(4,6-Dimethylpyrimidin-2-yl)-8-{[3-methoxy-2-(1H-1,2,3-triazol-1-yl)phenyl]carbonyl}-3,8-diazabicyclo[4.2.0]octane

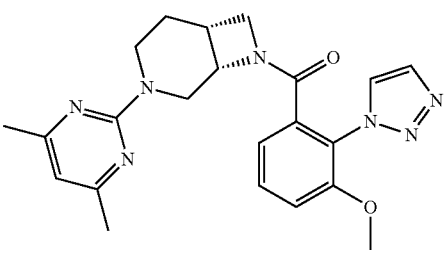 [SMILES: COc1cccc(C(=O)N2C[C@H]3CCN(c4nc(C)cc(C)n4)C[C@H]32)c1-n1ccnn1]

Step A: 3-methoxy-2-(1H-1,2,3-triazol-1-yl)benzoic acid and 3-fluoro-2-(1H-1,2,3-triazol-1-yl)benzoic acid. To 3-fluoro-2-(1H-1,2,3-triazol-1-yl)benzonitrile (2.1 g, 11.2 mmol) in MeOH (30 mL) was added 2M NaOH (aq, 10 mL). The reaction was heated at reflux until determined complete by HPLC then cooled to rt, acidified with 1N HCl to pH=1 and extracted with DCM (2×). The combined organics were washed with brine and dried (Na$_2$SO$_4$) resulting in a mixture of the title compounds that were used without further purification.

Step B: 2-(4,6-Dimethylpyrimidin-2-yl)-5-{[3-methoxy-2-(1H-1,2,3-triazol-1-yl)phenyl]carbonyl}octahydropyrrolo[3,4-c]pyrrole. Example 91 was prepared in a manner analogous to 87, utilizing a mixture of 3-methoxy-2-(1H-1,2,3-triazol-2-yl)benzoic acid and 3-fluoro-2-(1H-1,2,3-triazol-2-yl)benzoic acid obtained from Step A in place of 3-fluoro-2-(pyrimidin-2-yl)benzoic acid which gave 2 products, Example 91 and Example 92. For Example 91: MS (ESI) mass calcd. For $C_{22}H_{25}N_7O_2$, 419.49; m/z found 420.2 [M+H]$^+$. $^1$H NMR (CDCl$_3$): 7.92-7.70 (m, 2H), 7.47-7.39 (m, 1H), 7.26-6.81 (m, 2H), 6.33-6.24 (m, 1H), 4.80-4.46 (m, 2H), 4.20-3.12 (m, 8H), 3.05-2.73 (m, 1H), 2.35-2.23 (m, 6H), 2.14-2.00 (m, 1H), 1.97-1.84 (m, 1H).

Example 92

(1S,6R)-3-(4,6-Dimethylpyrimidin-2-yl)-8-{[3-fluoro-2-(1H-1,2,3-triazol-1-yl)phenyl]carbonyl}-3,8-diazabicyclo[4.2.0]octane

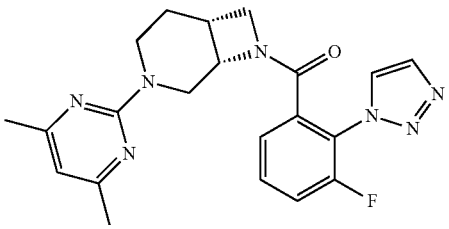 [SMILES: Cc1cc(C)nc(N2CC[C@@H]3CN(C(=O)c4cccc(F)c4-n4ccnn4)[C@@H]3C2)n1]

This compound was isolated from Step B in Example 91. MS (ESI) mass calcd. For $C_{21}H_{22}FN_7O$, 407.45; m/z found 408.2 [M+H]$^+$. $^1$H NMR (CDCl$_3$): 7.96-7.70 (m, 2H), 7.53-7.03 (m, 3H), 6.35-6.25 (m, 1H), 4.76-4.57 (m, 2H), 4.15-3.14 (m, 5H), 3.08-2.79 (m, 1H), 2.37-2.24 (m, 6H), 2.16-2.00 (m, 1H), 1.99-1.81 (m, 1H).

Example 93

((1S,6R)-3-(4,6-Dimethylpyrimidin-2-yl)-3,8-diazabicyclo[4.2.0]octan-8-yl)(4-fluoro-2-(pyrimidin-2-yl)phenyl)methanone

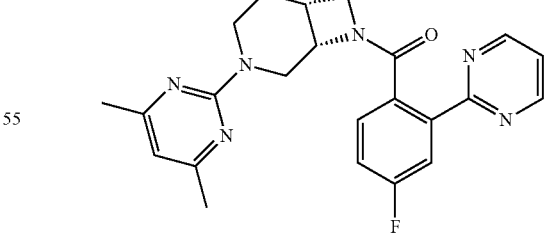

The title compound was prepared in a manner analogous to Example 32, For 2-(3-methyl-1,2,4-oxadiazol-5-yl)benzoic acid. MS (ESI) mass calcd. For $C_{23}H_{23}FN_6O$, 418.48; m/z found 419.2 [M+H]$^+$.

Examples 94-110 may be prepared using the procedures described previously.

Example 94

(1S,6R)-(2-(2H-1,2,3-Triazol-2-yl)phenyl)((1S,6R)-3-(6-(dimethylamino)pyrimidin-4-yl)-3,8-diazabicyclo[4.2.0]octan-8-yl)methanone

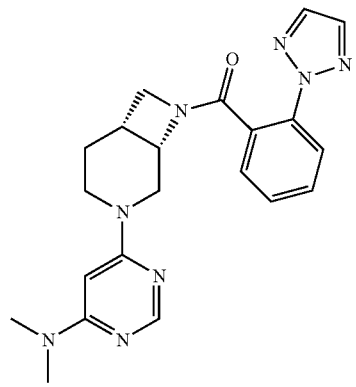 [SMILES: CN(C)c1cc(N2CC[C@@H]3CN(C(=O)c4ccccc4-n4nccn4)[C@@H]3C2)ncn1]

MS (ESI) mass calcd. for C21H24N8O, 404.2.

Example 95

((1S,6R)-3-(6-(Dimethylamino)pyrimidin-4-yl)-3,8-diazabicyclo[4.2.0]octan-8-yl)(3-fluoro-2-(2H-1,2,3-triazol-2-yl)phenyl)methanone

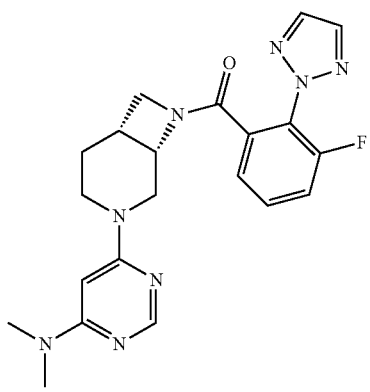 [SMILES: CN(C)c1cc(N2CC[C@@H]3CN(C(=O)c4cccc(F)c4-n4nccn4)[C@@H]3C2)ncn1]

MS (ESI) mass calcd. for C21H23FN8O, 422.2.

Example 96

((1S,6R)-3-(6-(Dimethylamino)pyrimidin-4-yl)-3,8-diazabicyclo[4.2.0]octan-8-yl)(2-fluoro-6-(2H-1,2,3-triazol-2-yl)phenyl)methanone

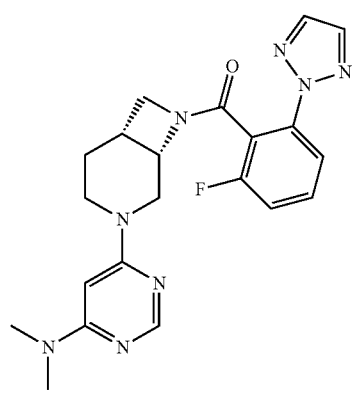 [SMILES: CN(C)c1cc(N2CC[C@@H]3CN(C(=O)c4c(F)cccc4-n4nccn4)[C@@H]3C2)ncn1]

MS (ESI) mass calcd. for C21H23FN8O, 422.2.

Example 97

(3-Methyl-2-(1H-pyrazol-5-yl)phenyl)((1S,6R)-3-(4,5,6-trimethylpyrimidin-2-yl)-3,8-diazabicyclo[4.2.0]octan-8-yl)methanone

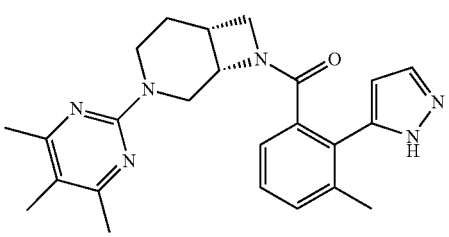

(MS (ESI) mass calcd. For C24H28N6O, 416.52

Example 98

((1S,6R)-3-(5-Fluoro-4,6-dimethylpyrimidin-2-yl)-3,8-diazabicyclo[4.2.0]octan-8-yl)(3-methyl-2-(1H-pyrazol-5-yl)phenyl)methanone

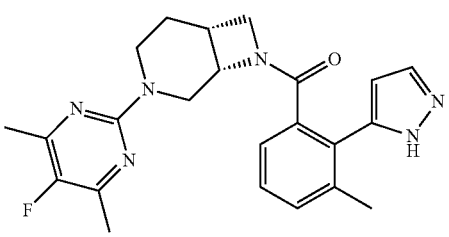 [SMILES: Cc1cccc(C(=O)N2C[C@H]3CCN(c4nc(C)c(C)c(C)n4)C[C@H]32)c1-c1ccn[nH]1]

(MS (ESI) mass calcd. For C23H25FN6O, 420.48

Example 99

((1S,6R)-3-(5-Chloro-4,6-dimethylpyrimidin-2-yl)-3,8-diazabicyclo[4.2.0]octan-8-yl)(3-methyl-2-(1H-pyrazol-5-yl)phenyl)methanone

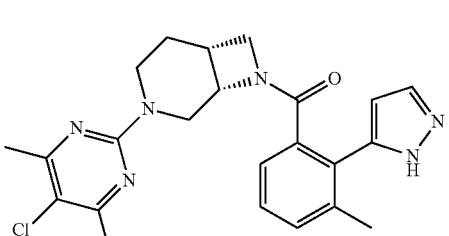

(MS (ESI) mass calcd. For C23H25ClN6O, 436.94

107

Example 100

((1S,6R)-3-(5-Chloro-4,6-dimethylpyrimidin-2-yl)-3,8-diazabicyclo[4.2.0]octan-8-yl)(3-fluoro-2-(1H-pyrazol-5-yl)phenyl)methanone

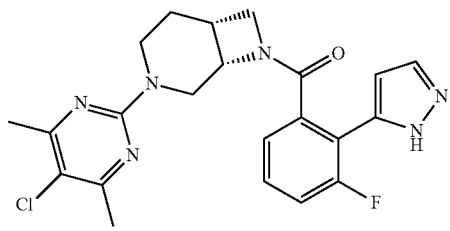 [SMILES: Cc1nc(N2CC[C@@H]3CN(C(=O)c4cccc(F)c4-c4ccn[nH]4)[C@@H]3C2)nc(C)c1Cl]

(MS (ESI) mass calcd. For $C_{22}H_{22}ClFN_6O$, 440.90

Example 101

(3-Fluoro-2-(1H-pyrazol-5-yl)phenyl)((1S,6R)-3-(5-fluoro-4,6-dimethylpyrimidin-2-yl)-3,8-diazabicyclo[4.2.0]octan-8-yl)methanone

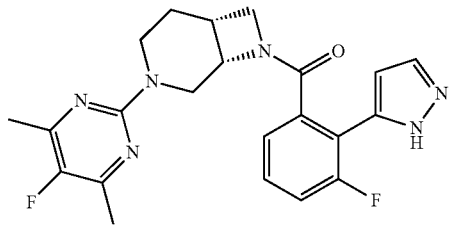 [SMILES: Cc1nc(N2CC[C@@H]3CN(C(=O)c4cccc(F)c4-c4ccn[nH]4)[C@@H]3C2)nc(C)c1C]

MS (ESI) mass calcd. For $C_{22}H_{22}F_2N_6O$, 424.45

Example 102

(3-Fluoro-2-(1H-pyrazol-5-yl)phenyl)((1S,6R)-3-(4,5,6-trimethylpyrimidin-2-yl)-3,8-diazabicyclo[4.2.0]octan-8-yl)methanone

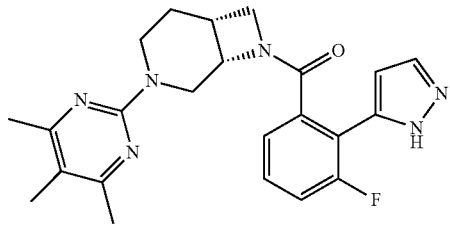 [SMILES: Cc1nc(N2CC[C@@H]3CN(C(=O)c4cccc(F)c4-c4ccn[nH]4)[C@@H]3C2)nc(C)c1C]

(MS (ESI) mass calcd. For $C_{23}H_{25}FN_6O$, 420.48

108

Example 103

(3-Fluoro-2-(1H-pyrazol-5-yl)phenyl)((1S,6R)-3-(4,5,6-trimethylpyrimidin-2-yl)-3,8-diazabicyclo[4.2.0]octan-8-yl)methanone

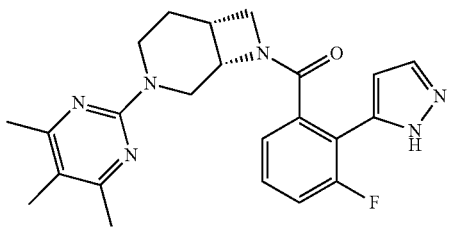

(MS (ESI) mass calcd. For $C_{23}H_{25}FN_6O$, 420.48

Example 104

(3-Fluoro-2-(isoxazol-5-yl)phenyl)((1S,6R)-3-(4,5,6-trimethylpyrimidin-2-yl)-3,8-diazabicyclo[4.2.0]octan-8-yl)methanone

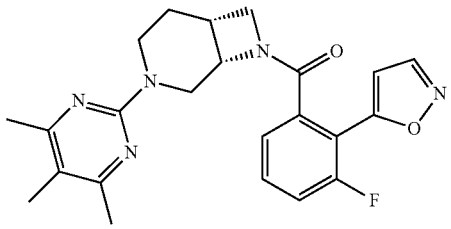 [SMILES: Cc1nc(N2CC[C@@H]3CN(C(=O)c4cccc(F)c4-c4ccno4)[C@@H]3C2)nc(C)c1C]

(MS (ESI) mass calcd. For $C_{23}H_{24}FN_5O_2$, 421.47

Example 105

((1S,6R)-3-(5-Chloro-4,6-dimethylpyrimidin-2-yl)-3,8-diazabicyclo[4.2.0]octan-8-yl)(3-fluoro-2-(isoxazol-5-yl)phenyl)methanone

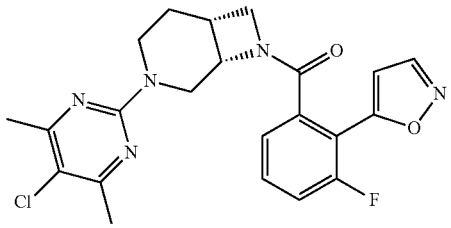 [SMILES: Cc1nc(N2CC[C@@H]3CN(C(=O)c4cccc(F)c4-c4ccno4)[C@@H]3C2)nc(C)c1Cl]

(MS (ESI) mass calcd. For $C_{22}H_{21}ClFN_5O_2$, 441.89

Example 106

(3-Fluoro-2-(isoxazol-5-yl)phenyl)((1S,6R)-3-(5-fluoro-4,6-dimethylpyrimidin-2-yl)-3,8-diazabicyclo[4.2.0]octan-8-yl)methanone

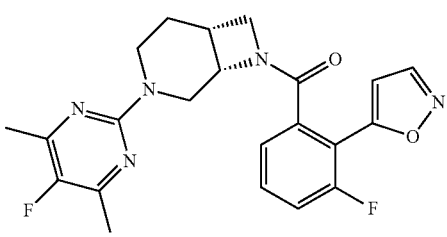

(MS (ESI) mass calcd. For $C_{22}H_{21}F_2N_5O_2$, 425.43

Example 107

((1S,6R)-3-(4,6-Dimethylpyrimidin-2-yl)-3,8-diazabicyclo[4.2.0]octan-8-yl)(3-fluoro-2-(isoxazol-5-yl)phenyl)methanone

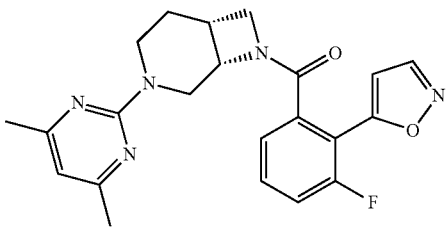 [SMILES: Cc1cc(C)nc(N2CC[C@@H]3CN(C(=O)c4cccc(F)c4-c4ccno4)[C@@H]3C2)n1]

(MS (ESI) mass calcd. For $C_{22}H_{22}FN_5O_2$, 407.44

Example 108

((1S,6R)-3-(4,6-Dimethylpyrimidin-2-yl)-3,8-diazabicyclo[4.2.0]octan-8-yl)(3-fluoro-2-(3-methylisoxazol-5-yl)phenyl)methanone

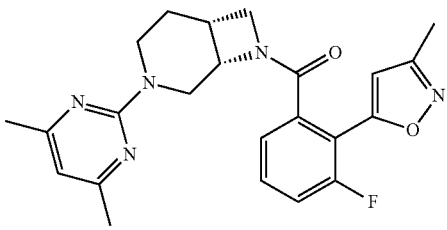 [SMILES: Cc1cc(-c2c(F)cccc2C(=O)N2C[C@H]3CCN(c4nc(C)cc(C)n4)C[C@H]32)on1]

(MS (ESI) mass calcd. For $C_{23}H_{24}FN_5O_2$, 421.47

Example 109

(3-Fluoro-2-(3-methylisoxazol-5-yl)phenyl)((1S,6R)-3-(5-fluoro-4,6-dimethylpyrimidin-2-yl)-3,8-diazabicyclo[4.2.0]octan-8-yl)methanone

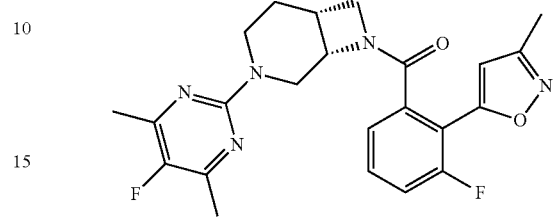

MS (ESI) mass calcd. For $C_{23}H_{23}F_2N_5O_2$, 439.46

Example 110

((1S,6R)-3-(5-Chloro-4,6-dimethylpyrimidin-2-yl)-3,8-diazabicyclo[4.2.0]octan-8-yl)(3-fluoro-2-(3-methylisoxazol-5-yl)phenyl)methanone

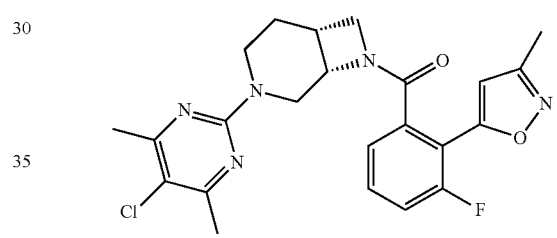

(MS (ESI) mass calcd. For $C_{23}H_{23}ClFN_5O_2$, 455.91

Biological Assays

The in vitro affinity of the compounds for the human orexin-1 and orexin-2 receptors was determined by competitive radioligand binding using [$^3$H]SB SB674042 (1-(5-(2-fluoro-phenyl)-2-methyl-thiazol-4-yl)-1-((S)-2-(5-phenyl-(1,3,4)oxadiazol-2-ylmethyl)-pyrrolidin-1-yl)-methanone) (Langmead et al., *British Journal of Pharmacology* 2004, 141:340-346.) and [$^3$H]EMPA (N-ethyl-2[(6-methoxy-pyridin-3-yl)-(toluene-2-sulfonyl)-amino]-N-pyridin-3-ylm-ethyl acetamide) (Malherbe et al., *British Journal of Pharmacology*, 2009, 156(8), 1326-1341), respectively.

The in vitro functional antagonism of the compounds on the human orexin-1 and orexin-2 receptors was determined using fluorometric imaging plate reader (FLIPR) based calcium assays.

Human Orexin 1 Receptor Radioligand Binding Studies

Chinese ovary cells (CHO) stably expressing human orexin 1 receptor (Genebank accession number NM_001526) were grown to confluency in DMEM/F12 (Gibco, Cat #11039), 10% FBS, 1× Pen/Strep, 600 µg/mL G418 media on 150 cm$^2$ tissue culture plates, washed with 5 mM EDTA in PBS (HyClone Dulbecco's Phoshpate Buffered Saline 1× with Calcium and Magnesium, Cat # SH30264.01, hereafter referred to simply as PBS) and scraped into 50 ml tubes. After centrifugation (2K×G, 10 min at 4° C.), the supernatant was aspirated and the pellets frozen and stored at −80° C. Cells were resuspended in PBS in the presence of 1 tablet of protease inhibitor cocktail (Roche, Cat. #11836145001) per 50 mL. Each cell pellet from a 15 cm plate was resuspended in 10 mL, stored on ice, and vortexed for 45 sec prior to addition to the reactions. Competition binding experiments in 96 well polypropylene plates were performed using [$^3$H]-SB674042 (Moravek Corporation, specific activity=35.3 Ci/mmol), diluted to a 10 nM concentration in PBS (4 nM final). Compounds were solubilized in 100% DMSO (Acros Organics, Cat. #61042-1000) and tested over a range of 7 concentrations (from 0.1 nM to 10 μM). The final concentration of DMSO in the reactions is equal to or less than 0.1%. Total and nonspecific binding was determined in the absence and presence of 10 μM (1-(6,8-difluoro-2-methylquinolin-4-yl)-3-[4-(dimethylamino)phenyl]urea, CAS Registry #288150-92-5). The total volume of each reaction is 200 μL (20 μL of diluted compounds, 80 μL of [$^3$H]-SB674042 diluted in PBS and 100 μL of the cell suspension). Reactions were run for 60 min at room temperature and terminated by filtration through GF/C filter plates (PerkinElmer, Cat. #6005174) presoaked in 0.3% polyethylenimine using the cell harvester (PerkinElmer Filtermate). The plates were washed 3 times by aspirating 30 ml PBS through the plates. Plates were dried in 55° C. oven for 60 min, scintillation fluid was added, and the radioactivity was counted on a Topcount (Packard).

IC$_{50}$ values (i.e. concentration of unlabelled compound required to compete for 50% of specific binding to the radioligand) were calculated using the GraphPad Prism software (GraphPad Prism Software Inc., San Diego, Calif.) with a fit to a sigmoidal dose-response curve. Apparent K$_i$ values were calculated as K$_i$=IC$_{50}$/(1+C/K$_d$), where C is concentration of radioligand and K$_d$=4 nM.

Human Orexin 2 Receptor Radioligand Binding Studies

HEK293 stably expressing human orexin-2 receptor (Genebank accession number NM_001526) were grown to confluency in DMEM/F12 (Gibco, Cat #11039), in DMEM, 10% FBS, 1× Pen/Strep, 1× NaPyruvate, 1× HEPES, 600 ug/ml G418 media on 150 cm$^2$ tissue culture plates, washed with 5 mM EDTA in PBS (HyClone Dulbecco's Phoshpate Buffered Saline 1× with Calcium and Magnesium, Cat # SH30264.01, hereafter referred to simply as PBS) and scraped into 50 ml tubes. After centrifugation (2K×G, 10 min at 4° C.), the supernatant was aspirated and the pellets frozen and stored at −80° C. Cells were resuspended in PBS in the presence of 1 tablet of protease inhibitor cocktail (Roche, Cat. #11836145001) per 50 mL. Each cell pellet from a 15 cm plate was resuspended in 10 mL, stored on ice, and vortexed for 45 sec just prior to addition to the reactions. Competition binding experiments in 96 well polypropylene plates were performed using [$^3$H]-EMPA (Moravek Corporation, specific activity=27 Ci/mmol), diluted to a 20 nM concentration in PBS (5 nM final concentration). Compounds were solubilized in 100% DMSO (Acros Organics, Cat. #61042-1000) and tested over a range of 7 concentrations (from 0.1 nM to 10 μM). The final concentration of DMSO in the reactions is equal to or less than 0.1%. Total and nonspecific binding was determined in the absence and presence of 10 μM (N-[2-(3,4-dimethoxyphenyl)ethyl]-N-methylnaphthalene-1-carboxamide, CAS Registry #1089563-88-1). The total volume of each reaction is 200 μL (20 μL of diluted compounds, 80 μL of [$^3$H]-EMPA diluted in PBS and 100 μL of the cell suspension). Reactions were run for 60 min at room temperature and terminated by filtration through GF/C filter plates (PerkinElmer, Cat. #6005174) presoaked in 0.3% polyethylenimine using the cell harvester (Perkin Elmer Filtermate). The plates were washed 3 times by aspirating 30 ml PBS through the plates. Plates were dried in 55° C. oven for 60 min, scintillation fluid was added, and the radioactivity was counted on a Topcount (Packard). IC$_{50}$ values (i.e. concentration of unlabelled compound required to compete for 50% of specific binding to the radioligand) were calculated using the GraphPad Prism software (GraphPad Prism Software Inc., San Diego, Calif.) with a fit to a sigmoidal dose-response curve. Apparent K$_i$ values were calculated as K$_i$=IC$_{50}$/(1+C/K$_d$), where C is concentration of radioligand and K$_d$=2 nM.

Human Orexin 1 Receptor Ca$^{2+}$ Mobilization Assay

CHO cells stably transfected with the human orexin-1 receptor (Genebank accession number NM_001526) were grown to confluency in DMEM/F12, 10% FBS, 1× Na Pyruvate, 1× pen-strep, 400 μg/ml G418. Cells were seeded on to 96-well Packard viewplates at a density of 50,000 cells/well and incubated overnight at 37° C., 5% CO$_2$. The cells were dye-loaded with 4 μM Ca$^{2+}$ dye Fluo-3AM in serum-free DMEM/F-12 with 2.5 mM probenecid and incubated at 37° C., 5% CO$_2$ for one hour. Cells were pre-incubated with compounds (diluted in DMEM/F-12) for 30 minutes before agonist (orexin A, 10 nM) stimulation. Ligand-induced Ca$^{2+}$ release was measured using a Fluorometric Imaging Plate Reader (FLIPR, Molecular Devices, Sunnyvale, Calif.). Functional responses were measured as peak fluorescence intensity minus basal. The concentration of agonist that produced a half-maximal response is represented by the EC$_{50}$ value. Antagonistic potency values were converted to apparent pK$_B$ values using a modified Cheng-Prusoff correction. Apparent pK$_B$=−log IC$_{50}$/1+[conc agonist/EC$_{50}$]. Data are expressed as mean±S.E.M.

Human Orexin 2 Receptor Ca$^{2+}$ Mobilization Assay

PFSK cells endogenously expressing the human orexin 2 receptor were grown to confluency in RPMI1640, 10% FBS, 1× pen-strep. Cells were seeded on to 96-well Packard viewplates at a density of 50,000 cells/well and incubated overnight at 37° C., 5% CO$_2$. The cells were dye-loaded with 4 μM Ca$^{2+}$ dye Fluo-3AM in serum-free DMEM/F-12 with 2.5 mM probenecid and incubated at 37° C., 5% CO$_2$ for one hour. Cells were pre-incubated with compounds (diluted in DMEM/F-12) for 30 minutes before agonist (orexin B, 100 nM) stimulation. Ligand-induced Ca$^{2+}$ release was measured using a Fluorometric Imaging Plate Reader (FLIPR, Molecular Devices, Sunnyvale, Calif.). Functional responses were measured as peak fluorescence intensity minus basal. The concentration of agonist that produced a half-maximal response is represented by the EC$_{50}$ value. Antagonistic potency values were converted to apparent pK$_B$ values using a modified Cheng-Prusoff correction. Apparent pK$_B$=−log IC$_{50}$/1+[conc agonist/EC$_{50}$]. Data are expressed as mean±S.E.M, the designation of NT means not tested.

| OR 2 Ki (nM) | OR 2 Kb | OR 1 Ki (nM) | OR 2 Ki (nM) | OR 2 Kb | OR 1 Ki (nM) |
| --- | --- | --- | --- | --- | --- |
| 52 | 6 | 92 | 149 | NT | 10000 |
| 104 | 30 | 195 | 197 | NT | 10000 |
| 143 | 42 | 410 | 436 | NT | 3800 |
| 199 | NT | 837 | 37 | NT | 342 |
| 247 | 40 | 169 | 78 | 5 | 794 |
| 315 | NT | 1261 | 66 | 5 | 6059 |
| 604 | 117 | 962 | 55 | 9 | 2550 |
| 952 | NT | 10000 | 980 | NT | 10000 |
| 1226 | NT | 255 | 920 | NT | 10000 |
| 1650 | NT | 1332 | 1385 | NT | 10000 |
| 1560 | NT | 10000 | 150 | NT | 3300 |
| 2528 | NT | 1328 | 1800 | NT | 10000 |
| 1768 | NT | 3588 | 3700 | NT | 10000 |
| 2609 | NT | 10000 | 2700 | NT | 10000 |

-continued

| OR 2 Ki (nM) | OR 2 Kb | OR 1 Ki (nM) | OR 2 Ki (nM) | OR 2 Kb | OR 1 Ki (nM) |
|---|---|---|---|---|---|
| 62 | 50 | 3210 | 910 | NT | 10000 |
| 2214 | NT | 10000 | 17 | 2 | 535 |
| 10000 | NT | 10000 | 1100 | NT | 10000 |
| 846 | NT | 10000 | 92 | NT | 922 |
| 10000 | NT | 10000 | 70 | 6 | 3283 |
| 110 | 126 | 10000 | 11 | 4 | 178 |
| 56 | 4 | 3808 | 6100 | NT | 10000 |
| 37 | 6 | 1751 | 5400 | NT | 10000 |
| 7 | 2 | 214 | 18 | NT | 1396 |
| 17 | 3 | 830 | 370 | NT | 10000 |
| 78 | 13 | 4472 | 220 | NT | 10000 |
| 810 | NT | 10000 | 19 | NT | 1290 |
| 25 | 2 | 762 | 4 | NT | 135 |
| 38 | 14 | 2498 | 280 | NT | 1800 |
| 1100 | NT | 10000 | 3800 | NT | 10000 |
| 590 | NT | 10000 | 97 | 57 | 410 |
| 350 | NT | 10000 | 95 | 59 | 5732 |
| 990 | NT | 10000 | 24 | 7 | 1571 |
| 4399 | NT | 10000 | 92 | 13 | 6928 |
| 750 | NT | 10000 | 10000 | NT | 10000 |
| 10000 | NT | 10000 | 152 | NT | 480 |
| 9 | 3 | 593 | 148 | NT | 5800 |
| 32 | 11 | 1241 | 140 | NT | 5999 |
| 6 | 4 | 108 | 5 | 2 | 431 |
| 6 | 4 | 74 | 83 | 15 | 3742 |
| 320 | NT | 10000 | 220 | NT | 5300 |
| 170 | NT | 2200 | 890 | NT | 10000 |
| 50 | 15 | 4613 | 118 | 19 | 10000 |
| 211 | NT | 10000 | 117 | 8 | 10000 |

What is claimed is:
1. A chemical entity that is a compound of Formula (I):

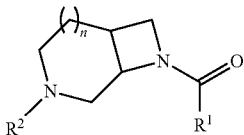

wherein
n is 0-1;
$R^1$ is a member selected from the group consisting of:
  A) phenyl substituted or unsubstituted with $R^a$, and substituted in the ortho position with $R^b$;
  $R^a$ is a member independently selected from the group consisting of: halo, —$C_{1-4}$alkyl, and —$C_{1-4}$alkoxy;
  $R^b$ is a member selected from the group consisting of:
    a) halo or —$C_{1-4}$alkoxy,
    b) thiophen-2-yl, 2H-1,2,3-triazole, 1H-1,2,3-triazol-1-yl, 1H-pyrazol-1-yl, 1H-pyrazol-5-yl, pyrimidin-2-yl, isoxazol-5-yl, 3-methylisoxazol-5-yl or 3-methyl-1,2,4-oxadiazol-5-yl, and
    c) phenyl;
  B) pyridine substituted or unsubstituted with one or two members independently selected from the group consisting of: $C_{1-4}$alkyl and 1H-1,2,3-triazol-1-yl, wherein the substituents are positioned adjacent to the point of attachment by $R^1$; and
  C) methylthiazole substituted with 2-fluorophenyl;
$R^2$ is a member selected from the group consisting of:
  A) 6-membered heteroaryl ring containing two nitrogen members substituted or unsubstituted with one or more members selected from the group consisting of: —$C_{1-4}$ alkyl, —$C_{1-4}$alkoxy, —$CF_3$, halo, —N($C_{1-4}$alkyl)$_2$, —$NH_2$, and phenyl;
  B) pyridine substituted or unsubstituted with one or more members independently selected from the group consisting of: —$CF_3$ and —$C_{1-4}$alkyl;
  C) quinoxalin-2-yl or quinoline substituted or unsubstituted with —$C_{1-4}$alkyl;
  D) benzooxazol-2-yl substituted or unsubstituted with halo; and
  E) 4-methyl-6,7-dihydro-5H-cyclopenta[d]pyrimidine;
and pharmaceutically acceptable salts of compounds of Formula (I).

2. A chemical entity defined in claim 1, wherein n is 0.
3. A chemical entity defined in claim 1, wherein n is 1.
4. A chemical entity defined in claim 1, wherein $R^1$ is phenyl, where $R^a$ is a member selected from the group consisting of —H, —F, —$C_{1-4}$alkoxy, and —$CH_3$, and $R^b$ is a member selected from the group consisting of —Br, —$OCH_3$, thiophen-2-yl, 2H-1,2,3-triazole, 1H-1,2,3-triazol-1-yl, 1H-pyrazol-1-yl, 1H-pyrazol-5-yl, pyrimidin-2-yl, isoxazol-5-yl, 3-methylisoxazol-5-yl, 3-methyl-1,2,4-oxadiazol-5-yl, and phenyl.
5. A chemical entity defined in claim 1, wherein $R^a$ is a member selected from the group consisting of —H, —F, —$OCH_3$, and —$CH_3$.
6. A chemical entity defined in claim 1, wherein $R^1$ is (2-fluoro-phenyl)-2-methyl-thiazol-4-yl.
7. A chemical entity defined in claim 1, wherein $R^1$ is a member selected from the group consisting of biphenyl-2-yl, 2-thiophen-2-yl-phenyl, 2-bromophenyl, 2,6-dimethoxyphenyl, 2-(3-methyl-1,2,4-oxadiazol-5-yl)phenyl, 2-[1,2,3]triazol-2-yl-phenyl, 3-fluoro-2-[1,2,3]triazol-2-yl-phenyl, 2-fluoro-6-[1,2,3]triazol-2-yl-phenyl, 3-fluoro-2-(1H-1,2,3-triazol-1-yl)phenyl, 3-methoxy-2-(1H-1,2,3-triazol-1-yl)phenyl, 3-methyl-2-(1H-1,2,3-triazol-1-yl)phenyl, 2-fluoro-6-(2H-1,2,3-triazol-2-yl)phenyl, 3-fluoro-2-(2H-1,2,3-triazol-2-yl)phenyl, 3-methoxy-2-(2H-1,2,3-triazol-2-yl)phenyl, 4-methoxy-2-(2H-1,2,3-triazol-2-yl)phenyl, 5-methoxy-2-(2H-1,2,3-triazol-2-yl)phenyl, 5-fluoro-2-(2H-1,2,3-triazol-2-yl)phenyl, 3-fluoro-2-(1H-pyrazol-1-yl)phenyl, 3-fluoro-2-(1H-pyrazol-5-yl)phenyl, 3-methyl-2-(1H-pyrazol-1-yl)phenyl, 3-fluoro-2-pyrimidin-2-ylphenyl, 4-fluoro-2-(pyrimidin-2-yl)phenyl, 3-fluoro-2-(3-methyl-isoxazol-5-yl)phenyl or 5-fluoro-2-pyrimidin-2-yl-phenyl.
8. A chemical entity defined in claim 1, wherein $R^1$ is 6-methyl-2-(1H-1,2,3-triazol-1-yl)pyridin-3-yl.
9. A chemical entity defined in claim 1, wherein $R^2$ is pyrazine or pyrimidine substituted or unsubstituted with one or more members selected from the group consisting of —$C_{1-4}$alkyl, —$OCH_3$, —$CF_3$, —Cl, —F, —N($CH_3$)$_2$, —$NH_2$, and phenyl.
10. A chemical entity defined in claim 1, wherein $R^2$ is 2-methylpyrimidin-4-amine, 2-phenylpyrimidin-4-yl, 4-(trifluoromethyl)pyrimidin-2-yl, 4,5,6-trimethylpyrimidin-2-yl, 4,5-dimethylpyrimidin-2-yl, 4,6-dimethoxypyrimidin-2-yl, 4,6-dimethyl-pyrimidin-2-yl, 4-amino-6-methylpyrimidin-2-yl, 4-methoxy-pyrimidin-2-yl, 4-methyl-6-trifluoromethyl-pyrimidin-2-yl, 4-methylpyrimidin-2-yl, 4-phenyl-pyrimidin-2-yl, 5-chloro-4,6-dimethylpyrimidin-2-yl, 5-chloro-4-methylpyrimidin-2-yl, 5-fluoro-4,6-dimethylpyrimidin-2-yl, 5-fluoro-4-methylpyrimidin-2-yl, 6-(trifluoromethyl)pyrimidin-4-yl, 6-methyl-2-(1-methylethyl)pyrimidin-4-yl, N,N,2-trimethylpyrimidin-4-amine, N,N,6-trimethylpyrimidin-2-amine, N,N-dimethylpyrimidin-4-amine, pyrimidin-2-yl-4-amine, or 3,6-dimethylpyrazin-2-yl.
11. A chemical entity defined in claim 1, wherein $R^2$ is pyridine substituted or unsubstituted with one or more members selected from the group consisting of —$CH_3$ and —$CF_3$.

12. A chemical entity defined in claim 1, wherein $R^2$ is 4-(trifluoromethyl)pyridin-2-yl, 4,6-dimethylpyridin-2-yl, 4-methylpyridin-2-yl, or 6-(trifluoromethyl)pyridin-2-yl.

13. A chemical entity defined in claim 1, wherein $R^2$ is 2-methylquinoline, quinoline, or quinoxalin-2-yl.

14. A chemical entity defined in claim 1, wherein $R^2$ is 6-chloro-1,3-benzoxazole or benzooxazol-2-yl.

15. A chemical entity defined in claim 1, wherein $R^2$ is a member selected from the group consisting of 2-methylpyrimidin-4-amine, 2-phenylpyrimidin-4-yl, 4-(trifluoromethyl)pyrimidin-2-yl, 4,5,6-trimethylpyrimidin-2-yl, 4,5-dimethylpyrimidin-2-yl, 4,6-dimethoxypyrimidin-2-yl, 4,6-dimethyl-pyrimidin-2-yl, 4-amino-6-methylpyrimidin-2-yl, 4-methoxy-pyrimidin-2-yl, 4-methyl-6-trifluoromethyl-pyrimidin-2-yl, 4-methylpyrimidin-2-yl, 4-phenyl-pyrimidin-2-yl, 5-chloro-4,6-dimethylpyrimidin-2-yl, 5-chloro-4-methylpyrimidin-2-yl, 5-fluoro-4,6-dimethylpyrimidin-2-yl, 5-fluoro-4-methylpyrimidin-2-yl, 6-(trifluoromethyl)pyrimidin-4-yl, 6-methyl-2-(1-methylethyl)pyrimidin-4-yl, N,N,2-trimethylpyrimidin-4-amine, N,N,6-trimethylpyrimidin-2-amine, N,N-dimethylpyrimidin-4-amine, pyrimidin-2-yl-4-amine, 4-methyl-6,7-dihydro-5H-cyclopenta[d]pyrimidine, 4-(trifluoromethyl)pyridin-2-yl, 4,6-dimethylpyridin-2-yl, 4-methylpyridin-2-yl, 6-(trifluoromethyl)pyridin-2-yl, 2-methylquinoline, quinoline, quinoxalin-2-yl, 6-chloro-1,3-benzoxazole or benzooxazol-2-yl.

16. A chemical entity defined in claim 1, wherein $R^1$ is 2-(3-methyl-1,2,4-oxadiazol-5-yl)phenyl, 2-[1,2,3]triazol-2-yl-phenyl, 2-fluoro-6-[1,2,3]triazol-2-yl-phenyl, 2-fluoro-6-(2H-1,2,3-triazol-2-yl)phenyl, or 5-methoxy-2-(2H-1,2,3-triazol-2-yl)phenyl and $R^2$ is 4,5,6-trimethylpyrimidin-2-yl, 4,5-dimethylpyrimidin-2-yl, or 4,6-dimethyl-pyrimidin-2-yl.

17. A chemical entity selected from the group consisting of:

Biphenyl-2-yl-(3-quinoxalin-2-yl-3,8-diaza-bicyclo[4.2.0]oct-8-yl)-methanone;
(3-Benzooxazol-2-yl-3,8-diaza-bicyclo[4.2.0]oct-8-yl)-biphenyl-2-yl-methanone;
(2,6-Dimethoxy-phenyl)-(3-quinoxalin-6-yl-3,8-diaza-bicyclo[4.2.0]oct-8-yl)-methanone;
[5-(2-Fluoro-phenyl)-2-methyl-thiazol-4-yl]-(3-quinoxalin-6-yl-3,8-diaza-bicyclo[4.2.0]oct-8-yl)-methanone;
Biphenyl-2-yl-[3-(4-phenyl-pyrimidin-2-yl)-3,8-diaza-bicyclo[4.2.0]oct-8-yl]-methanone;
(3-Benzooxazol-2-yl-3,8-diaza-bicyclo[4.2.0]oct-8-yl)-(2,6-dimethoxy-phenyl)-methanone;
(2,6-Dimethoxy-phenyl)-[3-(4-phenyl-pyrimidin-2-yl)-3,8-diaza-bicyclo[4.2.0]oct-8-yl]-methanone;
(1R,6S)[3-(4,6-Dimethyl-pyrimidin-2-yl)-3,8-diaza-bicyclo[4.2.0]oct-8-yl]-(2-thiophen-2-yl-phenyl)-methanone;
(1R,6S)Biphenyl-2-yl-[3-(4,6-dimethyl-pyrimidin-2-yl)-3,8-diaza-bicyclo[4.2.0]oct-8-yl]-methanone;
6-(Biphenyl-2-ylcarbonyl)-3-(4-phenylpyrimidin-2-yl)-3,6-diazabicyclo[3.2.0]heptane;
2-[6-(Biphenyl-2-ylcarbonyl)-3,6-diazabicyclo[3.2.0]hept-3-yl]quinoxaline;
6-[(2-Bromophenyl)carbonyl]-3-(4,6-dimethylpyrimidin-2-yl)-3,6-diazabicyclo[3.2.0]heptane;
3-(4,6-Dimethylpyrimidin-2-yl)-6-[(2-thiophen-2-ylphenyl)carbonyl]-3,6-diazabicyclo[3.2.0]heptane;
6-(Biphenyl-2-ylcarbonyl)-3-(4,6-dimethylpyrimidin-2-yl)-3,6-diazabicyclo[3.2.0]heptane;
6-[(2-Bromophenyl)carbonyl]-3-(4-methylpyrimidin-2-yl)-3,6-diazabicyclo[3.2.0]heptane;
3-(4-Methylpyrimidin-2-yl)-6-[(2-thiophen-2-yl phenyl)carbonyl]-3,6-diazabicyclo[3.2.0]heptane;
6-(Biphenyl-2-ylcarbonyl)-3-(4-methylpyrimidin-2-yl)-3,6-diazabicyclo[3.2.0]heptane;
[3-(4,6-Dimethyl-pyrimidin-2-yl)-3,6-diaza-bicyclo[3.2.0]hept-6-yl]-(5-fluoro-2-pyrimidin-2-yl-phenyl)-methanone;
[3-(4,6-Dimethyl-pyrimidin-2-yl)-3,6-diaza-bicyclo[3.2.0]hept-6-yl]-(2-[1,2,3]triazol-2-yl-phenyl)-methanone;
[3-(4,6-Dimethyl-pyrimidin-2-yl)-3,6-diaza-bicyclo[3.2.0]hept-6-yl]-(2-fluoro-6-[1,2,3]triazol-2-yl-phenyl)-methanone;
[3-(4,6-Dimethyl-pyrimidin-2-yl)-3,6-diaza-bicyclo[3.2.0]hept-6-yl]-(3-fluoro-2-[1,2,3]triazol-2-yl-phenyl)-methanone;
[3-(4,6-Dimethoxy-pyrimidin-2-yl)-3,6-diaza-bicyclo[3.2.0]hept-6-yl]-(2-fluoro-6-[1,2,3]triazol-2-yl-phenyl)-methanone;
(2-Fluoro-6-[1,2,3]triazol-2-yl-phenyl)-[3-(4-methoxy-pyrimidin-2-yl)-3,6-diaza-bicyclo[3.2.0]hept-6-yl]-methanone;
[3-(3,6-Dimethyl-pyrazin-2-yl)-3,6-diaza-bicyclo[3.2.0]hept-6-yl]-(2-fluoro-6-[1,2,3]triazol-2-yl-phenyl)-methanone;
(2-Fluoro-6-[1,2,3]triazol-2-yl-phenyl)-[3-(4-methyl-6-trifluoromethyl-pyrimidin-2-yl)-3,6-diaza-bicyclo[3.2.0]hept-6-yl]-methanone;
(1S,6R)-3-(4,6-Dimethylpyrimidin-2-yl)-8-{[2-(3-methyl-1,2,4-oxadiazol-5-yl)phenyl]carbonyl}-3,8-diazabicyclo[4.2.0]octane;
(1S,6R)-3-(5-Chloro-4-methylpyrimidin-2-yl)-8-{[2-(3-methyl-1,2,4-oxadiazol-5-yl)phenyl]carbonyl}-3,8-diazabicyclo[4.2.0]octane;
(1S,6R)-3-(5-Chloro-4,6-dimethylpyrimidin-2-yl)-8-{[2-(3-methyl-1,2,4-oxadiazol-5-yl)phenyl]carbonyl}-3,8-diazabicyclo[4.2.0]octane;
(1S,6R)-8-{[2-(3-Methyl-1,2,4-oxadiazol-5-yl)phenyl]carbonyl}-3-(4,5,6-trimethylpyrimidin-2-yl)-3,8-diazabicyclo[4.2.0]octane;
(1S,6R)-3-(4,6-Dimethylpyrimidin-2-yl)-8-{[2-fluoro-6-(3-methyl-1,2,4-oxadiazol-5-yl)phenyl]carbonyl}-3,8-diazabicyclo[4.2.0]octane;
N,N-Dimethyl-6-[(1S,6R)-8-{[2-(3-methyl-1,2,4-oxadiazol-5-yl)phenyl]carbonyl}-3,8-diazabicyclo[4.2.0]oct-3-yl]pyrimidin-4-amine;
(1S,6R)-3-(5-Fluoro-4,6-dimethylpyrimidin-2-yl)-8-{[2-(3-methyl-1,2,4-oxadiazol-5-yl)phenyl]carbonyl}-3,8-diazabicyclo[4.2.0]octane;
(6-Methyl-2-(1H-1,2,3-triazol-1-yl)pyridin-3-yl)((1S,6R)-3-(4,5,6-trimethylpyrimidin-2-yl)-3,8-diazabicyclo[4.2.0]octan-8-yl)methanone;
(1S,6R)-3-(5-Fluoro-4-methylpyrimidin-2-yl)-8-{[6-methyl-2-(1H-1,2,3-triazol-1-yl)pyridin-3-yl]carbonyl}-3,8-diazabicyclo[4.2.0]octane;
(1S,6R)-3-(4,5-Dimethylpyrimidin-2-yl)-8-{[6-methyl-2-(1H-1,2,3-triazol-1-yl)pyridin-3-yl]carbonyl}-3,8-diazabicyclo[4.2.0]octane;
(1S,6R)-3-(4,6-Dimethylpyrimidin-2-yl)-8-{[6-methyl-2-(1H-1,2,3-triazol-1-yl)pyridin-3-yl]carbonyl}-3,8-diazabicyclo[4.2.0]octane (1S,6R)-8-{[6-Methyl-2-(1H-1,2,3-triazol-1-yl)pyridin-3-yl]carbonyl}-3-[4-(trifluoromethyl)pyrimidin-2-yl]-3,8-diazabicyclo[4.2.0]octane;
6-Chloro-2-[(1S,6R)-8-{[6-methyl-2-(1H-1,2,3-triazol-1-yl)pyridin-3-yl]carbonyl}-3,8-diazabicyclo[4.2.0]oct-3-yl]-1,3-benzoxazole;

(1S,6R)-8-{[6-Methyl-2-(1H-1,2,3-triazol-1-yl)pyridin-3-yl]carbonyl}-3-[4-(trifluoromethyl)pyridin-2-yl]-3,8-diazabicyclo[4.2.0]octane;

(1S,6R)-3-(4-Methyl pyridin-2-yl)-8-{[6-methyl-2-(1H-1,2,3-triazol-1-yl)pyridin-3-yl]carbonyl}-3,8-diazabicyclo[4.2.0]octane;

(1S,6R)-3-(4,6-Dimethylpyrimidin-2-yl)-8-{[5-methoxy-2-(2H-1,2,3-triazol-2-yl)phenyl]carbonyl}-3,8-diazabicyclo[4.2.0]octane;

(1S,6R)-3-(5-Fluoro-4-methylpyrimidin-2-yl)-8-{[5-methoxy-2-(2H-1,2,3-triazol-2-yl)phenyl]carbonyl}-3,8-diazabicyclo[4.2.0]octane;

(1S,6R)-8-{[5-Methoxy-2-(2H-1,2,3-triazol-2-yl)phenyl]carbonyl}-3-(4,5,6-trimethylpyrimidin-2-yl)-3,8-diazabicyclo[4.2.0]octane;

2-[(1S,6R)-8-{[5-Methoxy-2-(2H-1,2,3-triazol-2-yl)phenyl]carbonyl}-3,8-diazabicyclo[4.2.0]oct-3-yl]-4-methyl-6,7-dihydro-5H-cyclopenta[d]pyrimidine;

2-[(1S,6R)-8-{[5-Methoxy-2-(2H-1,2,3-triazol-2-yl)phenyl]carbonyl}-3,8-diazabicyclo[4.2.0]oct-3-yl]pyrimidin-4-amine;

(1S,6R)-8-{[5-Methoxy-2-(2H-1,2,3-triazol-2-yl)phenyl]carbonyl}-3-[4-(trifluoromethyl)pyrimidin-2-yl]-3,8-diazabicyclo[4.2.0]octane;

6-[(1S,6R)-8-{[5-Methoxy-2-(2H-1,2,3-triazol-2-yl)phenyl]carbonyl}-3,8-diazabicyclo[4.2.0]oct-3-yl]-N,N-dimethylpyrimidin-4-amine;

6-[(1S,6R)-8-{[5-Methoxy-2-(2H-1,2,3-triazol-2-yl)phenyl]carbonyl}-3,8-diazabicyclo[4.2.0]oct-3-yl]-2-methylpyrimidin-4-amine;

(1S,6R)-3-(4,6-Dimethylpyrimidin-2-yl)-8-{[4-methoxy-2-(2H-1,2,3-triazol-2-yl)phenyl]carbonyl}-3,8-diazabicyclo[4.2.0]octane;

(1S,6R)-3-(4,6-Dimethylpyrimidin-2-yl)-8-{[3-methyl-2-(1H-1,2,3-triazol-1-yl)phenyl]carbonyl}-3,8-diazabicyclo[4.2.0]octane;

(1S,6R)-8-{[5-Methoxy-2-(2H-1,2,3-triazol-2-yl)phenyl]carbonyl}-3-[6-methyl-2-(1-methylethyl)pyrimidin-4-yl]-3,8-diazabicyclo[4.2.0]octane;

6-[(1S,6R)-8-{[5-Methoxy-2-(2H-1,2,3-triazol-2-yl)phenyl]carbonyl}-3,8-diazabicyclo[4.2.0]oct-3-yl]-N,N,2-trimethylpyrimidin-4-amine;

4-[(1S,6R)-8-{[5-Methoxy-2-(2H-1,2,3-triazol-2-yl)phenyl]carbonyl}-3,8-diazabicyclo[4.2.0]oct-3-yl]-N,N,6-trimethylpyrimidin-2-amine;

(1S,6R)-3-(4,6-Dimethylpyrimidin-2-yl)-8-{[3-fluoro-2-(1H-pyrazol-1-yl)phenyl]carbonyl}-3,8-diazabicyclo[4.2.0]octane;

(1S,6R)-8-{[4-Methoxy-2-(2H-1,2,3-triazol-2-yl)phenyl]carbonyl}-3-(4,5,6-trimethylpyrimidin-2-yl)-3,8-diazabicyclo[4.2.0]octane;

(1S,6R)-8-{[4-Methoxy-2-(2H-1,2,3-triazol-2-yl)phenyl]carbonyl}-3-[4-(trifluoromethyl)pyrimidin-2-yl]-3,8-diazabicyclo[4.2.0]octane;

(1S,6R)-8-{[4-Methoxy-2-(2H-1,2,3-triazol-2-yl)phenyl]carbonyl}-3-[4-(trifluoromethyl)pyridin-2-yl]-3,8-diazabicyclo[4.2.0]octane;

6-[(1S,6R)-8-{[4-Methoxy-2-(2H-1,2,3-triazol-2-yl)phenyl]carbonyl}-3,8-diazabicyclo[4.2.0]oct-3-yl]-N,N-dimethylpyrimidin-4-amine;

6-[(1S,6R)-8-{[4-Methoxy-2-(2H-1,2,3-triazol-2-yl)phenyl]carbonyl}-3,8-diazabicyclo[4.2.0]oct-3-yl]-N,N,2-trimethylpyrimidin-4-amine;

4-[(1S,6R)-8-{[4-Methoxy-2-(2H-1,2,3-triazol-2-yl)phenyl]carbonyl}-3,8-diazabicyclo[4.2.0]oct-3-yl]-N,N,6-trimethylpyrimidin-2-amine;

(1S,6R)-8-{[4-Methoxy-2-(2H-1,2,3-triazol-2-yl)phenyl]carbonyl}-3-[6-methyl-2-(1-methylethyl)pyrimidin-4-yl]-3,8-diazabicyclo[4.2.0]octane;

((1S,6R)-3-(4-amino-6-methylpyrimidin-2-yl)-3,8-diazabicyclo[4.2.0]octan-8-yl)(4-methoxy-2-(2H-1,2,3-triazol-2-yl)phenyl)methanone;

(1R,6S)-3-(4,6-Dimethylpyrimidin-2-yl)-8-{[2-fluoro-6-(2H-1,2,3-triazol-2-yl)phenyl]carbonyl}-3,8-diazabicyclo[4.2.0]octane;

(1S,6R)-3-(4,6-Dimethylpyrimidin-2-yl)-8-{[2-fluoro-6-(2H-1,2,3-triazol-2-yl)phenyl]carbonyl}-3,8-diazabicyclo[4.2.0]octane;

(1R,6S)-8-{[2-Fluoro-6-(2H-1,2,3-triazol-2-yl)phenyl]carbonyl}-3-[4-(trifluoromethyl)pyrimidin-2-yl]-3,8-diazabicyclo[4.2.0]octane;

(1S,6R)-8-{[2-Fluoro-6-(2H-1,2,3-triazol-2-yl)phenyl]carbonyl}-3-[4-(trifluoromethyl)pyrimidin-2-yl]-3,8-diazabicyclo[4.2.0]octane;

(1S,6R)-3-(4,6-Dimethylpyridin-2-yl)-8-{[2-fluoro-6-(2H-1,2,3-triazol-2-yl)phenyl]carbonyl}-3,8-diazabicyclo[4.2.0]octane;

(1S,6R)-8-{[2-Fluoro-6-(2H-1,2,3-triazol-2-yl)phenyl]carbonyl}-3-(4,5,6-trimethylpyrimidin-2-yl)-3,8-diazabicyclo[4.2.0]octane;

4-[(1S,6R)-8-{[2-Fluoro-6-(2H-1,2,3-triazol-2-yl)phenyl]carbonyl}-3,8-diazabicyclo[4.2.0]oct-3-yl]quinoline;

4-[(1S,6R)-8-{[2-Fluoro-6-(2H-1,2,3-triazol-2-yl)phenyl]carbonyl}-3,8-diazabicyclo[4.2.0]oct-3-yl]-2-methylquinoline;

(1S,6R)-3-(4,6-Dimethylpyrimidin-2-yl)-8-{[5-fluoro-2-(2H-1,2,3-triazol-2-yl)phenyl]carbonyl}-3,8-diazabicyclo[4.2.0]octane;

(1S,6R)-3-(3,6-Dimethylpyrazin-2-yl)-8-{[5-fluoro-2-(2H-1,2,3-triazol-2-yl)phenyl]carbonyl}-3,8-diazabicyclo[4.2.0]octane;

(1S,6R)-8-{[5-Fluoro-2-(2H-1,2,3-triazol-2-yl)phenyl]carbonyl}-3-(4-methylpyrimidin-2-yl)-3,8-diazabicyclo[4.2.0]octane;

(1S,6R)-3-(4,5-Dimethylpyrimidin-2-yl)-8-{[5-fluoro-2-(2H-1,2,3-triazol-2-yl)phenyl]carbonyl}-3,8-diazabicyclo[4.2.0]octane;

(1S,6R)-8-{[5-Fluoro-2-(2H-1,2,3-triazol-2-yl)phenyl]carbonyl}-3-(4,5,6-trimethylpyrimidin-2-yl)-3,8-diazabicyclo[4.2.0]octane;

(1S,6R)-8-{[5-Fluoro-2-(2H-1,2,3-triazol-2-yl)phenyl]carbonyl}-3-[4-(trifluoromethyl)pyrimidin-2-yl]-3,8-diazabicyclo[4.2.0]octane;

(1S,6R)-8-{[5-Fluoro-2-(2H-1,2,3-triazol-2-yl)phenyl]carbonyl}-3-[6-(trifluoromethyl)pyrimidin-4-yl]-3,8-diazabicyclo[4.2.0]octane;

(1S,6R)-8-{[5-Fluoro-2-(2H-1,2,3-triazol-2-yl)phenyl]carbonyl}-3-[6-(trifluoromethyl)pyridin-2-yl]-3,8-diazabicyclo[4.2.0]octane;

(1S,6R)-8-{[5-Fluoro-2-(2H-1,2,3-triazol-2-yl)phenyl]carbonyl}-3-[4-(trifluoromethyl)pyridin-2-yl]-3,8-diazabicyclo[4.2.0]octane;

(1S,6R)-3-(4,6-Dimethylpyrimidin-2-yl)-8-{[3-fluoro-2-(2H-1,2,3-triazol-2-yl)phenyl]carbonyl}-3,8-diazabicyclo[4.2.0]octane;

(1S,6R)-3-(5-Fluoro-4-methylpyrimidin-2-yl)-8-{[3-fluoro-2-(2H-1,2,3-triazol-2-yl)phenyl]carbonyl}-3,8-diazabicyclo[4.2.0]octane;

(1S,6R)-8-{[3-Fluoro-2-(2H-1,2,3-triazol-2-yl)phenyl]carbonyl}-3-[6-(trifluoromethyl)pyrimidin-4-yl]-3,8-diazabicyclo[4.2.0]octane;

(1S,6R)-8-{[3-Fluoro-2-(2H-1,2,3-triazol-2-yl)phenyl]carbonyl}-3-[6-(trifluoromethyl)pyridin-2-yl]-3,8-diazabicyclo[4.2.0]octane;
(1S,6R)-8-{[3-Fluoro-2-(2H-1,2,3-triazol-2-yl)phenyl]carbonyl}-3-[4-(trifluoromethyl)pyridin-2-yl]-3,8-diazabicyclo[4.2.0]octane;
(1S,6R)-3-(4,6-Dimethylpyrimidin-2-yl)-8-[(3-fluoro-2-pyrimidin-2-ylphenyl)carbonyl]-3,8-diazabicyclo[4.2.0]octane;
(1S,6R)-3-(4,6-Dimethylpyrimidin-2-yl)-8-{[3-fluoro-2-(1H-pyrazol-5-yl)phenyl]carbonyl}-3,8-diazabicyclo[4.2.0]octane;
(1S,6R)-3-(4,6-Dimethylpyrimidin-2-yl)-8-{[3-methyl-2-(1H-pyrazol-1-yl)phenyl]carbonyl}-3,8-diazabicyclo[4.2.0]octane;
(1S,6R)-3-(4,6-Dimethylpyrimidin-2-yl)-8-{[3-methoxy-2-(2H-1,2,3-triazol-2-yl)phenyl]carbonyl}-3,8-diazabicyclo[4.2.0]octane;
(1S,6R)-3-(4,6-Dimethylpyrimidin-2-yl)-8-{[3-methoxy-2-(1H-1,2,3-triazol-1-yl)phenyl]carbonyl}-3,8-diazabicyclo[4.2.0]octane;
(1S,6R)-3-(4,6-Dimethylpyrimidin-2-yl)-8-{[3-fluoro-2-(1H-1,2,3-triazol-1-yl)phenyl]carbonyl}-3,8-diazabicyclo[4.2.0]octane;
((1S,6R)-3-(4,6-dimethylpyrimidin-2-yl)-3,8-diazabicyclo[4.2.0]octan-8-yl)(4-fluoro-2-(pyrimidin-2-yl)phenyl)methanone;
(2-(2H-1,2,3-Triazol-2-yl)phenyl)((1S,6R)-3-(6-(dimethylamino)pyrimidin-4-yl)-3,8-diazabicyclo[4.2.0]octan-8-yl)methanone;
((1S,6R)-3-(6-(Dimethylamino)pyrimidin-4-yl)-3,8-diazabicyclo[4.2.0]octan-8-yl)(3-fluoro-2-(2H-1,2,3-triazol-2-yl)phenyl)methanone;
((1S,6R)-3-(6-(Dimethylamino)pyrimidin-4-yl)-3,8-diazabicyclo[4.2.0]octan-8-yl)(2-fluoro-6-(2H-1,2,3-triazol-2-yl)phenyl)methanone;
(3-Methyl-2-(1H-pyrazol-5-yl)phenyl)((1S,6R)-3-(4,5,6-trimethylpyrimidin-2-yl)-3,8-diazabicyclo[4.2.0]octan-8-yl)methanone;
((1S,6R)-3-(5-Fluoro-4,6-dimethylpyrimidin-2-yl)-3,8-diazabicyclo[4.2.0]octan-8-yl)(3-methyl-2-(1H-pyrazol-5-yl)phenyl)methanone;
((1S,6R)-3-(5-Chloro-4,6-dimethylpyrimidin-2-yl)-3,8-diazabicyclo[4.2.0]octan-8-yl)(3-methyl-2-(1H-pyrazol-5-yl)phenyl)methanone;
((1S,6R)-3-(5-Chloro-4,6-dimethylpyrimidin-2-yl)-3,8-diazabicyclo[4.2.0]octan-8-yl)(3-fluoro-2-(1H-pyrazol-5-yl)phenyl)methanone;
(3-Fluoro-2-(1H-pyrazol-5-yl)phenyl)((1S,6R)-3-(5-fluoro-4,6-dimethylpyrimidin-2-yl)-3,8-diazabicyclo[4.2.0]octan-8-yl)methanone;
(3-Fluoro-2-(1H-pyrazol-5-yl)phenyl)((1S,6R)-3-(4,5,6-trimethylpyrimidin-2-yl)-3,8-diazabicyclo[4.2.0]octan-8-yl)methanone;
(3-Fluoro-2-(1H-pyrazol-5-yl)phenyl)((1S,6R)-3-(4,5,6-trimethylpyrimidin-2-yl)-3,8-diazabicyclo[4.2.0]octan-8-yl)methanone;
(3-Fluoro-2-(isoxazol-5-yl)phenyl)((1S,6R)-3-(4,5,6-trimethylpyrimidin-2-yl)-3,8-diazabicyclo[4.2.0]octan-8-yl)methanone;
((1S,6R)-3-(5-Chloro-4,6-dimethylpyrimidin-2-yl)-3,8-diazabicyclo[4.2.0]octan-8-yl)(3-fluoro-2-(isoxazol-5-yl)phenyl)methanone;
(3-Fluoro-2-(isoxazol-5-yl)phenyl)((1S,6R)-3-(5-fluoro-4,6-dimethylpyrimidin-2-yl)-3,8-diazabicyclo[4.2.0]octan-8-yl)methanone;
((1S,6R)-3-(4,6-Dimethylpyrimidin-2-yl)-3,8-diazabicyclo[4.2.0]octan-8-yl)(3-fluoro-2-(isoxazol-5-yl)phenyl)methanone;
((1S,6R)-3-(4,6-Dimethylpyrimidin-2-yl)-3,8-diazabicyclo[4.2.0]octan-8-yl)(3-fluoro-2-(3-methylisoxazol-5-yl)phenyl)methanone;
(3-Fluoro-2-(3-methylisoxazol-5-yl)phenyl)((1S,6R)-3-(5-fluoro-4,6-dimethylpyrimidin-2-yl)-3,8-diazabicyclo[4.2.0]octan-8-yl)methanone; and
((1S,6R)-3-(5-Chloro-4,6-dimethylpyrimidin-2-yl)-3,8-diazabicyclo[4.2.0]octan-8-yl)(3-fluoro-2-(3-methylisoxazol-5-yl)phenyl)methanone.

18. A pharmaceutical composition comprising:
(A) an effective amount of at least one chemical entity selected from compounds of Formula (I):

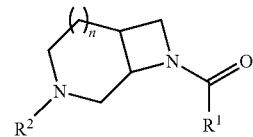

wherein
n is 0-1;
$R^1$ is a member selected from the group consisting of:
a) phenyl substituted or unsubstituted with $R^a$, and substituted in the ortho position with $R^b$;
$R^a$ is a member independently selected from the group consisting of: halo, —$C_{1-4}$ alkyl, and —$C_{1-4}$alkoxy;
$R^b$ is a member selected from the group consisting of:
i) halo or —$C_{1-4}$alkoxy,
ii) thiophen-2-yl, 2H-1,2,3-triazole, 1H-1,2,3-triazol-1-yl, 1H-pyrazol-1-yl, 1H-pyrazol-5-yl, pyrimidin-2-yl, isoxazol-5-yl, 3-methylisoxazol-5-yl or 3-methyl-1,2,4-oxadiazol-5-yl; and
iii) phenyl;
b) pyridine substituted or unsubstituted with one or two members independently selected from the group consisting of: $C_{1-4}$alkyl and 1H-1,2,3-triazol-1-yl, wherein the substituents are positioned adjacent to the point of attachment by $R^1$; and
c) methylthiazole substituted with 2-fluorophenyl;
$R^2$ is a member selected from the group consisting of:
a) 6-membered heteroaryl ring containing two nitrogen members substituted or unsubstituted with one or more members selected from the group consisting of:
—$C_{1-4}$alkyl, —$C_{1-4}$alkoxy, —$CF_3$, halo, —$N(C_{1-4}alkyl)_2$, —$NH_2$, and phenyl;
b) pyridine substituted or unsubstituted with one or more members independently selected from the group consisting of: —$CF_3$ and —$C_{1-4}$alkyl;
c) quinoxalin-2-yl or quinoline substituted or unsubstituted with —$C_{1-4}$alkyl;
d) benzooxazol-2-yl substituted or unsubstituted with halo; and
e) 4-methyl-6,7-dihydro-5H-cyclopenta[d]pyrimidine;
and pharmaceutically acceptable salts of compounds of Formula (I); and
(B) at least one pharmaceutically acceptable excipient.

* * * * *